United States Patent
Bisacchi et al.

(10) Patent No.: US 6,642,252 B2
(45) Date of Patent: Nov. 4, 2003

(54) ACID DERIVATIVES USEFUL AS SERINE PROTEASE INHIBITORS

(75) Inventors: Gregory S. Bisacchi, Ringoes, NJ (US); James C. Sutton, Princeton Junction, NJ (US); William A. Slusarchyk, Skillman, NJ (US); Uwe D. Treuner, Nittendorf (DE); Guohua Zhao, Princeton, NJ (US); Daniel L. Cheney, Ringoes, NJ (US); Yan Shi, Flourtown, PA (US); Shung C. Wu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

(21) Appl. No.: 10/052,927

(22) Filed: Nov. 7, 2001

(65) Prior Publication Data

US 2003/0166685 A1 Sep. 4, 2003

Related U.S. Application Data

(60) Provisional application No. 60/246,392, filed on Nov. 7, 2000.

(51) Int. Cl.$^7$ .................. C07D 401/02; A61K 31/47
(52) U.S. Cl. .................. 514/310; 514/338; 514/354; 546/143; 546/273.4; 546/323
(58) Field of Search .................. 546/143, 273.4, 546/323; 514/310, 338, 354

(56) References Cited

U.S. PATENT DOCUMENTS

| | | | |
|---|---|---|---|
| 3,996,045 A | 12/1976 | Ishii | .................. 546/194 |
| 5,612,341 A | 3/1997 | Lee et al. | |
| 6,248,767 B1 | 6/2001 | Blok et al. | |

FOREIGN PATENT DOCUMENTS

| | | |
|---|---|---|
| EP | 0206567 | 12/1986 |
| GB | 2056968 | 3/1981 |
| JP | 3-7277 | 1/1991 |
| WO | WO 96/40111 | 12/1996 |
| WO | WO 97/31910 | 9/1997 |
| WO | WO98/47876 | 10/1998 |
| WO | WO 98/57937 | 12/1998 |
| WO | WO98/57937 | 12/1998 |
| WO | WO99/41231 | 8/1999 |
| WO | WO00/43374 | 7/2000 |
| WO | WO01/23374 A1 | 4/2001 |
| WO | WO01/44172 A1 | 6/2001 |
| WO | WO01/70678 | 9/2001 |
| WO | WO02/04423 A1 | 1/2002 |
| WO | WO02/24654 | 3/2002 |
| WO | WO02/34711 A1 | 5/2002 |

OTHER PUBLICATIONS

Kondo et al., Chem. Pharm. Cull. 42(1) pp. 62–66 (1994).
Takahasi et al., J. Chem. Soc. Perkin Trans. 1, (1993) pp. 1473–1479.
Xie, et al., J. Med. Chem., (1995) 38, pp. 3003–3008.
Pan et al., Journal of Medicinal Chemistry, (1970), vol. 13, No. 3 pp. 567–568.
Kesaru et al., Tetrahedron, vol. 48, No. 5 (1992) pp. 913–922.
Kohrt et al., Tetrahedron Letters, 41 (2000) pp. 6041–6044.

*Primary Examiner*—Zinna Northington Davis
(74) *Attorney, Agent, or Firm*—Anastasia P. Winslow; Jing S. Belfield

(57) ABSTRACT

Compounds having the formula (I),

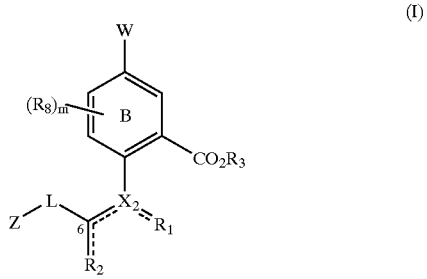

are useful as serine protease inhibitors, more particularly inhibitors of Factors VIIa, IXa, Xa, and/or XIa, wherein ring B is phenyl or pyridyl, W is preferably $C(=O)NR_4R_5$, L is a linker group, $X_2$ comprises nitrogen or carbon, Z is an optionally-substituted monocyclic or bicyclic ring system, and $R_1$, $R_2$, $R_3$, $R_4$, $R_5$ and $R_6$ are as defined in the specification.

24 Claims, No Drawings

ACID DERIVATIVES USEFUL AS SERINE PROTEASE INHIBITORS

RELATED APPLICATIONS

This application claims the benefit of U.S. Provisional Application No. 60/246,392, filed Nov. 7, 2000, incorporated herein by reference.

FIELD OF THE INVENTION

The present invention relates to acid derivatives that are inhibitors of serine proteases such as Factor VIIa, Factor IXa, Factor Xa, Factor FXIa, tryptase, and urokinase. These acid derivatives are useful as anticoagulants in treating and preventing cardiovascular diseases, as anti-inflammatory agents, and as metastasis inhibitors in treating cancer.

BACKGROUND OF THE INVENTION

Under normal conditions, the coagulation system is naturally balanced in favor of anticoagulation by a number of proteins circulating in the blood. These proteins include antithrombin III, a serine-protease inhibitor, and protein C, a vitamin-K dependent protein formed in the liver. When injury or trauma occurs, thrombin is produced at precise levels through an ordered series of reactions. Thrombin is a proteolytic enzyme that occupies a central position in the coagulation process. Thrombin catalyzes the conversion of fibrinogen to fibrin, is a key effector enzyme for blood clotting, and also is pivotal for other functions, such as activation of helper proteins (including Factors V and VIII and thrombomodulin), and its own activation. Disturbances in the natural balance between pro- and anti-coagulant forces may result in bleeding or thrombotic diseases.

The series of reactions leading to thrombin production involve a number of coagulation factors present in the blood as precursors (e.g., Factors VII–XII). When the coagulation system is triggered (e.g., when trauma occurs), the coagulation factors are transformed into activated factors (e.g., Factors VIIa, IXa, Xa, XIa, etc.). Factor VII forms a complex with a membrane protein called tissue factor, to which Factor VIIa tightly binds. Thus, Factor VIIa is present as a complex bound to tissue factor. When triggered, the coagulation factors and tissue factor complexes undergo an ordered chain of reactions that ultimately lead to conversion of Factor X to Factor Xa, and Factor Xa catalyzes the conversion of prothrombin to thrombin.

An elevated plasma level of coagulation factors, particularly Factor VIIa, is a risk factor for fatal myocardial infarction and associated with coronary artery disease and other abnormalities of the coagulation system, e.g., thrombosis, ischemic vascular disease, intravascular clotting, stroke, embolisms, and so forth. Accordingly, antithrombotic agents have been researched and developed for use in treating cardiovascular and other diseases. Presently established antithrombotic agents include heparin, coumarin, and aspirin, among others. There are, however, limitations with these agents. For example, both heparin and coumarin have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding. Thrombin inhibitors and their drawbacks are further discussed in WO 96/20689 to duPont Merck Pharmaceutical Co.

As may be appreciated, those in the field of pharmaceutical research continue to seek to develop new compounds and compositions having increased effectiveness and bioavailability and/or having fewer side effects. See, e.g., Jakobsen et al., "Inhibitors of the Tissue Factor/Factor VIIa-induced Coagulation: Synthesis and In vitro Evaluation of Novel Specific 2-aryl Substituted 4H-3,1-benzoxazin-4-ones," Bioorganic & Medicinal Chemistry, Vol. 8 (August 2000), at pp. 2095–2103; and J. Hirsh et al., "Thrombosis, New Antithrombotic Agents," Lancet, Vol. 353 (Apr. 24, 1999), at pp. 1431–36. There is particularly an interest in developing agents that can selectively and directly inhibit key factors in the complicated coagulation process. Compounds effective in inhibiting Factor Xa are described in U.S. Pat. application Ser. No. 09/478,632, filed Jan. 6, 2000, Ser. No. 09/633,751, filed Aug. 7, 2000, and Ser. No. 09/496,571, filed Feb. 2, 2000. Compounds effective in inhibiting Factors VIIa, Xa, as well as tryptase and urokinase are described in U.S. patent application Ser. No. 09/458,847, filed Dec. 13, 1999. The above referenced '632, '751, '571, and '847 applications show lactam compounds and are each assigned to the present assignee with common inventors herewith. Factor Xa inhibitors are also disclosed in PCT applic. WO 98/57937 to the duPont Merck Pharmaceutical Co.

PCT patent application WO 99/41231 to Ono Pharmaceuticals Inc., ("Ono") discloses a series of amidino derivatives such as 2-(3-(4-amidinophenylcarbamoyl)-naphthalen-2-yl)-5-((2,2-methylpropyl)carbamoyl benzoic acid, which are claimed to be Factor VIIa inhibitors. The Ono application is discussed in Kohrt et al., "An Efficient Synthesis of 2-(3-(4-Amidinophenylcarbamoyl)naphthalen-2-yl)-5-((2,2-methylpropyl)carbamoyl benzoic acid: a Factor VIIa Inhibitor Discovered by the Ono Pharmaceutical Company," Tetrahedron Letters, Vol. 41 (June 2000), at pp. 6041–44, which reports that Ono fails to fully describe an effective method for making the titled compound. Inhibitors of Factor VIIa are also reported in WO 01/44172 to Axys Pharm. Inc. PCT patent application WO 98/47876 to Akzo Novel N. V., published Oct. 29, 1998, discloses certain bicyclic groups such as isoquinoline groups which reportedly are advantageous for promoting pharmacological properties, and isoquinoline-containing compounds are disclosed in WO 94/29273 to SmithKline Beecham Corp. Biphenyl compounds and/or acid substituted bicyclic compounds are also disclosed in U.S. Pat. Nos. 5,612,341, 6,248,767 B1, 3,995,045, EP patent application 0 206 567 A2 to Warner Lambert Co., and WO 01/70678 to Merck Patent GmbH.

The patents, patent applications, and articles cited above are incorporated herein by reference.

The present invention provides acid-based compounds useful as inhibitors of Factor VIIa, Factor IXa, Factor Xa, Factor FXIa, tryptase, and urokinase.

SUMMARY OF THE INVENTION

Acid derivatives are provided that are inhibitors of serine proteases having the Formula I:

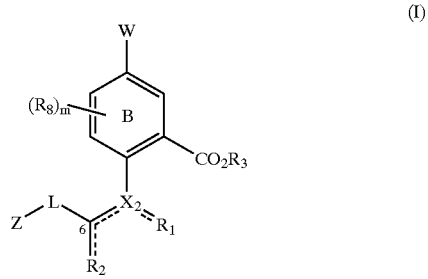

or pharmaceutically-acceptable salts, hydrates or prodrugs thereof, wherein:

W is selected from $C_{2-10}$alkyl, $C_{2-10}$alkenyl, substituted $C_{2-10}$alkyl, substituted $C_{2-10}$alkenyl, —C(=O)NR$_4$R$_5$, —OR$_6$, —CO$_2$R$_4$, —C(=O)R$_4$, —SR$_4$, —S(O)$_p$R$_4$, —NR$_4$R$_5$, —NR$_4$SO$_2$R$_5$, —NR$_{4a}$SO$_2$NR$_4$R$_5$, —NR$_4$CO$_2$R$_5$, —NR$_4$C(=O)R$_5$, —NR$_{4a}$C(=O)NR$_4$R$_5$, —SO$_2$NR$_4$R$_5$, heterocyclo, heteroaryl, aryl, and cycloalkyl;

ring B is phenyl or pyridyl;

$X_2$ is N, CH, or C, provided that $X_2$ is C when $R_1$ and $R_2$ join to form a fully unsaturated ring;

L is —(CR$_{18}$R$_{19}$)$_s$—Y—(CR$_{18a}$R$_{19a}$)$_t$;

Y is selected from —C(=O), —C(=O)NR$_{13}$—, —NR$_{13}$C(=O)—, —NR$_{13}$CR$_{14}$R$_{15}$—, —CR$_{14}$R$_{15}$NR$_{13}$—, and —CR$_{13}$R$_{14}$—CR$_{15}$R$_{16}$—;

Z is a 5 to 7-membered monocyclic or 8 to 11-membered bicyclic aryl, heteroaryl, heterocyclo, or cycloalkyl, wherein each Z group is optionally substituted with up to two R$_{20}$ and/or up to one R$_{21}$, except Z is not phenyl substituted with phenyloxy when W is methoxy, s is 0 and Y is —CH$_2$—CH$_2$—;

R$_1$ and R$_2$ (i) are independently selected from hydrogen, alkyl, substituted alkyl, alkenyl, substituted alkenyl, heteroaryl, aryl, heterocyclo, and cycloalkyl; or (ii) are taken together to form an aryl, heteroaryl, cycloalkyl, or heterocyclo, provided that R$_1$ and R$_2$ do not together form pyrazole when W is methoxy and Z is biphenyl; and when R$_1$ and R$_2$ individually or together form a heteroaryl, aryl, heterocyclo, or cycloalkyl, said cyclic group is optionally substituted with up to three R$_{26}$;

R$_3$ is hydrogen, alkyl, substituted alkyl, heteroaryl, aryl, heterocyclo, cycloalkyl, or alkyl substituted with —OC(=O)R$_{24}$ or —OC(=O)OR$_{24}$, wherein R$_{24}$ is alkyl, substituted alkyl, or cycloalkyl, provided that R$_3$ is not phenyl when W is methoxy;

R$_4$, R$_{4a}$, R$_5$ and R$_6$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, and cycloalkyl; or alternatively, (ii) R$_4$ and R$_5$ may be taken together to form a five-to-seven membered heteroaryl or heterocyclo, except when W is —S(O)$_p$R$_4$, then R$_4$ is not hydrogen;

R$_8$ and R$_{26}$ (i) are at each occurrence independently selected from hydrogen, OR$_{30}$, NR$_{31}$R$_{32}$, NR$_{31}$SO$_2$R$_{32a}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl, or (ii) two of R$_8$ and/or two of R$_{26}$ may be taken together to form a fused benzo ring, a fused heteroaryl, a fused cycloalkyl, or a fused heterocyclo other than a five or six membered heterocyclo having as its heteroatoms two oxygen atoms, provided further that when two R$_{26}$ form a fused benzo ring, then Z is not phenyl substituted in the para position with cyano or a five-membered heterocycle or heteroaryl;

R$_{13}$, R$_{14}$, R$_{15}$, R$_{16}$, R$_{18}$, R$_{18a}$, R$_{19}$, and R$_{19a}$ are selected from hydrogen, lower alkyl, hydroxy, and lower alkyl substituted with hydroxy or halogen;

R$_{20}$ and R$_{21}$ are independently selected at each occurrence from hydrogen, halogen, alkyl, substituted alkyl, haloalkyl, haloalkoxy, cyano, nitro, —C(=O)NR$_{22}$R$_{23}$, —OR$_{22}$, —CO$_2$R$_{22}$, —C(=O)R$_{22}$, —SR$_{22}$, —S(O)$_q$R$_{22a}$, —NR$_{22}$R$_{23}$, —NR$_{22}$SO$_2$R$_{23}$ NR$_{22}$, —NR$_{22}$CO$_2$R$_{23}$, —NR$_{22}$C(=O)R$_{23}$, —NR$_{22}$C(=O)NR$_{23}$R$_{33}$, —SO$_2$NR$_{22}$R$_{23}$, —NR$_{22}$SO$_2$NR$_{23}$R$_{33}$, five or six membered heterocyclo or heteroaryl, phenyl, and four to seven membered cycloalkyl, wherein when R$_{20}$ and/or R$_{21}$ independent of each other comprise a cyclic group, each cyclic group in turn is optionally substituted with up to three of $C_{1-4}$alkyl, $C_{1-4}$alkoxy, halogen, hydroxy, haloalkyl, haloalkoxy, amino, alkylamino, and/or cyano;

R$_{22}$, R$_{23}$ and R$_{33}$ are independently selected from hydrogen, alkyl, and substituted alkyl;

R$_{22a}$ is alkyl or substituted alkyl;

R$_{30}$ at each occurrence is selected from hydrogen, alkyl, substituted alkyl, alkenyl, substituted alkenyl, cycloalkyl, and phenyl;

R$_{31}$ and R$_{32}$ at each occurrence are independently selected from hydrogen, alkyl, substituted alkyl, alkenyl, substituted alkenyl, and cycloalkyl;

R$_{32a}$ is alkyl, substituted alkyl, alkenyl, substituted alkenyl, or cycloalkyl;

m is 0, 1 or 2 when ring B is phenyl and 0 or 1 when ring B is pyridyl;

p and q are independently 1 or 2; and s and t are independently 0, 1 or 2.

The compounds of this invention are surprisingly selective inhibitors of serine proteases. For example, it has been found that certain selections for the groups "Z—L—" in formula I, provide compounds which are particularly selective for inhibition of one or more serine proteases versus other proteases. To illustrate, it has been surprisingly found that when Z—L— is selected from:

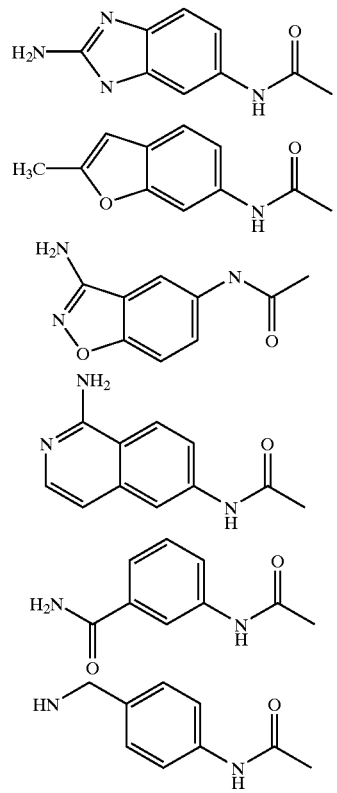

-continued

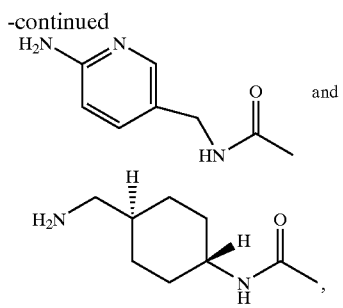

compounds of formula I are particularly selective for inhibition of FVIIa.

As another illustration, it has been found that when Z—L— is

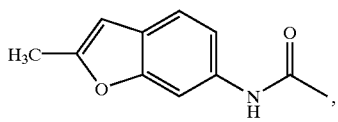

compounds of formula I are particularly selective for inhibition of FXa.

Included within the scope of the invention are pharmaceutical compositions for treating a serine protease disease, an inflammatory or immune condition, or cancer, comprising at least one compound of formula I or a pharmaceutically acceptable salt, hydrate or prodrug thereof, and a pharmaceutically acceptable carrier or diluent. Also included in the invention are methods of treating such diseases comprising administering to a mammal in need of such treatment at least one compound of formula I or a pharmaceutically acceptable salt, hydrate or prodrug thereof. Further included in the invention are compositions for use as anticoagulants during the preparation, use, storage, or fractionation of blood and methods of maintaining blood in the fluid phase during its preparation, use, storage, or fractionation.

DETAILED DESCRIPTION OF THE INVENTION

The following are definitions of terms used in this specification. The initial definition provided for a group or term herein applies to that group or term throughout this specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, alkenyl, alkynyl, nitro, cyano, hydroxy, alkoxy, alkylthio, —$CO_2H$, —$C(=O)H$, —$CO_2$-alkyl, —$C(=O)$alkyl, —$S(O)_2$(alkyl), keto (=O), aryl, heteroaryl, heterocyclo, and cycloalkyl, including phenyl, benzyl, phenylethyl, phenyloxy, and phenylthio. The substituents for "substituted alkyl" groups may also be selected from the group consisting of —NR'R", —C(=O)NR'R", —$CO_2$NR'R", —NR'$CO_2$'R", —NR'C(=O)R", —$SO_2$NR'R", and —NR'$SO_2$'R", wherein each of R' and R" is independently selected from hydrogen, alkyl, cycloalkyl, and alkyl substituted with one to two of alkenyl, halogen, haloalkyl, haloalkoxy, cyano, nitro, hydroxy, alkoxy, alkylthio, amino, alkylamino, phenyl, benzyl, phenyloxy, and benzyloxy. Alternatively, R' and R" may together form a heterocyclo or heteroaryl ring. When a substituted alkyl includes an aryl, heterocyclo, cycloalkyl, or heteroaryl substituent, said ringed systems are as defined below and thus may have zero, one, two, or three substituents, also as defined below.

When the term "alkyl" is used in conjunction with another group, e.g., arylalkyl, hydroxyalkyl, etc., the term defines with more specificity a particular substituent that a substituted alkyl will contain. For example, arylalkyl refers to a substituted alkyl group having from 1 to 12 carbon atoms and at least one aryl substituent, and "lower arylalkyl" refers to substituted alkyl groups having 1 to 4 carbon atoms and at least one aryl substituent.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to three substitutents as defined above for alkyl groups. A ringed substituent of an alkyl, alkenyl, alkynyl, alkylene, alkenylene, or alkynylene may be joined at a terminal atom or an available intermediate (branch or chain) atom and thus may comprise, for example, the groups

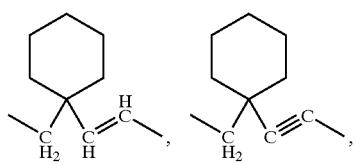

and so forth.

The term "alkoxy" refers to an alkyl group as defined above having one, two or three oxygen atoms (—O—) in the alkyl chain. For example, the term "alkoxy" includes the groups —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, O—$C_{1-4}$alkylene-O—$C_{1-4}$alkylene-O—$C_{1-4}$alkyl, and so forth.

The term "alkylthio" refers to an alkyl group as defined above bonded through one or more sulfur (—S—) atoms. For example, the term "alkylthio" includes the groups —S—$C_{1-12}$alkyl, —$S_{1-6}$alkylene-S—$C_{1-6}$alkyl, etc.

The term "alkylamino" refers to an alkyl group as defined above bonded through one or more nitrogen (—NR—) groups. The term alkylamino refers to straight and branched chain groups and thus, for example, includes the groups —NH($C_{1-12}$alkyl) and —N($C_{1-6}$alkyl)$_2$.

When a subscript is used with reference to an alkoxy, alkylthio or alkylamino, the subscript refers to the number of carbon atoms in the group in addition to heteroatoms. Thus, for example, monovalent $C_{1-2}$alkylamino includes the groups —NH—$CH_3$, —NH—$CH_2$—$CH_3$, and —N—($CH_3$)$_2$. A lower alkylamino comprises an alkylamino having from one to four carbon atoms.

When reference is made to a substituted alkoxy or alkylthio, the carbon atoms of said groups are substituted with one to three substituents as defined above for alkyl groups. When reference is made to a substituted alkylamino, the carbon and/or nitrogen atoms of these groups are substituted with one to three substitutents appropriately selected from the group of substituents recited above for alkyl groups. Additionally, the alkoxy, alkylthio, or alkylamino groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—$C_{1-12}$alkyl and —$C_{1-6}$alkylene-O—$C_{1-6}$alkyl, whereas a bivalent alkoxy includes groups such as —O—$C_{1-12}$alkylene- and —$C_{1-6}$alkylene-O—$C_{1-6}$alkylene-, etc.

The term "heteroalkyl" is used herein to refer saturated and unsaturated straight or branched chain hydrocarbon groups having 2 to 12 carbon atoms, preferably 2 to 8 carbon atoms, wherein one, two or three carbon atoms in the straight chain are replaced by a heteroatom (O, S or N). Thus, the term "heteroalkyl" includes alkoxy, alkylthio, and alkylamino groups, as defined above, as well as alkyl groups having a combination of heteroatoms selected from O, S, or N. A "heteroalkyl" herein may be monovalent or bivalent, and for example, may comprise the groups —O—($CH_2$)$_{2-5}$NH—($CH_2$)$_2$— or —O—($CH_2$)$_{2-5}$NH—$CH_3$, etc. A "substituted heteroalkyl" has to three substituents appropriately selected from those recited above for alkyl groups.

The term "acyl" refers to a carbonyl group

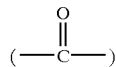

linked to an organic radical including an alkyl, alkenyl, alkynyl, substituted alkyl, substituted alkenyl, or substituted alkynyl group, as defined above.

The term "alkoxycarbonyl" refers to a carboxy or ester group

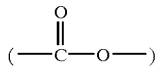

linked to an organic radical including an alkyl, alkenyl, alkynyl, substituted alkyl, substituted alkenyl, or substituted alkynyl group, as defined above.

The term "halo" or "halogen" refers to chloro, bromo, fluoro and iodo.

The term "haloalkyl" means an alkyl having one or more halo substituents, e.g., including trifluoromethyl.

The term "haloalkoxy" means an alkoxy group having one or more halo substituents. For example, "haloalkoxy" includes —$OCF_3$.

The term "sulfonyl" refers to a sulphoxide group (i.e., —$S(O)_{1-2}$—) linked to an organic radical including an alkyl, alkenyl, alkynyl, substituted alkyl, substituted alkenyl, or substituted alkynyl group, as defined above. The organic radical to which the sulphoxide group is attached may be monovalent (e.g., —$SO_2$-alkyl), or bivalent (e.g., —$SO_2$-alkylene, etc.)

The term "sulfonamide" refers to the group —S(O)$_2$NR'R", wherein R' and R" may be hydrogen or alkyl, alkenyl, alkynyl, substituted alkyl, substituted alkenyl, or substituted alkynyl, as defined above. R' and R" may be monovalent or bivalent (e.g., —$SO_2$—NH-alkylene, etc.)

The term "aryl" refers to phenyl, biphenyl, 1-naphthyl and 2-naphthyl, with phenyl being preferred. The term "aryl" includes such rings having zero, one, two or three substituents selected from the group consisting of halo, alkyl, alkenyl, alkynyl, nitro, cyano, hydroxy, alkoxy, alkylthio, —$CO_2$H, —C(=O)H, $CO_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —$CO_2$NR'R", —NR'$CO_2$'R", —NR'C(=O)R", —$SO_2$NR'R", —NR'$SO_2$'R", and/or alkyl substituted with one to three of halo, nitro, cyano, hydroxy, alkoxy, alkylthio, —$CO_2$H, —C(=O)H, $CO_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —$CO_2$NR'R", —NR'$CO_2$'R", —NR'C(=O)R", —$SO_2$NR'R", and/or —NR'$SO_2$'R", wherein each of R' and R" is independently selected from hydrogen, alkyl, alkoxy, hydroxyalkyl, and arylalkyl, or R' and R" together form a heterocyclo or heteroaryl ring. When an aryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents, preferably zero or one, selected from the group consisting of halo, alkyl, alkenyl, alkynyl, nitro, cyano, oxo (=O), hydroxy, alkoxy, alkylthio, —$CO_2$H, —C(=O)H, $CO_2$-alkyl, —C(=O)alkyl, keto, =N—OH, =N—O-alkyl, heteroaryl, heterocyclo, a five or six membered ketal (i.e. 1,3-dioxolane or 1,3-dioxane), a four to seven membered carbocyclic ring, —NR'R", —C(=O)NR'R", —$CO_2$NR'R", —NR'$CO_2$'R", —NR'C(=O)R", —$SO_2$NR'R", —NR'$SO_2$'R", and/or alkyl substituted with one to three of halo, nitro, cyano, hydroxy, alkoxy, alkylthio, —$CO_2$H, —C(=O)H, $CO_2$-alkyl, —C(=O)alkyl, phenyl, benzyl, phenylethyl, phenyloxy, phenylthio, a four to seven membered carbocyclic ring, heterocyclo, heteroaryl, —NR'R", —C(=O)NR'R", —$CO_2$NR'R", —NR'$CO_2$'R", —NR'C(=O)R", —$SO_2$NR'R", and/or —NR'$SO_2$'R", wherein each of R' and R" is independently selected from hydrogen, alkyl, alkoxy, hydroxyalkyl, and arylalkyl, or R' and R" together form a heterocyclo or heteroaryl ring. When a cycloalkyl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, alkenyl, alkynyl, nitro, cyano, oxo, hydroxy, alkoxy, alkylthio, —CO$_2$H, —C(=O)H, CO$_2$-alkyl, —C(=O)alkyl, keto, =N—OH, =N—O-alkyl, aryl, heteroaryl, cycloalkyl, a five or six membered ketal (i.e. 1,3-dioxolane or 1,3-dioxane), —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a heterocyclo is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, alkenyl, alkynyl, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, a further monocyclic heteroaryl, —NR'R", —C(=O)NR'R", —CO$_2$NR'R", —NR'CO$_2$'R", —NR'C(=O)R", —SO$_2$NR'R", —NR'SO$_2$'R", and/or alkyl substituted with one to three of halo, nitro, cyano, hydroxy, alkoxy, alkylthio, —CO$_2$H, —C(=O)H, CO$_2$-alkyl, —C(=O)alkyl, phenyl, benzyl, phenylethyl, phenyloxy, phenylthio, cycloalkyl, heterocyclo, heteroaryl, —NR'R", —C(=O)NR'R", —CO$_2$NR'R", —NR'CO$_2$'R", —NR'C(=O)R", —SO$_2$NR'R", and/or —NR'SO$_2$'R", wherein each of R' and R" is independently selected from hydrogen, alkyl, alkoxy, hydroxyalkyl, and arylalkyl, or R' and R" together form a heterocyclo or heteroaryl ring. When a heteroaryl is substituted with a further ring, said ring may in turn be substituted with one to three of halogen, haloalkyl, haloalkoxy, cyano, nitro, hydroxy, alkoxy, alkylthio, amino, alkylamino, phenyl, benzyl, phenyloxy, and benzyloxy.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "carbocyclic" refers to optionally substituted aromatic or non-aromatic 3 to 7 membered monocyclic and 7 to 11 membered bicyclic groups, in which all atoms of the ring or rings are carbon atoms.

When the term "unsaturated" is used herein to refer to a ring or group, the ring or group may be fully unsaturated or partially unsaturated.

The term "metal ion" refers to alkali metal ions such as sodium, potassium or lithium and alkaline earth metal ions such as magnesium and calcium, as well as zinc and aluminum.

Whenever a bond appears in a formula as a dashed-double bond, i.e., with one bond appearing as a dash as in

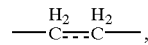

it should be understood that such bonds may be selected from single or double bonds, as appropriate given the selections for adjacent atoms and bonds. For example, in formula I, above, when X$_2$ is N or CH, the bonds linking R$_1$ to X$_2$ and X$_2$ to C$_6$ are single bonds; and when X$_2$ is C, one of the bonds linking X$_2$ to an adjacent atom is a double bond, i.e., either a bond to R$_1$ or to C$_6$ is a double bond.

It should be understood that one skilled in the field may make various substitutions for each of the groups recited in the claims herein, without departing from the spirit or scope of the invention. For example, one skilled in the field may replace a W group recited in the claims with a cyano, halogen, or methyl group. The linker group "L" recited in the claims may be replaced with the group —(R')$_u$—Y'—(R")$_v$— wherein Y' is a Y group recited in claim 1, is a bond, or is selected from —C(=O)—, —[C(=O)]$_2$—, —O—, —NR—, —C(=NR)—, —S(O)$_{1-2}$—, —NRC(=O)NR—, —NRSO$_2$—, or —SO$_2$NR—, wherein R is selected from hydrogen, alkyl, substituted alkyl, alkenyl, substituted alkenyl, a heterocyclo or carbocyclic ring, and so forth, R' and R" may comprise substituted or unsubstituted alkylene, alkenylene, or alkynylene, and u and v may be 0–4. Additionally, the acid group —CO$_2$R$_3$ may be joined to the phenyl or pyridyl ring B with a linker such as a methylene group or replaced with other acid functional groups such as —SO₃H, —P(=O)(OR)₂, —SO₂NHC(=O)R, —C(=O)NHSO₂R, —C(=O)NHOH, —[C(=O)]₂OR, or tetrazole, wherein R is hydrogen, alkyl, substituted alkyl, cycloalkyl, and so forth.

It should be further understood that for compounds of formula I, the linker group "L" is inserted into the formula I in the same direction set forth in the text. Thus, for example, if L is recited as —CH₂—Y—, this means the —CH₂— group is attached to Z, and the Y group is attached to the C₆ carbon atom i.e., to which X₂ is attached, as in:

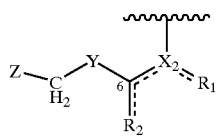

Likewise, when Y is recited as —NR₁₃C(=O)—, the carbonyl group C(=O) is attached to the C₆ carbon atom and the nitrogen group —NR₁₃— is attached to Z, as in many Examples herein. Conversely, when Y is recited as —(CO)NR₁₃—, this means the carbonyl group C(=O) is attached to Z and the nitrogen group —NR₁₃— is attached to the C₆ carbon atom.

Throughout the specification, groups and substituents thereof may be chosen by one skilled in the field to provide stable moieties and compounds.

The compounds of formula I form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., nontoxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Various forms of prodrugs are well known in the art. For examples of such prodrug derivatives, see:

a) *Design of Prodrugs,* edited by H. Bundgaard, (Elsevier, 1985) and *Methods in Enzymology,* Vol.42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews,* 8, 1–38 (1992), each of which is incorporated herein by reference.

Compounds containing a carboxy group can form physiologically hydrolyzable esters which serve as prodrugs by being hydrolyzed in the body to yield formula I compounds per se. For example, in compounds of formula (I), prodrugs comprise compounds wherein the upper ring substituent —CO₂R₃ is a group that will hydrolyze in the body to compounds where said substituent is —CO₂H. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C₁₋₆alkylbenzyl, 4-methoxybenzyl, indanyl, phthalyl, methoxymethyl, C₁₋₆alkanoyloxy-C₁₋₆alkyl, e.g. acetoxymethyl, pivaloyloxymethyl or propionyloxymethyl, C₁₋₆alkoxycarbonyloxy-C₁₋₆alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

The compounds of the instant invention may, for example, be in the free or hydrate form, and may be obtained by methods exemplified by the following descriptions.

Preferred Compounds

Preferred compounds are those having the formula (I),

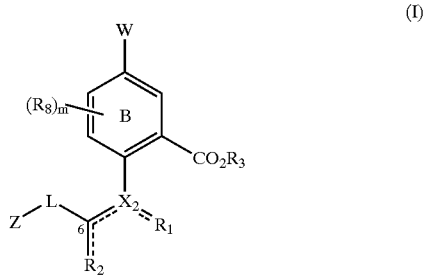

and pharmaceutically-acceptable salts, prodrugs, or solvates thereof, in which:

W is selected from $-C(=O)NR_4R_5$, $-OR_6$, optionally-substituted heterocycle, substituted alkyl, alkenyl, and substituted alkenyl;

ring B is phenyl;

$X_2$ is N, CH, or C, provided that $X_2$ is C when $R_1$ and $R_2$ join to form a fully unsaturated ring;

L is $-(CH_2)_s-Y-$;

Y is selected from $-C(=O)$, $-NH-C(=O)-$, $-NH-CH_2-$, and $-CH_2-CH_2-$;

Z is selected from

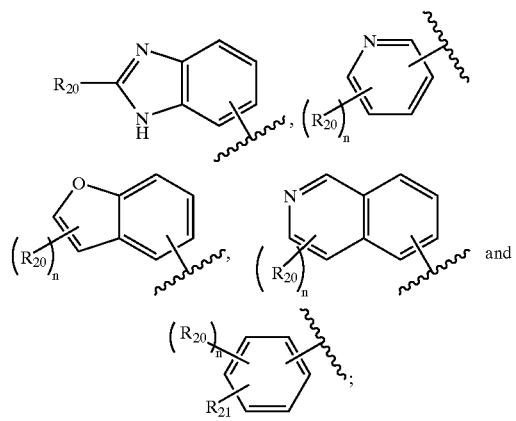

$R_1$ and $R_2$ (i) are independently selected from hydrogen, lower alkyl, aryl and arylalkyl; or (ii) are taken together to form an aryl, heteroaryl, cycloalkyl, or heterocyclo; wherein when $R_1$ and $R_2$ individually or together form a heteroaryl, aryl, heterocyclo or cycloalkyl, said cyclic group is optionally substituted with up to two $R_{26}$;

$R_3$ is hydrogen, alkyl, substituted alkyl, or alkyl substituted with $-OC(=O)R_{24}$ or $-OC(=O)OR_{24}$, wherein $R_{24}$ is alkyl, substituted alkyl, or cycloalkyl;

$R_4$ is hydrogen or lower alkyl;

$R_5$ is hydrogen, alkyl, substituted alkyl, alkenyl, substituted alkenyl, heterocyclo or heteroaryl;

$R_6$ is selected from $C_{1-6}$alkyl, more preferably $C_{2-6}$alkyl, phenyl, and benzyl;

$R_8$ and $R_{26}$ (i) are at each occurrence independently selected from hydrogen, $OR_{30}$, $NR_{31}R_{32}$, alkyl, alkenyl, substituted alkyl, substituted alkenyl, halogen, haloalkyl, haloalkoxy, cyano, nitro, alkylthio, $-C(=O)H$, acyl, $-CO_2H$, alkoxycarbonyl, sulfonamido, sulfonyl, and phenyl, or (ii) two of $R_8$ and/or two of $R_{26}$ may be taken together to form a fused benzo ring, a fused heteroaryl, or a fused heterocyclo other than a five or six membered heterocyclo having as its heteroatoms two oxygen atoms, provided further that when two $R_{26}$ form a fused benzo ring, then Z is not phenyl substituted in the para position with cyano or a five-membered heterocycle or heteroaryl;

$R_{20}$ and $R_{21}$ are independently selected from hydrogen, halogen, $-C(=O)NH_2$, $-C(=O)C_{1-4}$alkyl, $-NH_2$, $-NHC_{1-4}$alkyl, $-S-C_{1-4}$alkyl, $-O-C_{1-4}$alkyl, $C_{1-4}$alkyl, $C_{1-4}$alkyl substituted with $NH_2$, and five or six membered heterocyclo or heteroaryl;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl, and cycloalkyl;

m and n are independently 0, 1 or 2; and s is 0, 1 or 2.

In compounds of formula I, the group W is preferably $-C(=O)NR_4R_5$ and the groups Z—L— taken together are preferably selected from:

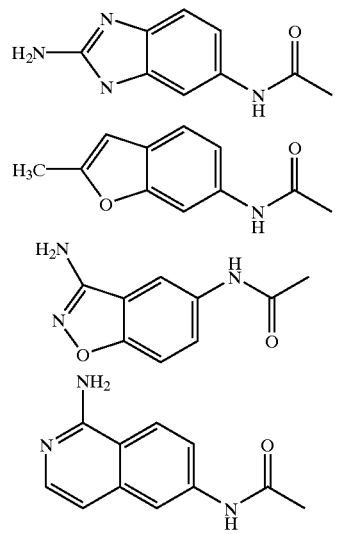

-continued

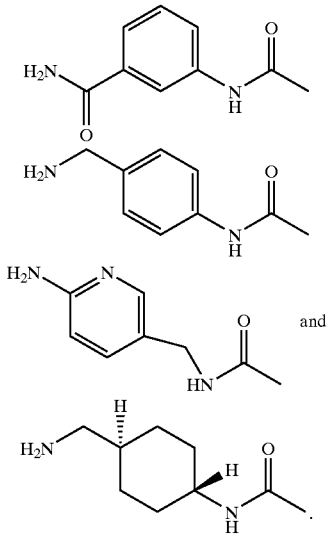

More preferred compounds are those compounds having the formulae:

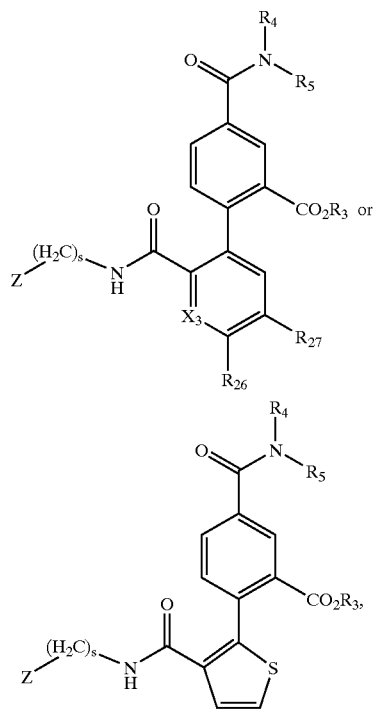

in which:

$X_3$ is CH or N;

$R_3$ is hydrogen, lower alkyl, or lower alkyl substituted with one of OC(=O)$R_{24}$ and OC(=O)O—$R_{24}$, wherein $R_{24}$ is alkyl or cycloalkyl;

$R_4$ is hydrogen or lower alkyl;

$R_5$ is $C_{1-6}$alkyl, —CH(CH$_2$OH)C(CH$_3$)$_3$, or $C_{1-2}$alkyl substituted with $C_{5-6}$cycloalkylene;

either (a) s is 0 and Z is selected from

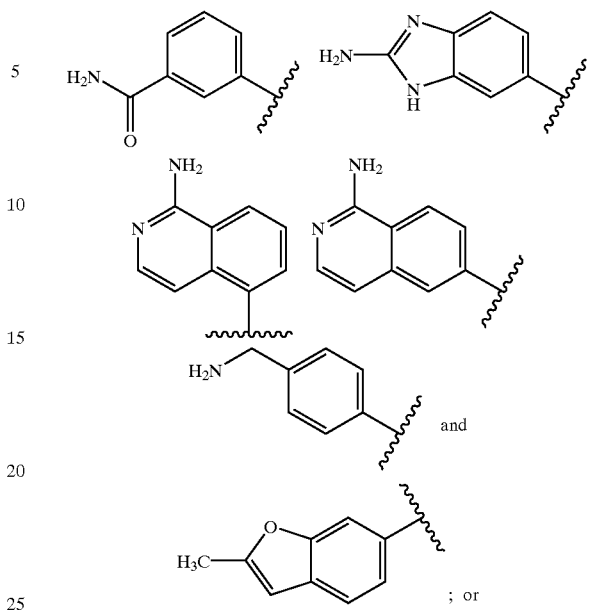

(b) s is 1 and Z is selected from

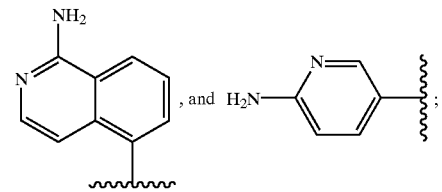

$R_{26}$ is $C_{2-6}$straight or branched alkenyl, —OR$_{30}$ or —NR$_{31}$R$_{32}$, and $R_{27}$ is hydrogen, or $R_{26}$ and $R_{27}$ together form a fused benzo ring;

$R_{30}$ is $C_{1-5}$ straight or branched chain alkyl, $C_{2-6}$straight or branched alkenyl, $C_{3-5}$cycloalkyl, or $C_{1-4}$ straight or branched chain alkyl substituted with one to two of halogen, lower alkoxy, and $C_{3-5}$cycloalkyl;

$R_{31}$ and $R_{32}$ are selected from hydrogen and lower alkyl.

Most preferred are compounds having the formula:

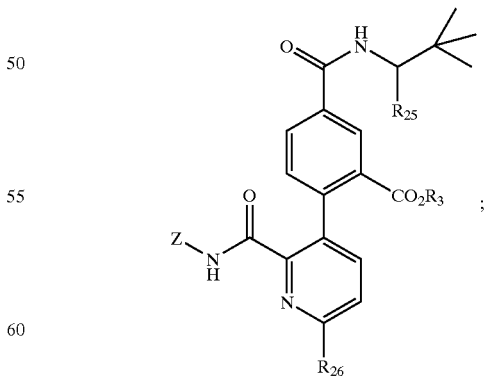

in which $R_3$ is hydrogen, lower alkyl, or lower alkyl substituted with —OC(=O)$R_{24}$ or —OC(=O)O$R_{24}$, wherein $R_{24}$ is alkyl or cycloalkyl;

Z is selected from:

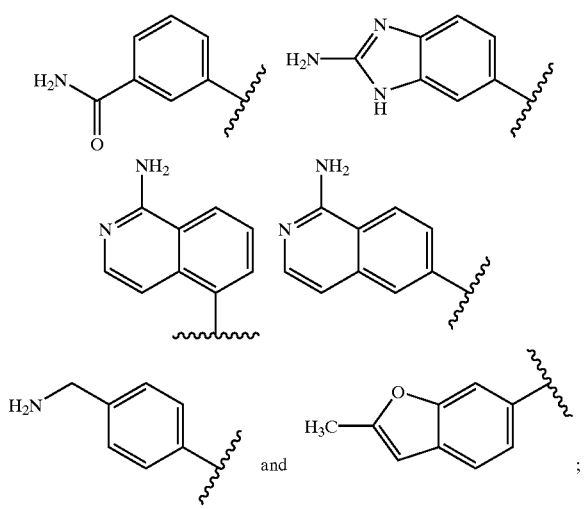

and $R_{25}$ is hydrogen or hydroxymethyl; and
$R_{26}$ is $C_{1-3}$alkoxy or $NH(C_{1-4}alkyl)$.

Methods of Preparation

The compounds of the invention may be prepared by the exemplary processes described in the following Schemes A through D. Methods for making intermediates including appropriately-protected amine-coupling components are shown in Schemes E through G and I through X, and Scheme H shows a method for making an unprotected amine-coupling component. These amines may be coupled to substrates to make compounds of formula I and deprotected, when necessary or desired, as shown in Schemes A–D and the Examples. Exemplary reagents and procedures for these reactions appear hereinafter and in the working Examples. Starting materials are commercially available or can be readily prepared by one of ordinary skill in the art as shown herein or as described in the literature. For all of the schemes, the groups $R_1$–$R_{27}$, W, X, Z, r, s etc., are as described herein for a compound of formula I, unless otherwise indicated.

SCHEME A

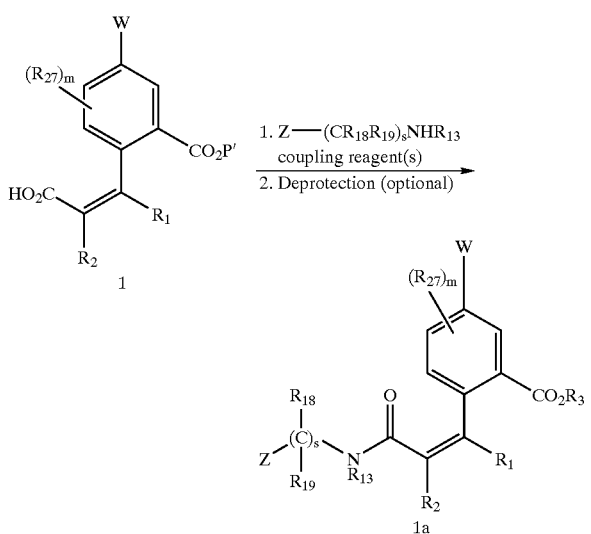

Compounds of formula Ia can be made by reacting acid 1 with an amine having the desired group Z, i.e., Z—$NHR_{13}$. The 2-position acid group is suitably protected (P'), and the reaction is carried out in the presence of coupling reagent(s) such as DCC/HOBT/DMAP, EDC/DMAP, or DIC/HOAT to afford the corresponding amide compound. The group P' optionally may be deprotected to afford the compound of formula Ia wherein $R_3$ is hydrogen, or the group P' may be retained wherein P' comprises the desired group $R_3$. Alternatively, the group P' may be deprotected to afford the group $CO_2H$, with the group $CO_2H$ then converted to another desired $R_3$ group. To illustrate, the compound having the acid group $CO_2H$ may be reacted with a halide having the desired $R_3$ group, i.e., X—$R_3$ where X is Cl, Br, or I, in the presence of base, or the acid compound may be coupled with an alcohol such as $R_3OH$ in a coupling reagent. It may be necessary or desired to protect additional functional groups besides the 2-position acid before performing the coupling reaction, as one skilled in the field will appreciate. Those additional protecting groups can be removed after the coupling using appropriate deprotecting conditions. Preparation of acids 1, wherein $R_1$ and $R_2$ together form an unsaturated carbocyclic or heterocyclic ring, is described in WO 99/041231, incorporated herein by reference, and described in the Examples that appear hereinafter.

SCHEME B

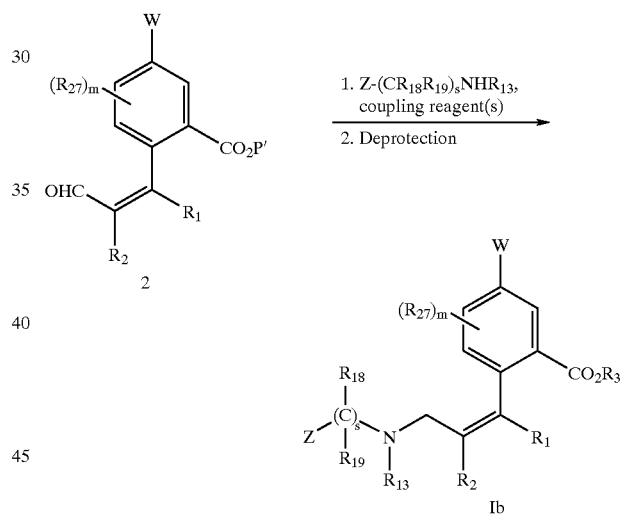

Similar to Scheme A, the aldehyde 2, wherein the 2-position acid group is suitably protected (P'), can be coupled with an amine Z—$NHR_{13}$ in the presence of a reducing reagent such as sodium triacetoxyborohydride, to afford the corresponding amine compound having the group $CO_2P'$. Upon optional deprotection of the group P', and optionally further reaction with, for example, a halide X—$R_3$ or alcohol $R_3OH$ as described in Scheme A, the compound of formula Ib is provided, having the desired group $R_3$. Also as in Scheme A, it may be necessary or desired to protect additional functional groups besides the 2-position acid before performing the coupling reaction. Those additional protecting groups can be removed using appropriate deprotecting conditions. Preparation of aldehydes 2, wherein $R_1$ and $R_2$ together form an unsaturated carbocyclic or heterocyclic ring, is described in WO 99/041231, incorporated herein, and further shown in the Examples hereinafter.

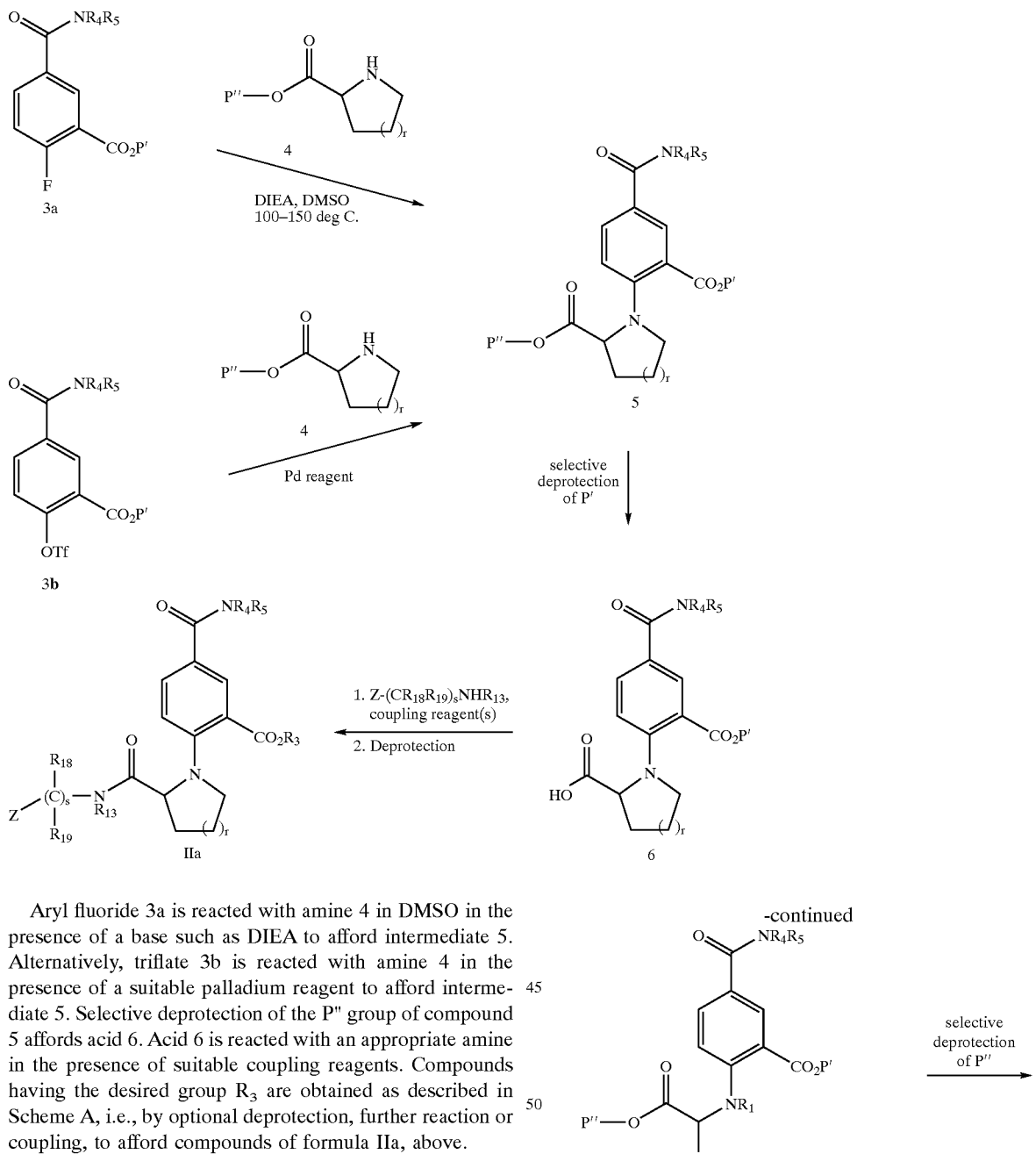

Aryl fluoride 3a is reacted with amine 4 in DMSO in the presence of a base such as DIEA to afford intermediate 5. Alternatively, triflate 3b is reacted with amine 4 in the presence of a suitable palladium reagent to afford intermediate 5. Selective deprotection of the P'' group of compound 5 affords acid 6. Acid 6 is reacted with an appropriate amine in the presence of suitable coupling reagents. Compounds having the desired group $R_3$ are obtained as described in Scheme A, i.e., by optional deprotection, further reaction or coupling, to afford compounds of formula IIa, above.

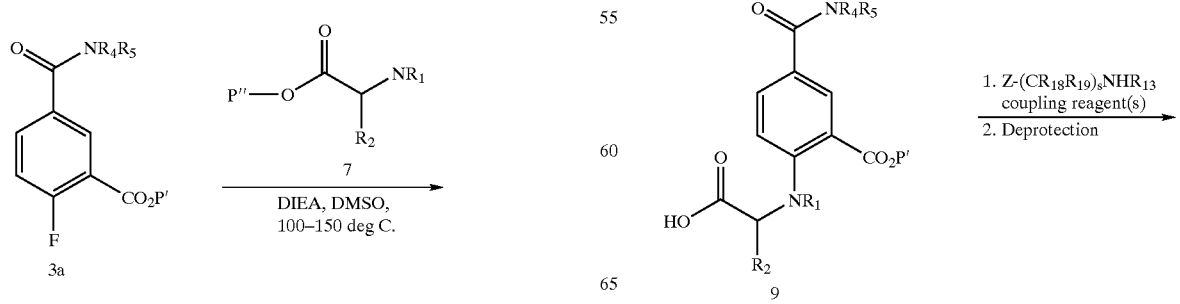

-continued

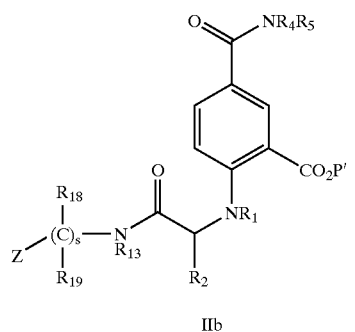

IIb

Aryl fluoride 3a is reacted with amine 7 in DMSO in the presence of a base such as DIEA to afford compound 8, where $R_1$ is defined as above except where $R_1$ and $R_2$ form a ring, the ring is a heterocyclo. Selective deprotection of the P" group affords acid 9. Reaction of acid 9 with an amine Z—$NHR_{13}$ in the presence of coupling reagent(s) such as DCC/HOBT/DMAP, EDC/DMAP, or DIC/HOAT affords the corresponding amide compound. Compounds having the desired group $R_3$ are obtained as described in Scheme A, i.e., by optional deprotection, further reaction or coupling, to afford compounds of formula IIb, above.

SCHEME E

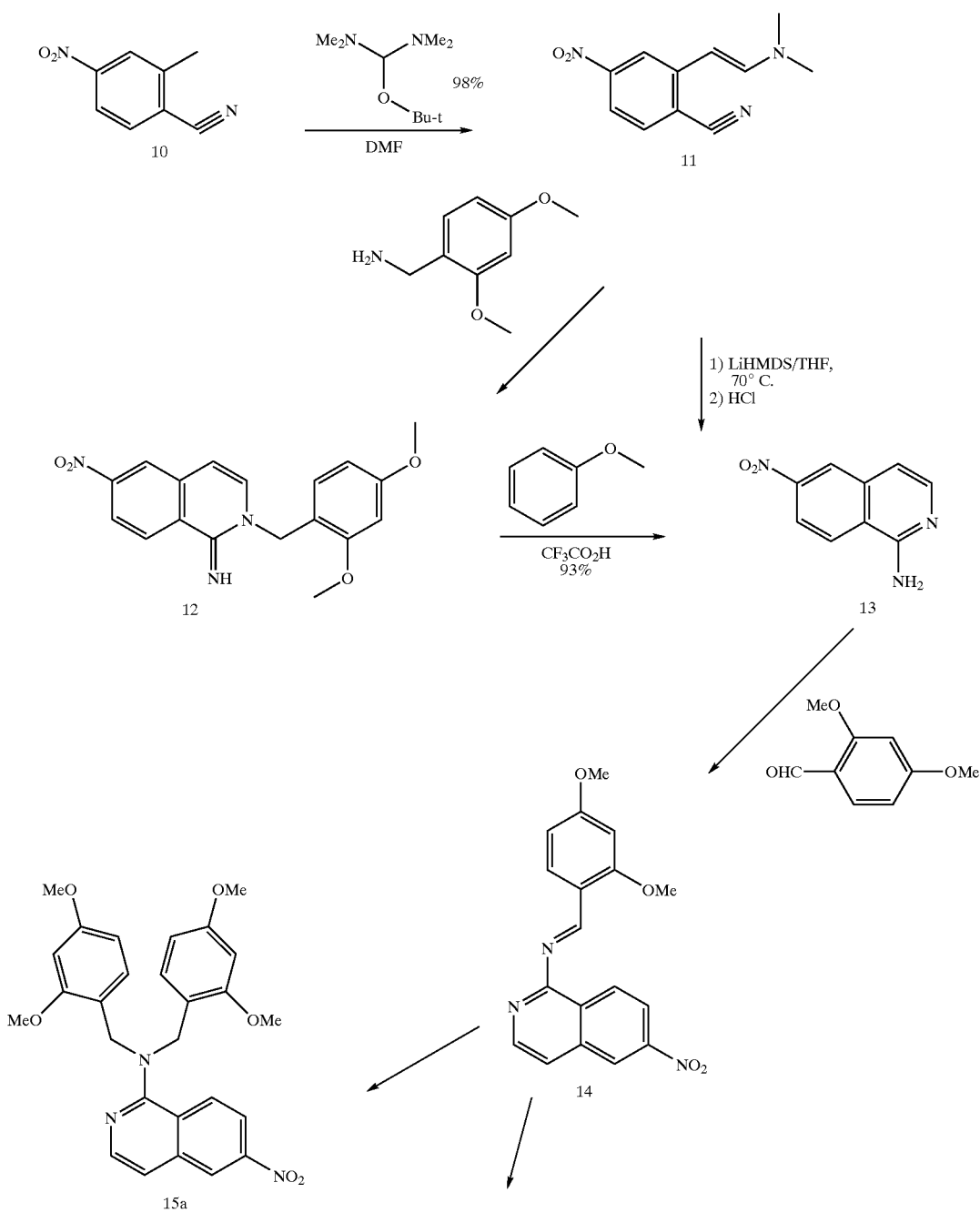

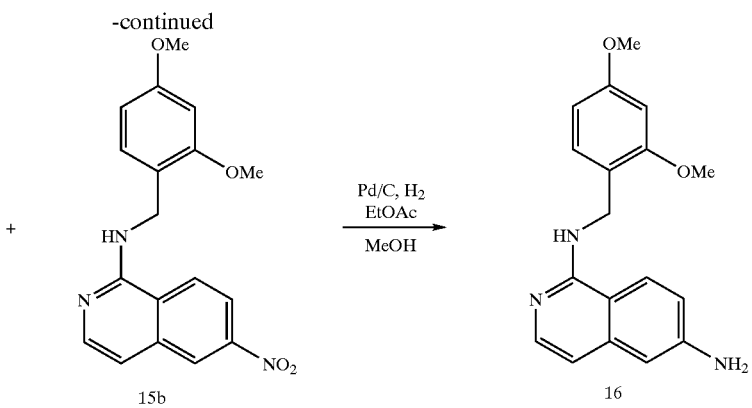

15b

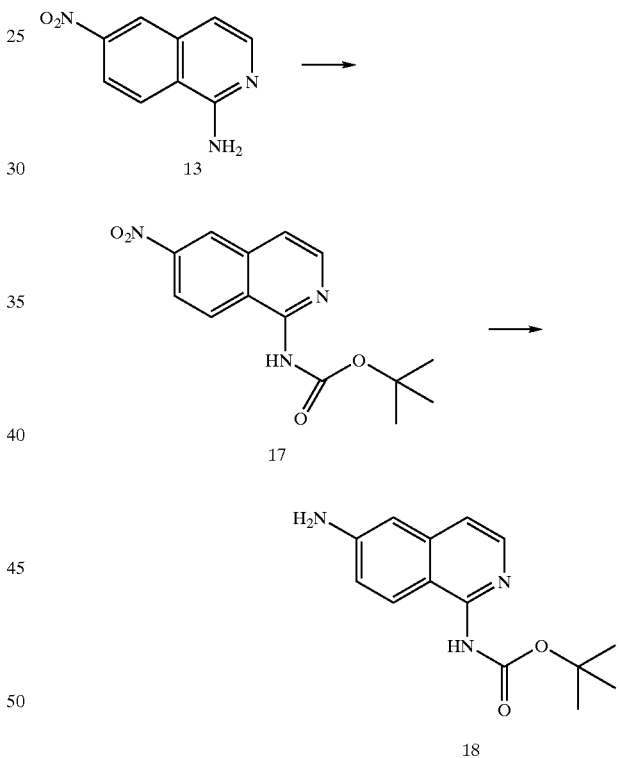

Compound 10 was prepared according to *J. Med. Chem.,* Vol. 42 (1999), at pp. 3510–3519, from 2-methyl-4-nitroaniline. A mixture of compound 10 and 1-(1,1-dimethylethoxy)-N,N,N',N'-tetramethyl-methanediamine in dry DMF (10 mL) was stirred at 70° C. for 2 h under $N_2$. After cooling to rt, the reaction mixture was treated with hexane, and the solid was collected by filtration and washed with hexane to give compound 11 as black crystals. Compound 11 was converted to compound 13 in two alternate ways.

In one approach, compound 11 was converted to 13 by adding 1N LiHMDS to a solution of 11 in dry THF under $N_2$. The reaction mixture was stirred at 65° C. for 2 h. After cooling to rt, 12 N HCl was added and the reaction mixture stirred at 50° C. for 1 h. After cooling to rt, the mixture was neutralized with sat'd $NaHCO_3$, the product extracted with EtOAc, and the organic layer washed with water and sat'd NaCl. The product was concentrated and purified to give compound 13 as a yellow solid.

Alternatively, compound 11 was converted to 13 by first mixing compound 11 and 2,4-dimethoxybenzylamine in DMF and stirring the mixture at 140° C. for 3 h. The solvent was removed by vacuum distillation and residue treated with EtOAc. The orange solid was collected by filtration and washed with hexane to give compound 12. To a solution of compound 12 in anisole was added TFA. The reaction mixture was stirred at 90° C. for 1 h and the solvent removed under reduced pressure. The residue was treated with sat'd $NaHCO_3$ (30 mL) and the product collected by filtration and washed with water to afford compound 13.

Compound 13 (366 mg, 1.93 mmol) and 2,4-dimethoxybenzaldehyde were heated for 16 h at 125–130° C. with a stream of nitrogen passing in and out of the reaction flask, and sampling of the reaction mixture at 80° C. indicated conversion to compound 14.

To a solution of 14 and 2,4-dimethoxybenzaldehyde above in THF was added sodium triacetoxyborohydride. The reaction was stirred for 22 h and additional sodium triacetoxyborohydride (1.23 g, 5.8 mmol) was added. After 40 h, the reaction was concentrated to an oil which was taken up in EtOAc, water, and dilute sodium bicarbonate. The EtOAc was washed with water (3×), dried (sodium sulfate), and concentrated to an oily residue, which was chromatographed to give 140 mg of compound 15a as a glassy residue and 228 mg of compound 15b as an amorphous solid.

Hydrogenation of compound 15b in EtOAc and MeOH in the presence 10% Pd/C for 1 h at one atmosphere afforded compound 16 as an amorphous solid. Compound 16 was coupled to a substrate and deprotected to produce compounds of formula I.

SCHEME F

A mixture of compound 13 and di-t-butyl dicarbonate in dry THF was refluxed under $N_2$ for 3 h. The mixture was concentrated and the residue purified by flash chromatography eluting with EtOAc/Hexane (1:3) to give compound 17 as a white solid. Compound 17 and Pd/C (10%) in MeOH/dioxane was hydrogenated (balloon with $H_2$) for 3.5 h. Filtration and concentration yielded 18 as a brown foam (59 mg, 83%), which was used in Examples hereinafter as a protected amine-coupling component to make compounds of formula I.

SCHEME G

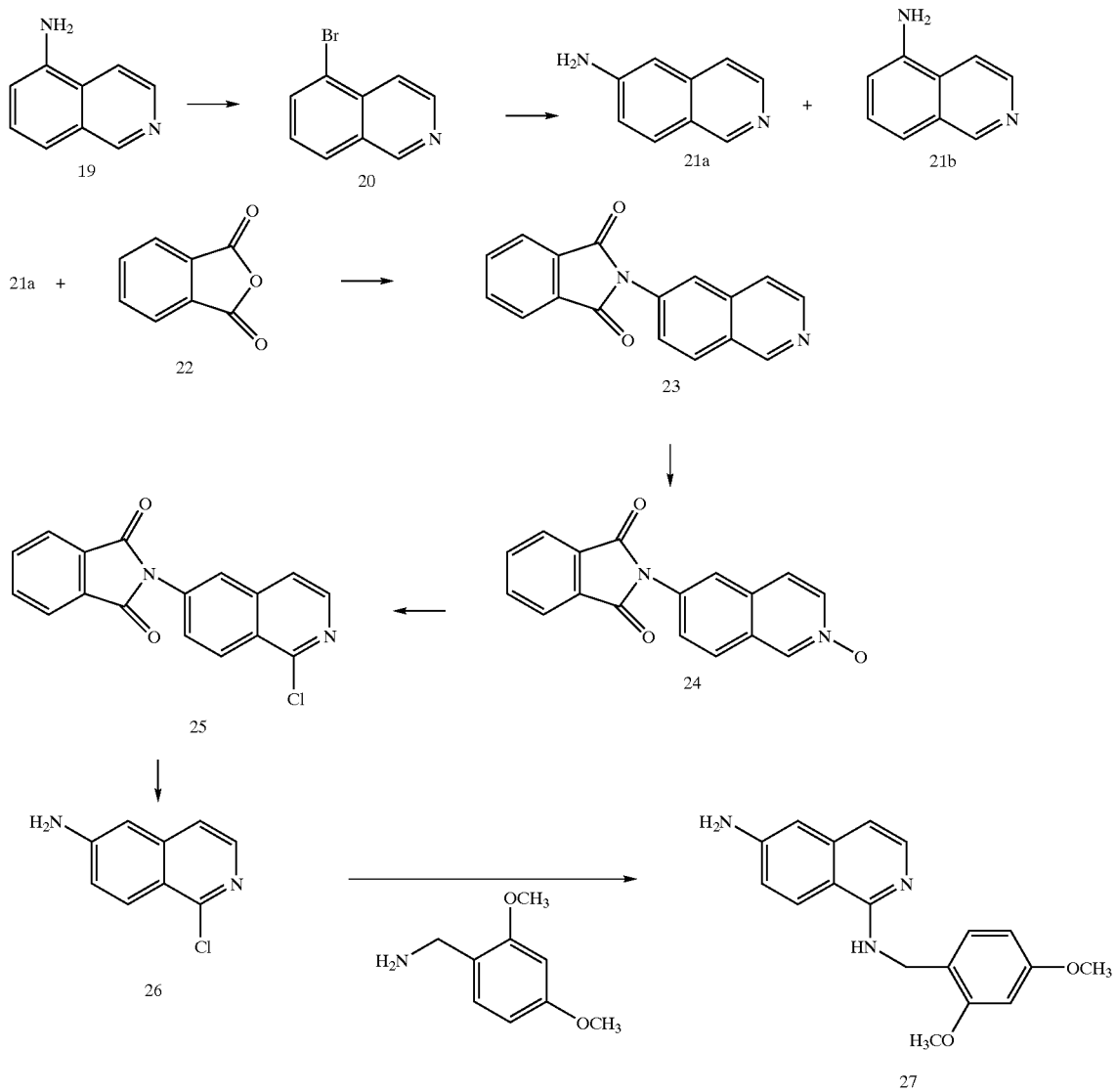

Compound 20 was synthesized from compound 19 following the procedure described in Osborn, et al., *J.Chem. Soc.* (1956), at 4191, and compounds 21a and 21b were prepared according to Poradowska et al., *Synthesis,* (1975), at p. 732. Compound 21a and phthalic acid anhydride 22 were powdered and mixed well. Heating the mixture for 2 h at 130 to 150° C. and finally 2 min to 220° C. finished the reaction. The cooled solid material of crude compound 23 was powdered and washed with ether/DCM (10:1) and dried yielding compound 23 as a beige powder.

Compound 23 and MCPA (Aldrich,~77%) were dissolved in DCE and stirred for 24 h. The resulting suspension was diluted with 50 ml ether and the crude product filtered, washed with ether, dried and purified to yield compound 24 as a light yellow powder. Compound 24 and $POCl_3$ were heated for 12 h to 90° C. Excess $POCl_3$ was removed in vacuo and the residue stirred with ice water/DCM for 10 min. The organic layer was dried over $Na_2SO_4$ and concentrated. The oily residue was purified to yield compound 25. $POCl_3$ was removed by dissolving the material in DCM and stirring with N -diisopropylaminomethyl polystyrol.

Filtration, concentration, and purification gave compound 25 as off-white needles.

Compound 25 and N-methylhydrazine were stirred in DCM to produce compound 26. Compound 26 and 2,4-dimethoxybenzylamine were heated to 110 to 120° C. and stirred to produce an oily crude material which was purified to give protected amine-coupling component 27 as a beige foam.

SCHEME H

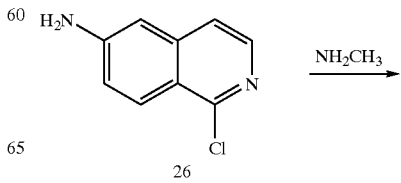

27

-continued

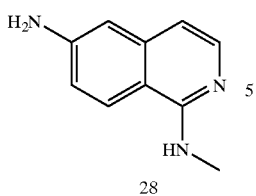

28

Compound 26 from Scheme G and condensed N-methylamine were heated to 100° C. for 24 h. Cooling, removal of the excess N-methylamine, and purification gave unprotected amine-coupling component 28 as an off-white solid.

SCHEME I

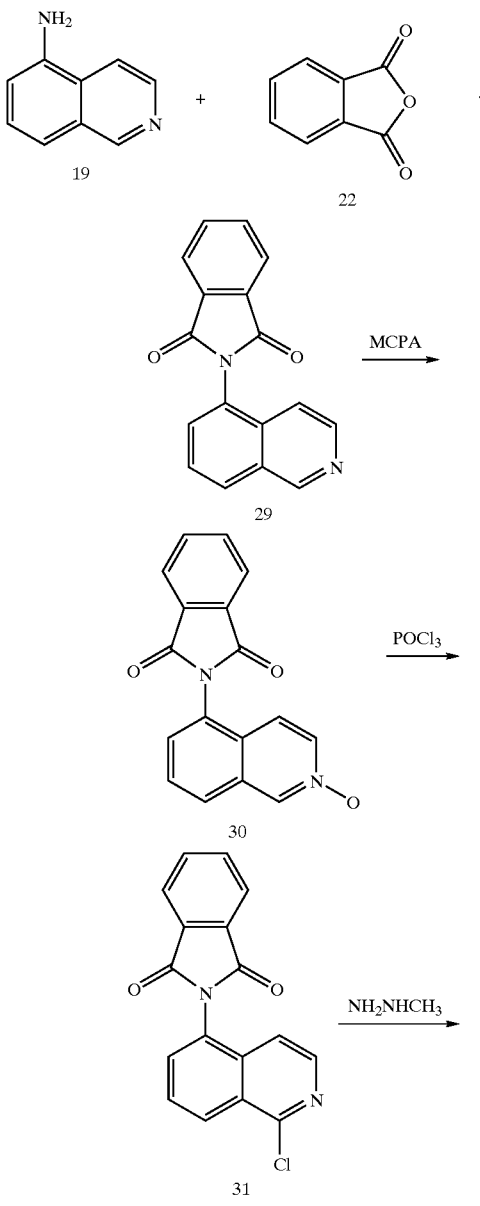

28

-continued

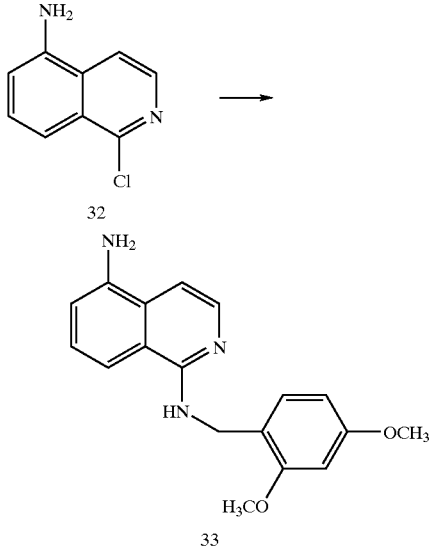

Following the procedure described in Scheme G, compound 29 was prepared from compound 19 and phthalic acid anhydride 22; compound 30 was prepared from compound 29 and MCPA; compound 31 was prepared from 30 and POCl₃; compound 32 was prepared from compound 31 and methylhydrazine; and protected amine-coupling component 33 was prepared from 32 and dimethoxybenzylamine.

SCHEME J

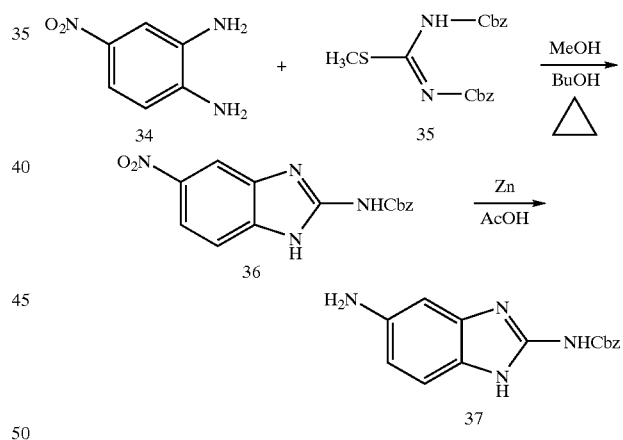

Compound 34 and bis-protected isothiourea 35 were suspended in MeOH and refluxed for 5 days. After the second day, n-BuOH was added and CH₃SH blown out with N₂. The reflux temperature was set to 100° C. After 3 more days refluxing, compound 36 crystallized and the reaction was completed. The mixture was cooled to 50° C., filtered, and the gray filter cake was washed with MeOH and recrystallized from DMF/MeOH to give compound 36 in the form of grey fine crystals.

Compound 36 was suspended in AcOH with stirring. Zn powder was added. After 1 hr, the reaction mixture was filtered, the filtrate concentrated, water was added, and then filtration, washing of the filter residue, and drying gave Cbz-protected amine coupling component 37 as a purple powder.

SCHEME K

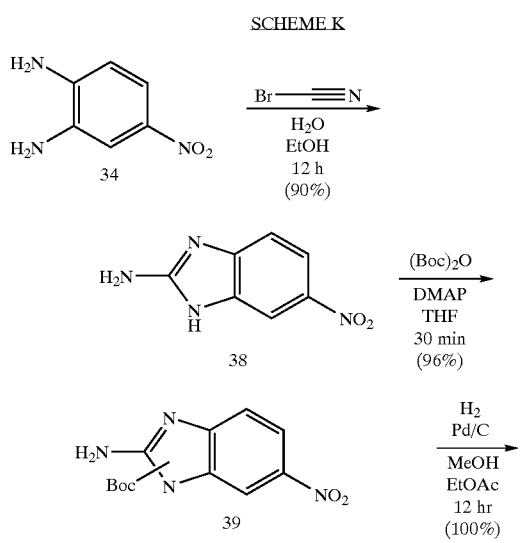
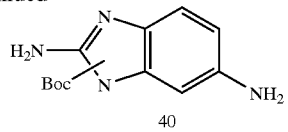

Cyanogen bromide was added to a flask charged with compound 34, water and EtOH. After 12 h, the reaction mixture was filtered, the filtrate was basified to pH=9 using conc. NH$_4$OH, the solution was conc. to one third volume, and H$_2$O was added. After 1 h at 4° C., the solid was filtered and dried under vacuum to give compound 38.

A solution of Boc anhydride in THF was added to a cold (0° C.) solution of compound 38 in THF (90 mL). DMAP was added, and the reaction mixture was stirred at rt. After 30 min, the solution was concentrated, the residue was dissolved in DCM, and then the solution was washed with 2% aq. NH$_4$Cl and sat. NaCl, dried (MgSO$_4$), and conc. to give compound 39.

MeOH and EtOAc (3:1) was added to compound 39. 10% Pd/C was added and a H$_2$ atmosphere introduced via balloon. After 12 h, the reaction mixture was filtered, the filtrate was conc., and the residue was placed under vacuum to give Boc-protected amine coupling component 40.

SCHEME L

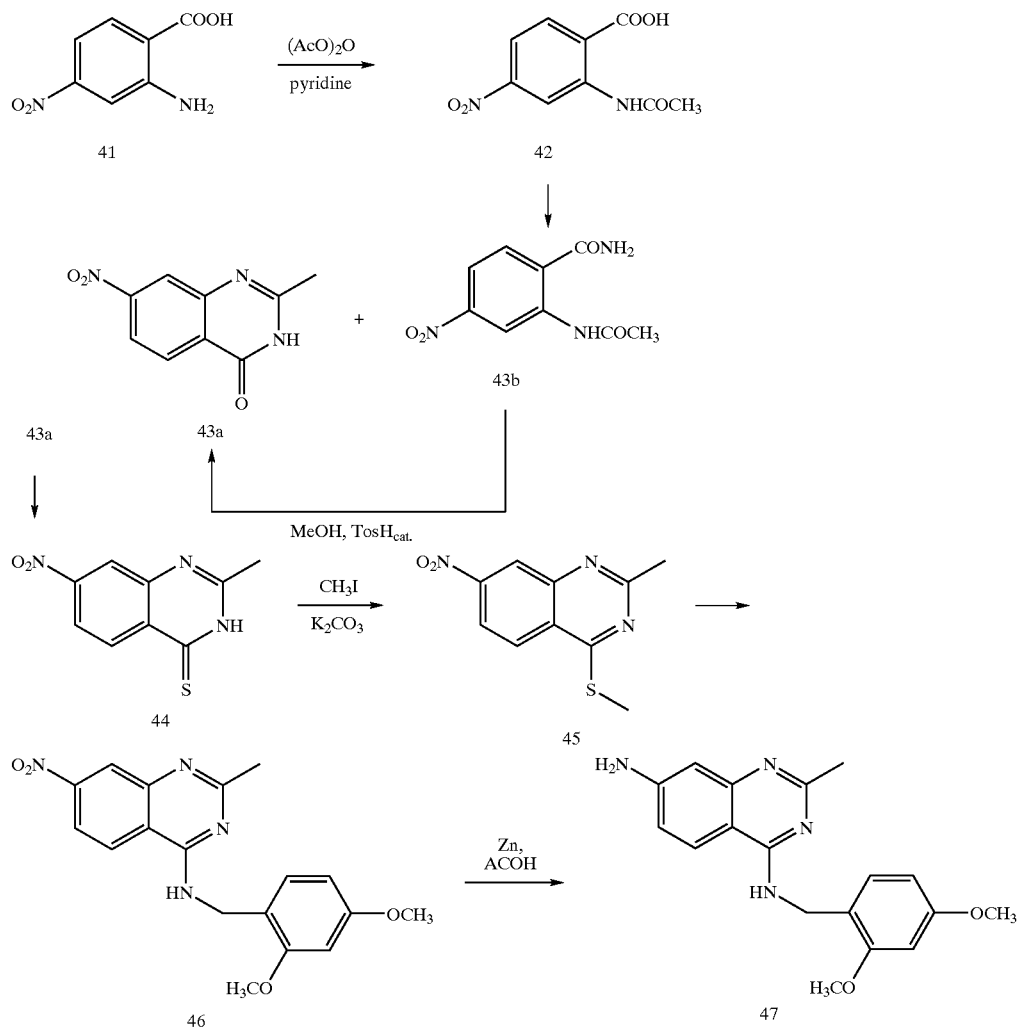

Compound 41 was dissolved in pyridine and while stirring, 2.55 g (25 mM) acetic acid anhydride was added over 15 min. Stirring continued for 24 h. The product was concentrated in vacuo and the resulting oil taken up with DCM/water. The pH was adjusted to 3.0 with citric acid. The phases were separated and the aqueous layer washed two more times with 50 ml DCM each time. The combined organic layer was washed with brine, dried (MgSO4), and concentrated to give compound 42.

Compound 42 and CDI were dissolved in 40 ml THF. After 30 min stirring, the solution was slowly added at 0° C. to 150 ml sat'd solution of $NH_3$ gas in THF. After stirring for 24 h at rt, the reaction mixture was filtered and the filtrate concentrated. The oily residue was dissolved in 30 ml MeOH from which after several minutes 43a crystallized. The mother liquor contained a mixture of 43a and 43b. Refluxing for 4 h in the presence of TosOH led to a complete cyclizsation of 43b to 43a.

Compound 43a and 760 mg (1.90 mM) Laweson reagent were suspended in 70 ml xylene and refluxed at 140° C. for 3 h. After cooling to rt, compound 44 crystallized out of the solution.

Compound 44 and 3 ml 1.0 N NaOH were dissolved in 15 ml DMF. To the stirred solution was added 166 ul (3.10 mM) $CH_3$. After 5 min, compound 45 crystallized, 50 ml water/EtOAc was added, and the aq. layer was extracted two times with 20 ml EtOAc. The combined organic phase was washed with brine, dried ($Na_2SO_4$), and the product 45 concentrated and purified.

Compound 45 and 2,4-dimethoxybenzylamine were dissolved in 10 ml toluene and refluxed for 2.5 h. After adding 30 ml ether to the cooled solution, filtration and drying, compound 46 was obtained as yellow crystals.

Compound 46 was dissolved in 10 ml AcOH and while stirring, 200 mg (3.06 mM) Zn powder was added. After 30 min, filtered from excess Zn, washed with 5 ml AcOH, and concentrated in vacuo yield an oily residue of crude 27 AcOH salt. This material was taken up with 20 ml water and the pH adjusted to 10 with $Na_2CO_3$ solution, followed by extraction 3 times with 15 ml EtOAc. The combined organic layer was washed with brine, dried ($Na_2SO_4$), and concentrated yielding protected amine-coupling component 47 in the form of a white foamy material.

SCHEME M

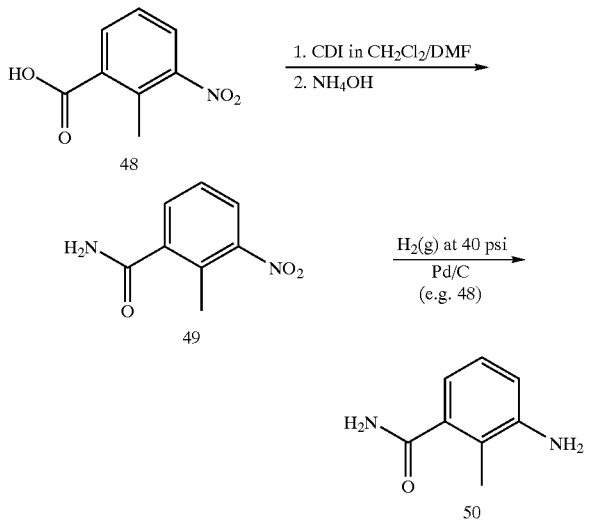

Nitro and carboxylic acid starting materials (e.g. 48) were dissolved in DCM and N,N-DMF (10:1). 1,1'-carbonyldiimidazole (1.2 equiv) was added, and the reaction stirred at rt for 5 h. Ammonium hydroxide (2 equiv) was then added. After stirring overnight at rt, the reaction was concentrated, washed with base and extracted with EtOAc to yield compound 49. Compound 49 was then hydrogenated at 40 psi on the PARR shaker in the presence of Pd/C catalyst. Filtration and concentration yielded the appropriate Z-amine coupling component 50. This same or similar method was used to make

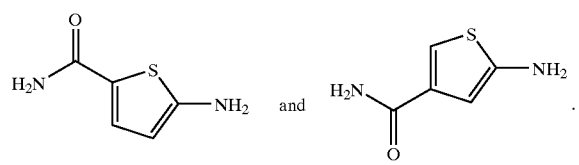

SCHEME N

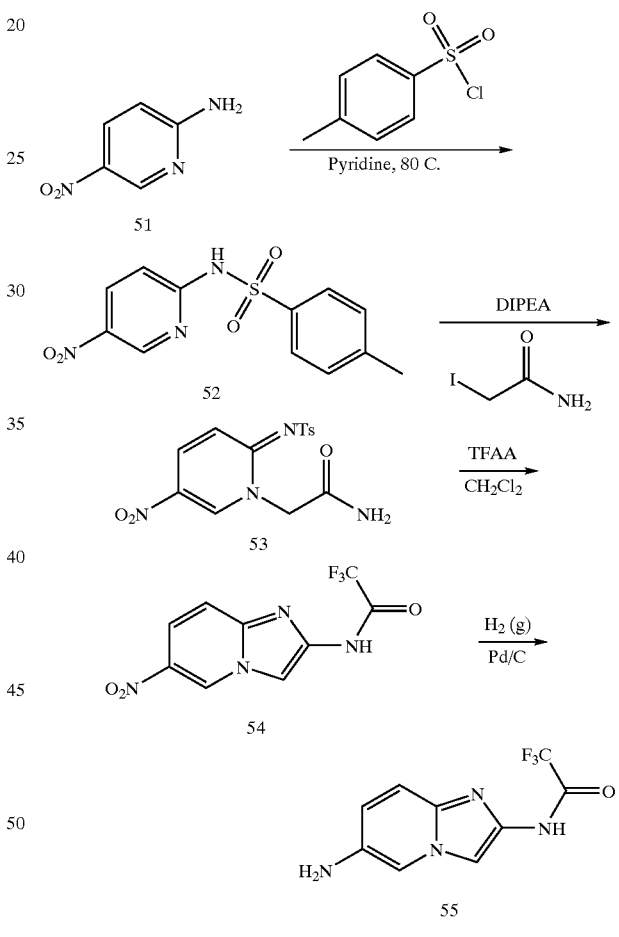

To a solution of compound 51 in 20 mL of pyridine was added toluenesulfonyl chloride. The solution was stirred for 18 h at 80° C. and cooled to rt and concentrated. The precipitate was taken up with water, filtered, and washed with water. The solid was then crystallized from EtOAc to give compound 52 as white needle crystals.

To a solution of compound 52 in 20 mL of N,N-DMF was added 0.79 g (6.1 mmol) of DIPEA and 1.13 g (6.1 mmol) of iodoacetamide at rt. The solution was stirred for 24 h and then poured into 100 mL of water and stirred for 1 h. The solid was collected and dried under vacuum to yield compound 53. Compound 53 was taken up with 20 mL DCM and 1.2 g (6.1 mmol) of trifluoroacetic anhydride was added at rt. The resulting solution was stirred for 5 h at rt and concentrated. The residue was taken up with EtOAc and washed with saturated sodium bicarbonate. The organic layer was dried over MgSO$_4$ and concentrated to give compound 54 as a white solid. MS, m/z (M+1)$^+$=289.

The resulting compound 54 was dissolved in EtOAc and Pd/C catalyst was added. The mixture was placed on the PARR shaker at 40 psi for 2 h. Filtering off the catalyst yielded the desired compound 55 in 80% yield.

SCHEME O

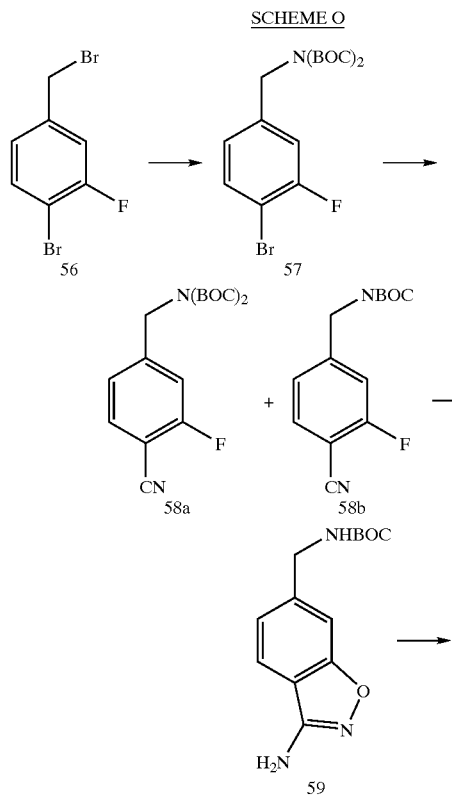

To a solution of 4-bromo-3-fluorotoluene (2.0 g, 10.58 mmol) in CCl$_4$ (40 ml) at RT was added NBS (2.0 g). The reaction was heated to reflux and benzoylperoxide (128 mg, 0.53 mmol) was added three times (total 384 mg) in 30 minute intervals. The reaction was cooled to RT, diluted with DCM (40 ml) and washed with sat. NaHCO$_3$ (2×). The organics were dried over MgSO$_4$, filtered and concentrated to isolated 56 (2.8 g crude).

To a solution of compound 56 (2.8 g, ~10.4 mmol) in DMF (45 ml) under nitrogen at RT was added BOC$_2$NH (3.4 g, 15.7 mmol) followed by KOtBu (1.76 g, 15.7 mmol). After a mild exotherm, the reaction was stirred at rt for 72 hr. The reaction was diluted with EtOAc (200 ml) and washed with 1N HCl, water, sat. NaHCO$_3$ and brine. Organics were dried over MgSO$_4$, filtered and concentrated. Purification by flash chromatography (silica gel, 2%–15% EtOAc in hexane) provided compound 57 (1.56 g). MS (M+Na)+=426, 428 (Br isotopic pattern).

To a solution of 57 (1.56 g, 3.84 mmol) in nitrogen degassed DMF (1% water, 20 ml) was added Pd(dba)$_3$ (70.3 mg, 0.077 mmol), DPPF (95.9 mg, 0.173 mmol) and Zn(CN)$_2$ (315 mg, 2.69 mmol). The reaction mixture was degassed with nitrogen for 30 minutes, sealed and heated at 110° C. for 20 hours. The reaction was diluted with EtOAc (100 ml) and filtered through a plug of celite which was then washed with EtOAc (2×50 ml). The eluent was then placed in a separatory funnel and washed with water (3×150 ml). The water layers were back extracted in the order generated. The combined EtOAc extracts were dried over MgSO$_4$, filtered and concentrated. Purification by flash chromatography (silica gel, 0 to 15% EtOAc in hexane) provided 58a (0.71 g) and 58b (0.45 g).

To a solution of acetohydroxamic acid (135 mg, 1.8 mmol) in DMF (5 ml) at RT was added KOtBu (1.0M THF, 1.8 ml, 1.8 mmol). A gelatinous suspension formed which was aggitated until well mixed. The suspension was allowed to set at RT for 5 minutes and then a solution of 58b (450 mg, 1.8 mmol) in DMF (15 ml) was added. The reaction was aggitated at RT for 20 hours. The reaction mixture was then diluted with EtOAc (150 ml) and washed with water (2×) and brine (1×). The organics were dried over MgSO$_4$, filtered, and concentrated. Crystallization from CH$_2$Cl$_2$/hexane gave compound 59 (240 mg). MS (M+H)+=264

Compound 59 (240 mg) was treated with 10%TFA/CH$_2$Cl$_2$ (5 ml) at RT for 3 hours. Solvents were removed and the residue was taken up with MeOH and added to a plug of Dowex 50W-X2 (H form, 10 g) resin. The resin captured amine was washed with MeOH, DCM and CH$_3$CN. Elution with 2M NH$_3$ in MeOH (60 ml) followed by concentration gave Z-amine coupling component 60. (170 mg).

SCHEME P

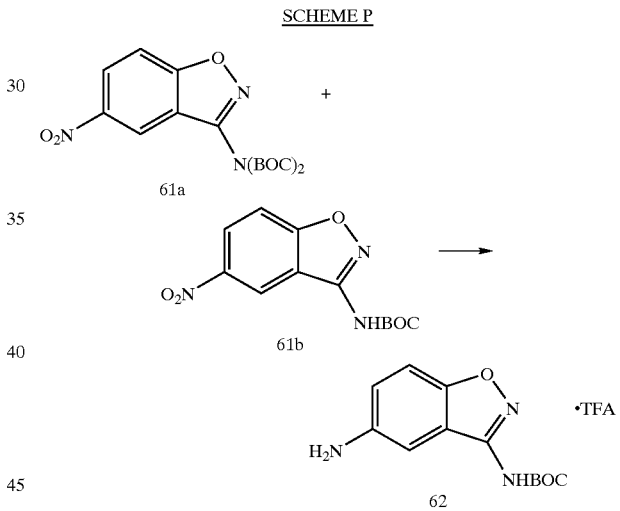

To a solution of 3-amino-5-nitrobenzisoxazole (200 mg, 1.12 mmol, lit. WO/0027627) in DCM (5 ml) was added BOC$_2$O (536 mg, 2.46 mmol) followed by DMAP (20 mg). The reaction mixture was stirred overnight. Solvent was removed and purification by flash chromatography (silica gel, CH$_2$Cl$_2$) gave a mixture of compounds 61a and 61b (350 mg combined).

The mixture of 61a and 61b (307 mg combined) was taken up in EtOH (10 ml) and treated with SnCl$_2$.2H$_2$O (751 mg). The reaction was heated to 70° C. for 1.5 hours. The reaction was diluted with EtOAc (75 ml), water (50 ml) and sat. NaHCO$_3$ (25 ml). The layers were mixed and allowed to separate. The organic layer was dried over MgSO$_4$, filtered, and concentrated. Purification by RP Prep HPLC provided BOC-protected amine-coupling component 62. (101 mg). MS (M+H)+=250.

Utility

The inventive compounds are inhibitors of the activated coagulation serine proteases known as Factor VIIa, Factor IXa, Factor Xa, Factor XIa, and thrombin and also inhibit other serine proteases, such as trypsin, tryptase, and urokinase. Thus, the compounds are useful for treating or preventing those processes, which involve the production or action of Factor VIIa, Factor IXa, Factor Xa, Factor XIa, thrombin, trypsin, and/or tryptase. In view of their urokinase inhibitory activity, they are useful as metastasis inhibitors in treating cancer. As used herein with reference to the utilities described below, the term "treating" or "treatment" encompasses prevention, partial alleviation, or cure of the disease or disorder.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

In addition, the inventive compounds are useful in preventing venous thrombosis, coagulation syndromes, deep vein thrombosis (DVT), disseminated intravascular coagulopathy, Kasabach-Merritt syndrome, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In view of their tryptase inhibitory activity, the inventive compounds are useful as anti-inflammatory agents, in treating chronic asthma, allergic rhinitis, inflammatory bowel disease, psoriasis, conjunctivitis, atopic dermatitis, pancreatis, rheumatoid arthritis, osteoarthritis, septic shock, and chronic inflammatory joint diseases, diseases of joint cartilage destruction, and/or vascular damage due to bacterial and/or viral infections. Additionally, the inventive compounds may be useful for treating diabetic retinopathy or motor neuron diseases such as amyotrophic lateral sclerosis, progressive muscular atrophy, and primary lateral sclerosis. Additionally, the inventive compounds may be useful for tissue remodeling diseases and for treating plaque instability and sequelli. In addition, these compounds may be useful for treating fibrotic diseases and conditions, for example, fibrosis, scleroderma, pulmonary fibrosis, liver cirrhosis, myocardial fibrosis, neurofibromas, and hypertrophic scars.

In addition, the compounds of the present invention are useful in treating cancer and preventing the prothrombotic complications of cancer. In view of their metastasis inhibition activity, the compounds are useful in treating tumor growth, as an adjunct to chemotherapy, and for treating diseases involving metastases including, but not limited to cancer, more particularly, cancer of the lung, prostate, colon, breast, ovaries, and bone. These compounds may also be useful in preventing angiogenesis.

The inventive compounds may also be used in combination with other antithrombotic or anticoagulant drugs such as thrombin inhibitors, platelet aggregation inhibitors such as aspirin, clopidogrel, ticlopidine or CS-747, warfarin, low molecular weight heparins (such as LOVENOX), GPIIb/GPIIIa blockers, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, itavastatin (Nissan/Kowa), and compounds disclosed in U.S. provisional applications No. 60/211,594 filed Jun. 15, 2000, and No. 60/211,595 filed Jun. 15, 2000; microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan); and/or ACE/NEP inhibitors (e.g., omapatrilat and gemopatrilat); β-blockers (such as propranolol, nadolol and carvedilol), PDE inhibitors in combination with aspirin, ifetroban, picotamide, ketanserin, or clopidogrel and the like. The inventive compounds are also useful in combination with anti-arrhythmic agents such as for atrial fibrillation, for example, amiodarone or dofetilide.

The inventive compounds may be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive compounds may also be used in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

The inventive compounds may also be useful in combination with other anticancer strategies and chemotherapies such as taxol and/or cisplatin.

The compounds may act synergistically with one or more of the above agents. For example, the inventive compounds may act synergistically with the above agents to prevent reocclusion following a successful thrombolytic therapy and/or reduce the time to reperfusion. Thus, reduced doses of thrombolytic agent(s) may be used, therefore minimizing potential hemorrhagic side effects.

The compounds of formula I may be administered by any means suitable for the condition to be treated, which may depend on the need for site-specific treatment or quantity of drug to be delivered. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories, or in the form of liposome particles. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

Enzyme Assays

Compound was prepared as a 5 mM stock in DMSO, diluted further in DMSO and added directly to the assays. The DMSO concentration for all these studies was less than 1% and compared to DMSO vehicle controls.

Human Factor VIIa was obtained from Enzyme Research Labs (Cat.# HFVIIA 1640). Human recombinant tissue factor (INNOVIN from Dade Behring Cat.# B4212-100; "20 ml vial") was diluted with 8 ml of $H_2O$ per vial and diluted further 1:30 into the 302 µl final assay volume. Tissue factor activated FVIIa enzymatic activity was measured in a buffer containing 150 mM NaCl, 5mM $CaCl_2$, 1 mM CHAPS and 1 mg/ml PEG 6000 (pH 7.4) with 1 nM FVIIa and 100 µM D-Ile-Pro-Arg-AFC (Enzyme Systems Products, Km>200 µM) 0.66% DMSO. The assay (302 µl total volume) was incubated at RT for 2 hr prior to reading fluorometric signal (Ex 405/Em 535) using a Victor 2 (Wallac) fluorescent plate reader.

Human Factor IXa (American Diagnostica #449b) enzymatic activity was measured in a buffer containing 50 mM Tris, 100 mM $CaCl_2$, 5 mM $CaCl_2$, 33% ethylene glycol at pH 7.5 using 96-well microtiter plates (Nunc #439454). The enzyme was incubated with the inhibitor at RT for three minutes prior to starting the reaction with 500 uM Spectrozyme FIXa (American Diagnostica #299). The $K_m$ for this substrate is estimated by American Diagnostica to be 1.3 mM. Time dependent optical density change was followed at 405 nm using a kinetic microplate read (Molecular Devices Spectramax Plus) at RT. Enzyme activity in the presence of inhibitor was expressed as fraction of a DMSO-containing control and curve fit to the equation: activity=control activity/(1+[I]/IC$_{50}$) using Excel Fit.

Human FXa (Calbiochem #233526) enzymatic activity was measured in a buffer containing 0.145 M NaCl, 0.005 M KCl, 1 mg/ml Polyethylene Glycol (PEG-8000), 0.030 M HEPES (pH 7.4) using 96-well microtiter plates (Nunc Immuno #439454). The enzyme was incubated with the inhibitor at RT for three minutes prior to starting the reaction with 100 µM S-2222 (phenyl-Ile-Glu-Gly-Arg-pNA, K$_m$=137 µM). The K$_m$ for this and other substrates was determined experimentally by measuring the enzyme activity at different substrate concentrations and curve fitting the data using Kaleidagraph V. Time-dependent optical density change was followed at 405 nm using a kinetic microplate reader (Molecular Devices UVmax) at RT. Enzyme activity in the presence of inhibitor was expressed as fraction of a DMSO-containing control and curve fit to the equation: activity=control activity/(1+[I]/IC$_{50}$) using Excel Fit.

Recombinant urokinase (Abbott Labs, Abbokinase) was assayed in the same buffer as FXa, but the reactions were started with 100 µM S-2444 (L-pyroGlu-Gly-Arg-pNA, K$_m$=31 µM). Human α-thrombin (Sigma) was measured as for FXa except that the reaction was started with 10 µM S-2238 (D-Phe-Pip-Arg-pNA, K$_m$=2.54 µM).

Human FXIa assay (Enzyme Research Labs) was measured as for FXa except that the reaction was started with 100 µM S-2366 (L-pyroGlu-Pro-Arg-pNA, K$_m$=86 µM).

Bovine and human pancreatic trypsin (Sigma) were assayed in 2 mM CaCl$_2$, 50 mM Tris/Cl (pH 8.0) and the reaction was started with 100 µM Chromozym-TRY (Carboxybenzoxy-Val-Gly-Arg-pNA, K$_m$=46 µM).

Tryptase inhibition activity was measured using either isolated human skin tryptase or recombinant human tryptase prepared from the human recombinant beta-protryptase expressed by baculovirus in insect cells. The expressed beta-protryptase to was purified using sequential immobilized heparin affinity resin followed by an immunoaffinity column using an anti-tryptase monoclonal antibody. The protryptase was activated by auto-catalytic removal of the N-terminal in the presence of dextran sulfate followed by dipeptidyl peptidase I (DPPI) removal of the two N-terminal amino acids to give the mature active enzyme (Sakai et al, *J. Clin. Invest.*, Vol. 97 (1996), at pp. 988–995). Essentially equivalent results were obtained using isolated native enzyme or the activated expressed enzyme. The tryptase enzyme was maintained in 2M sodium chloride, 10 nM 4-morpholine-propanesulfonic acid, pH 6.8. The assay procedure employed a 96 well microplate. To each well of the microplate (Nunc MaxiSorp), 250 µl of assay buffer [containing low molecular weight heparin and tris (hydroxymethyl)aminomethane] was added followed by 2.0 µl of the test compound in dimethylsulfoxide. The substrate (10 µl) was then added to each well to give a final concentration of 100 µM benzyloxycarbonyl-glycine-proline-arginine-p-nitroaniline (CBz-Gly-Pro-Arg-pNA). The microplate was then shaken on a platform vortex mixer at a setting of 800 (Sarstedt TPM-2). After a total of three minutes incubation, 10 µl of the working stock solution of tryptase was added to each well. The microplate was vortexed again for one minute and then incubated without shaking at RT for an additional 2 minutes. After this time the microplate was read on a microplate reader (Molecular Devices UV max) in the kinetic mode (405 nm wavelength) over twenty minutes at RT. To determine the compound concentration that inhibited half of the enzyme activity (IC$_{50}$), the fraction of control activity (FCA) was plotted as a function of the inhibitor concentration and curve to fit FCA/(1[I]/IC$_{50}$). The IC$_{50}$ for each compound was determined 2–4 times and the obtained values were averaged.

Applying the above-described assays, the inventive compounds demonstrated activity as inhibitors of Factors VIIa, IXa, Xa, XIa, IXa, tryptase and/or urokinase.

The following Examples illustrate embodiments of the inventive compounds and starting materials, and are not intended to limit the scope of the claims. For ease of reference, the following abbreviations are used herein:

The following Examples illustrate embodiments of the inventive compounds and starting materials, and are not intended to limit the scope of the claims. For ease of reference, the following abbreviations are used herein:

Abbreviations

Me=methyl
Et=ethyl
Ph=phenyl
Bn=benzyl
t-Bu=tertiary butyl
Boc=tert-butoxycarbonyl
CBZ=carbobenzyloxy or carbobenzoxy or benzyloxycarbonyl
THF=tetrahydrofuran
EtOAc=ethyl acetate
DMF=dimethyl formamide
i-PrOH=isopropanol
DMSO=dimethyl sulfoxide
DME=1,2 dimethoxyethane
DCE=1,2 dichloroethane
DCM=dichloromethane
AcOH=acetic acid
TFA=trifluoroacetic acid
i-Pr$_2$NEt=diisopropylethylamine
DMAP=4-dimethylaminopyridine
NMM=N-methyl morpholine
NaHCO$_3$=sodium bicarbonate
NaBH(OAc)$_3$=sodium triacetoxyborohydride
Pd/C=palladium on carbon
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
Pd(OAc)$_2$=Palladium acetate
CBZ-Cl=benzyl chloroformate
SAX=Strong Anion Exchanger
SCX=Strong Cation Exchanger
PVP=polyvinylpyridine
DCC=dicyclohexylcarbodiimide
DIC or DIPCDI=diisopropylcarbodiimide
DMA=dimethyl acetamide
DIAD=diisopropyl azodicarboxylate
DIEA=diisopropylethylamine
DIPEA=diisopropylethylamine
DPPF=1,1'-bis(diphenylphosphino)ferrocene
TEA=triethylamine
TBS=t-butyldimethylsilyl
Tf=trifluoromethanesulfonyl
L=liter
mL=milliliter μL=microliter
g=gram(s)
mg=milligram(s)
meq=milliequivalent
rt or RT=room temperature
conc.=concentrated
sat or sat'd=saturated
TLC=thin layer chromatography
HPLC=high performance liquid chromatography
RP HPLC=reverse phase HPLC
LC/MS=high performance liquid chromatography/mass spectrometry
MS or Mass Spec=mass spectrometry
MW=molecular weight
mp=melting point

EXAMPLES 1 AND 2

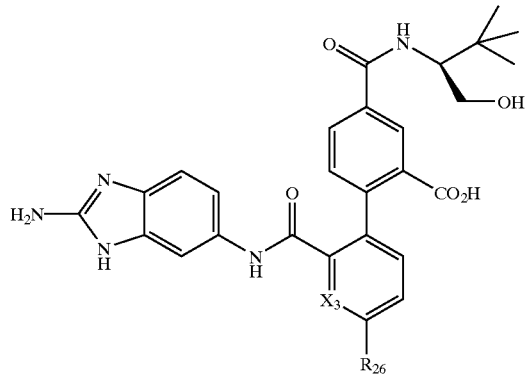

(Ic)

| Ex. No. | $X_3$ | $R_{26}$ | MS (M + H)$^+$ |
|---|---|---|---|
| 1 | N | OMe | 547 |
| 2 | CH | H | 516 |

Compounds having the formula (Ic), wherein $X_3$ and $R_{26}$ have the values listed in Table 1, were prepared using the following method (weights and percentages are approximate for the compound of Example 2).

Step A:

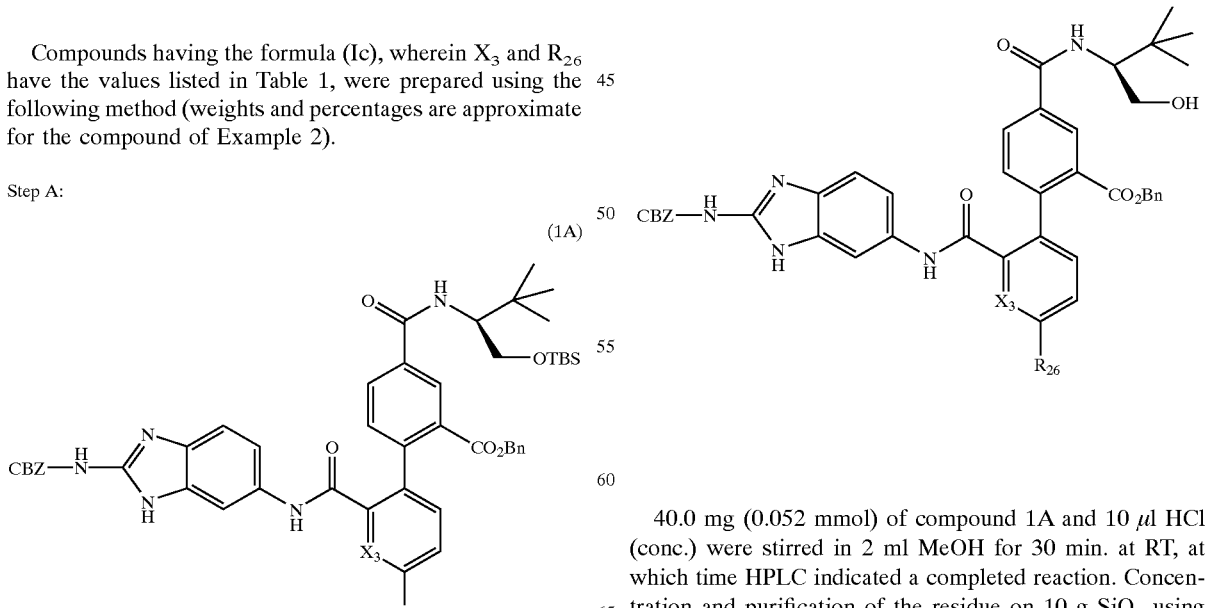

(1A)

62.0 mg (0.10 mmol) of Acid-1

(Acid-1)

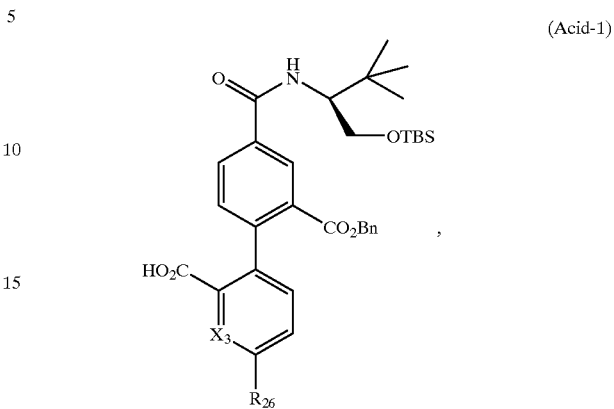

having desired groups $X_3$ and $R_{26}$, 31.1 mg (0.11 mmol) of 2-(CBZ-amino)-5-aminobenzimidazole, 21 mg (0.10 mmol) of DCC, 10.0 mg HOBT, and 2.0 mg DMAP were dissolved in 3 ml DMF and stirred at RT for 18 h. After that time, HPLC indicated a completed reaction. Concentration and purification on $SiO_2$ using $CHCl_3$/MeOH/water (9:1:0.1) yielded 40.7 mg of compound 1A as a white foam. Acid-1 can be prepared as shown in WO 99/41231.

Step B:

(1B)

40.0 mg (0.052 mmol) of compound 1A and 10 μl HCl (conc.) were stirred in 2 ml MeOH for 30 min. at RT, at which time HPLC indicated a completed reaction. Concentration and purification of the residue on 10 g $SiO_2$ using $CHCl_3$/MeOH/water (8:2:0.1) yielded 33.8 mg (97%) of compound 1B as a white foam.

Step C 33 mg (0.044 mmol) of compound 1B from Step B, 10 mg Pd/C (10%), and 0.05 ml 1.0 N HCl in 5 ml dioxane were hydrogenated (balloon pressure with $H_2$) for 12 h. Filtration, concentration, and prep-HPLC purification yielded after lyophilization 20.3 mg (72%) of the desired product as a white powder in the form of its TFA salt. 100% purity by HPLC.

EXAMPLE 3

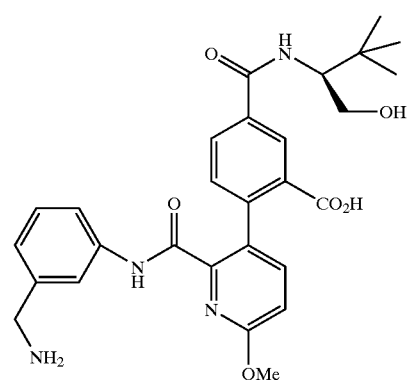

Step A:

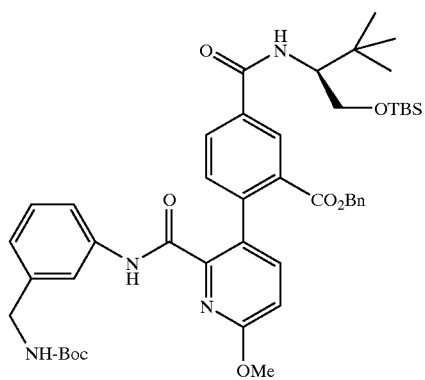

(3A)

1-Ethyl-3-(3-dimethylaminopropyl)carbodiimide hydrochloride (15.5 mg, 0.08 mmol) was added to a stirred solution of 50 mg (0.08 mmol) of Acid-1 from Example 1 (having the desired groups $X_3$ and $R_{26}$), 9 μL (0.082 mmol) of NMM, 11 mg (0.08 mmol) of 1-hydroxybenzotriazole hydrate, and 18 mg (0.08 mmol) of amine coupling component o-(N-Boc-aminomethyl)aniline (see *J. Med. Chem.*, Vol. 42 (14) (1999) at p. 2504), in 1.5 mL of DCM at 0° C. under Ar. The reaction was stirred for two days at rt, concentrated, and taken up in EtOAc and water. The EtOAc was washed with water (2×), dried (sodium sulfate), and concentrated to a glassy residue (69 mg), which was chromatographed over silica gel using 1% MeOH in methylene chloride to give 55 mg of compound 3A as a glassy residue.

Step B:

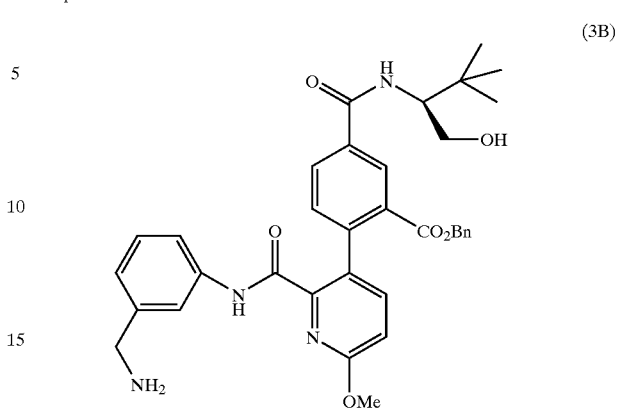

(3B)

A solution of compound 3A (24 mg, 0.029 mmol), 1.2 mL of DCM, and 0.3 mL of TFA was stirred at RT for 2 h and concentrated, and then concentrated from 10 MeOH (4×) to a residue. Concentrated ammonia (0.5 mL) was added to a solution of the residue in MeOH (0.8 mL). After stirring for 5 min., the solution was diluted with MeOH and concentrated to a residue, which was taken up in EtOAc and water. After two extractions with EtOAc, the combined EtOAc was washed with water, dried (sodium sulfate), and concentrated to give 19 mg of crude product as a clear oily residue. Step 3B was repeated using 26 mg (0.032 mmol) of compound 3A to make another 13 mg of crude compound 3B, and the combined crude product (19 mg and 13 mg) was chromatographed over silica gel using 10% and then 15% MeOH in methylene chloride to give 22 mg of pure compound 3B as a glassy solid.

Step C

A mixture of compound 3B (19 mg, 0.031 mmol), 2.5 mL of MeOH, and 33 μL of 1.0 N HCl was hydrogenated for 20 min. in the presence of 6 mg of 10% Pd/C. After filtration and concentration of the filtrate, the residue was lyophilized from dioxane-water to give 16.7 mg of Example 3 as a white solid in the HCl salt form. MS $(M+H)^+=521$.

EXAMPLES 4–6

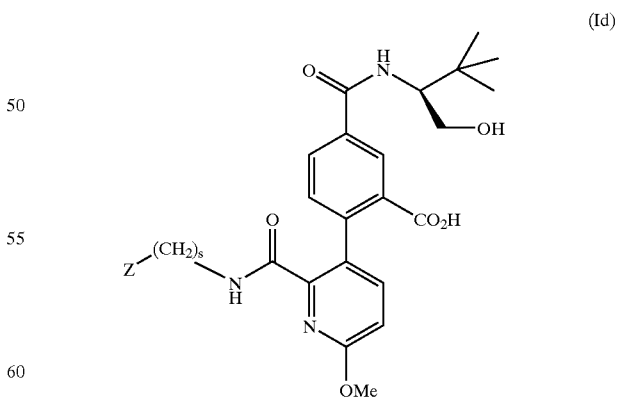

(Id)

Compounds of formula (Id) were prepared, wherein Z and s have the values listed in Table 2, using the method recited in Example 3 and the amine-coupling components listed in Table 2.

TABLE 2

| Ex. | Amine-coupling component | s | Z | MS (M + H)+ |
|---|---|---|---|---|
| 4 | 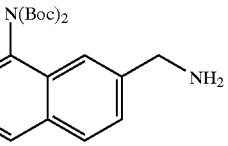 | 1 | 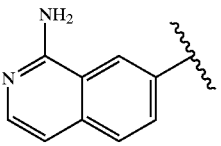 | 572 |
| 5 | 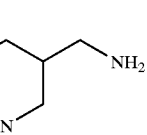 | 1 | 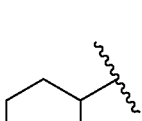 | 513 |
| 6 | 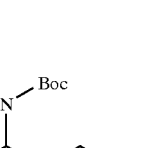 | 0 | 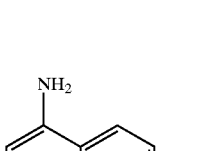 | 558 |

EXAMPLE 7

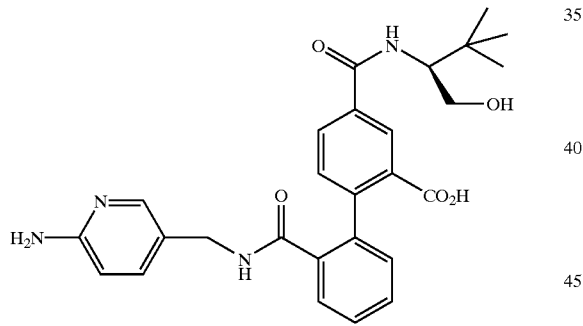

EXAMPLES 8–27

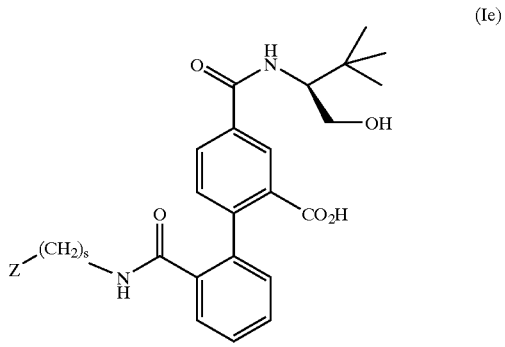

(Ie)

A solution of Acid-1 from Example 1 (having desired groups $X_3$ and $R_{26}$) (50 mg, 0.085 mmol), HOBT (1.48 mg, 0.011 mmol), DCC (23 mg, 0.11 mmol), and DMAP (catalytic amount) was stirred for 10 min. To this solution was added amine coupling component 2-amino-5-aminomethylpyridine (13.5 mg, 0.11 mmol) (see German patent publication DE 430110 A1 (1994)). The mixture was stirred overnight and concentrated. The residue was dissolved in 1 mL of MeOH, treated with 0.2 mL of conc. HCl, and stirred for 10 min. MeOH was replaced with THF, and 0.2 mL of 50% NaOH was added. The mixture was stirred overnight, neutralized with conc. HCl, and concentrated. The residue was dissolved in MeOH and filtered. The filtrate was purified with reverse phase Prep HPLC to give 21 mg (83%) of Example 7 as a white solid. MS (M+H)+=491.

Examples 8–27 having Formula (Ie), above, were prepared wherein the values s and Z are as recited below in Table 3. The compound of Example 8 was prepared in the same manner described above for Example 7, and the compounds of Examples 9–11 were prepared in the manner described above for Example 3, using an appropriate amine-coupling component. Compounds of Examples 12–27 were synthesized via automation using a TECAN liquid handler for reagents and starting material addition and Procedures A and B below. The desired amine-coupling components were prepared as set forth in the previous schemes, as known in the field, and/or as set forth in the literature, i.e., see, e.g., Yatsunami et al., S. Eur. Pat. Appl. No. EP 343560 (1989) (Exs. 9, 31); Kraska et al., Pol. J. Chem. Vol. 58 (1984) at p. 1025 (Exs. 10, 12, 13); Kato et.al., PCT Intern. Applic. WO 00/09506 A1 (Ex. 19); Beattie et al., J. Med. Chem., Vol. 20 (1977) at p. 718 (Ex. 22); Kawano et al., PCT Intern. Application WO 97/09982 (Ex. 23); and Feng et al., J. Med. Chem., Vol. 40 (1997) at p. 3726 (Ex. 27). Acid-2 was prepared according to procedures shown in WO 99/41231.

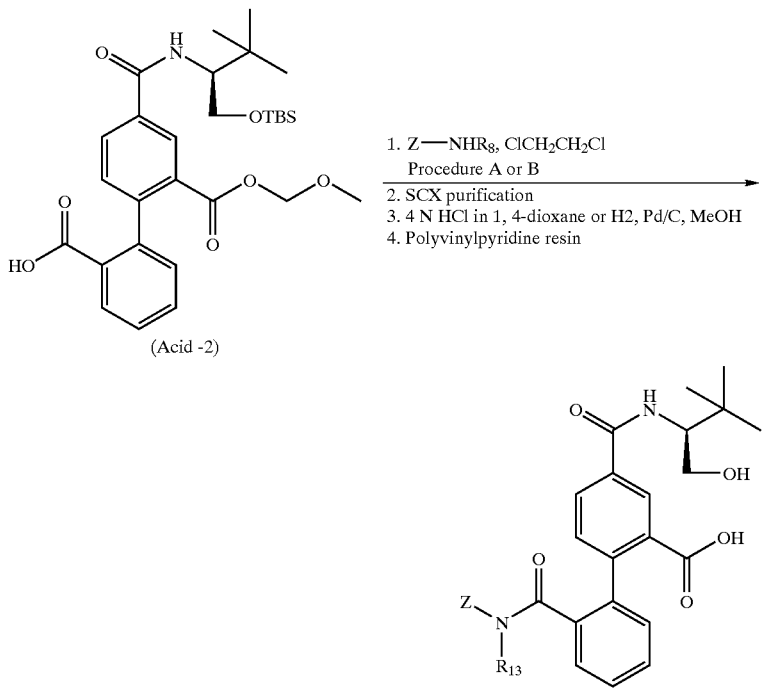

(Acid -2)

1. Z—NHR₈, ClCH₂CH₂Cl
   Procedure A or B
2. SCX purification
3. 4 N HCl in 1, 4-dioxane or H2, Pd/C, MeOH
4. Polyvinylpyridine resin Procedure A: for Monoprotected Diamines To 33 reaction tubes (12 mm×65 mm) in a mini-reactor were added 0.5 mL (30 mg, 0.055 mmol, 1 eq) of a stock solution of Acid-2 in ClCH₂CH₂Cl, 0.25 mL (16 mg, 0.083 mmol, 1.5 eq) of a stock solution of EDC in CH₂Cl₂, and 0.25 mL (10 mg, 0.083 mmol, 1.5 eq) of a stock solution of DMAP in ClCH₂CH₂Cl. The mini-reactor was removed and shaken on an orbital shaker for 20 minutes. Amines having the desired groups Z and $R_{13}$ (0.066 mmol, 1.2 eq) were added and the mixture was shaken on an orbital shaker for 3 days.

The reaction mixtures were purified via solid phase extraction using a SCX cation exchange column (CUBCXHL5R3, 500 MG/3 ML/50 PKG) as follows:

1). Columns were conditioned with 1.5 mL of 1:1 CH₃CN-iPr₂OH solution;
2). Reaction mixture (1 mL) was loaded on to SCX columns; and
3). Columns were eluted with 1.5 mL of 1:1 CH₃CN-iPr₂OH solution into 9 mm×80 mm microtubes.

The CH₃CN-iPr₂OH solutions were concentrated using a speed vac for 12 h. (For CBZ-protected amines, the residues were hydrogenated with 5 mg of Pd/C in 2 ml MeOH. After filtration, the MeOH solutions were concentrated to give residues.) The residues were treated with 4 N HCl in 1,4-dioxane, sonicated for 1 min, and loaded on PVP column. The PVP columns were eluted with 3 mL of 1:1 water-1,4-dioxane solution. The solutions were concentrated using a speed vac for 12 h to give the final products.

Procedure B: for Unprotected Diamines

To 12 mm×65 mm reaction tubes in a mini-reactor was added 0.5 mL (30 mg, 0.055 mmol, 1.1 eq) of a stock solution of Acid-2 in ClCH₂CH₂Cl, 11.75 µL (9.5 mg, 0.075 mmol, 1.5 eq) of a stock solution of DIC, and 0.25 mL (10 mg, 0.075 mmol, 1.5 eq) of a stock solution of HOAT in a 5:1 ClCH₂CH₂Cl-DMA solution. The mini-reactor was removed and shaken on an orbital shaker for 20 min. Amines having the desired groups Z and $R_{13}$ (0.066 mmol, 1.2 eq) and iPr₂NEt (19 µL, 14 mg, 2.2 eq.) (or 2 HCl salts), were added, and the mixture was shaken on an orbital shaker for 3 days.

The reaction mixtures were purified via solid phase extraction using a SCX cation exchange column (CUBCXHL5R3, 500 MG/3 ML/50 PKG) as follows:

1). Columns were conditioned with 1.5 mL of 1:1 CH₃CN-iPr₂OH solution;
2). Reaction mixture (1 mL) was loaded on to SCX columns;
3). Columns were rinsed with 1.5 mL of a 1:1 CH₃CN-iPr₂OH solution; and
4). Columns were eluted with 1.5 mL of a 2M NH₃ MeOH solution into 9 mm×80 mm microtubes.

TABLE 3

| Ex. | s | Z | MS (M + H)⁺ |
|---|---|---|---|
| 8 | 1 | 3-amino-benzo[d]isoxazol-6-yl | 531 |
| 9 | 0 | isoindolin-5-yl | 502 |
| 10 | 0 | 4-(aminomethyl)-2-chlorophenyl | 524 |

TABLE 3-continued
| Ex. | s | Z | MS (M + H)+ |
|---|---|---|---|
| 11 | 0 | 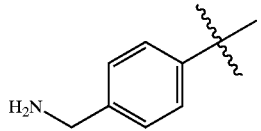 | 490 |
| 12 | 0 | 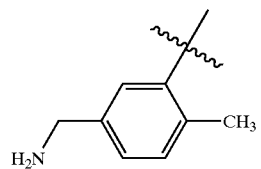 | 504 |
| 13 | 0 | 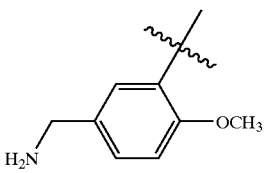 | 520 |
| 14 | 0 | 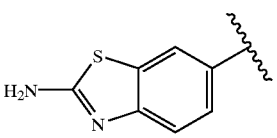 | 533 |
| 15 | 0 | 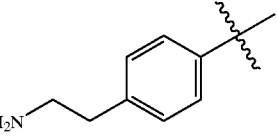 | 504 |
| 16 | 1 | 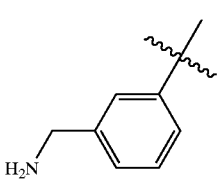 | 504 |
| 17 | 1 | 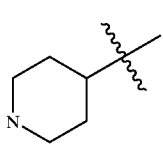 | 482 |
| 18 | 1 | 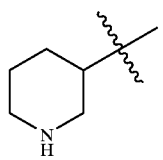 | 482 |
| 19 | 2 | 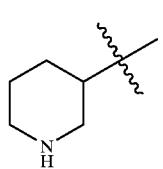 | 496 |
| 20 | 0 | 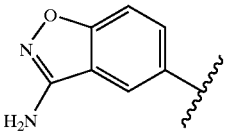 | 517 |
| 21 | 0 | 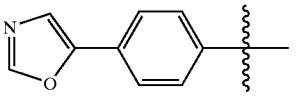 | 528 |
| 22 | 1 | 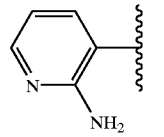 | 491 |
| 23 | 1 | 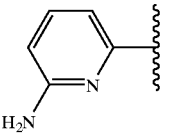 | 491 |
| 24 | 0 | 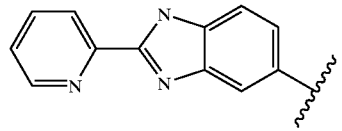 | 578 |
| 25 | 0 | 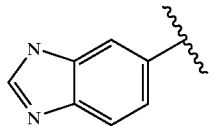 | 501 |
| 26 | 1 | 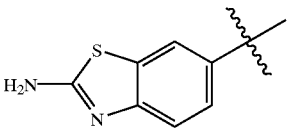 | 547 |
| 27 | 1 |  | 497 |

EXAMPLES 28–31

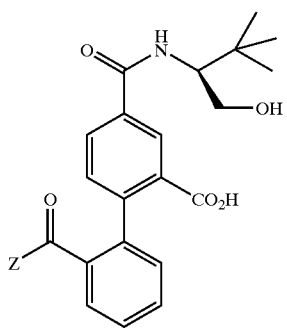
(If)

Compounds having the Formula (If) wherein Z has the values in Table 4 were synthesized using the same procedures as described above for Examples 12–27.

TABLE 4

| Ex. | Z | MS (M + H)+ |
|---|---|---|
| 28 | H₂N-CH₂-piperidinyl | 482 |
| 29 | H₂N-CH₂CH₂-piperidinyl | 496 |
| 30 | piperidinyl-piperidinyl | 536 |
| 31 | H₂N-isoindolinyl | 502 |

EXAMPLE 32

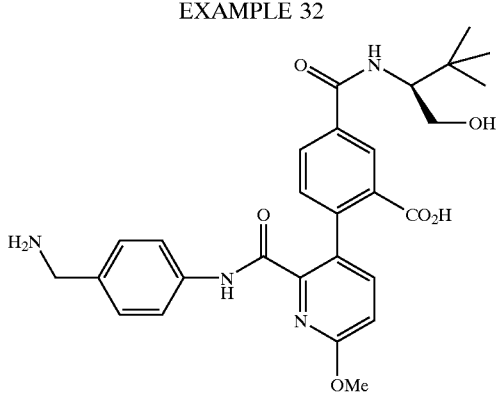

Step A:

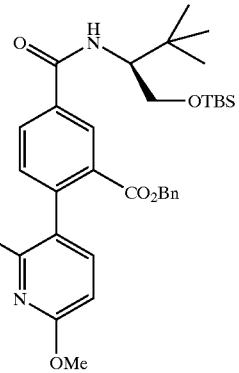
(32A)

To Alltech Filter Tubes (4 mL, 20 micron) was added a mixture of Acid-1 (having desired groups $X_3$ and $R_{26}$) (58 mg, 0.093 mmol), Boc-aminomethyl-4-aniline (24 mg, 0.11 mmol), DIC (13.84 mg, 0.11 mmol), HOAT (15 mg, 0.11 mmol) and DIEA (35.5 mg, 0.28) in DMF/DCE (1.0/1.0 mL). The reaction tubes were shaken at RT for 4 days. The reaction mixture was concentrated in speed vac to give the desired compound 32A.

Step B

To compound 32A was added 40% TFA (6 mL), and the mixture was sonicated for 2 min. and allowed to sit at RT for 3 h. The solvent was removed in speed vac, and conc. NH₄OH (0.3 mL) and MeOH (1.0 mL) were added. After concentration in speed vac, the residue was purified on Prep HPLC (YMC S5 ODS 30×100 mm). To the purified intermediate was added 10% Pd/C (15 mg) in MeOH (3 mL), and the solution was stirred at RT under hydrogen (balloon pressure) until the starting material disappeared. The reaction mixture was filtered, conc. NH₄OH/MeOH (0.3/1.0 mL) was added, and the filtrate was concentrated in speed vac to give the desired product (8.6 mg). MS (M+H)+=521.

EXAMPLE 33

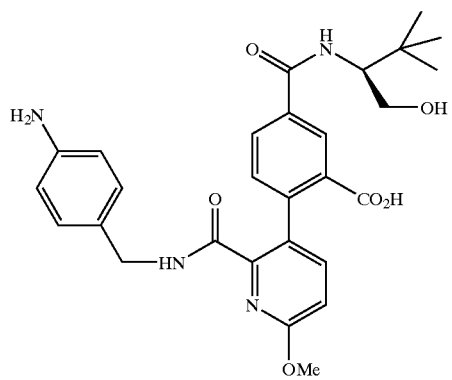

Example 33 was prepared using the same procedure as for Example 32, except 4-aminomethyl aniline (13 mg, 0.11 mmol) was used in place of Boc-aminomethyl-4-aniline to make the corresponding intermediate. To this intermediate was then added 1% conc. HCl in MeOH (6 mL), in place of 40% TFA, which was sonicated for 30 seconds and allowed to sit at RT for 30 min. MS (M+H)$^+$=521.

EXAMPLES 34–41

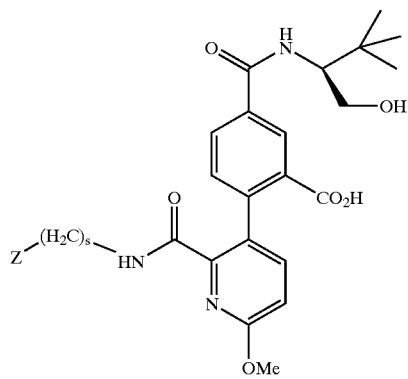

(Ig)

Compounds having the formula (Ig), wherein s and Z have the values listed in Table 5 were prepared in the manner described above for Examples 32 and 33, using an appropriate amine-coupling component.

TABLE 5

| Ex. | s | Z | MS (M + H)$^+$ |
|---|---|---|---|
| 34 | 0 | (trans-4-aminomethylcyclohexyl) | 527 |
| 35 | 1 | (1-aminoisoquinolin-6-yl) | 572 |
| 36 | 1 | (4-aminoisoquinolin-8-yl) | 572 |
| 37 | 1 | (3-aminophenyl) | 521 |

TABLE 5-continued

| Ex. | s | Z | MS (M + H)$^+$ |
|---|---|---|---|
| 38 | 1 | (2-amino-4-aminopyrimidin-5-yl) | 538 |
| 39 | 1 | (2,4-diaminoquinazolin-6-yl) | 588 |
| 40 | 1 | (6-aminopyridin-3-yl) | 522 |
| 41 | 0 | (1,2,3,4-tetrahydroisoquinolin-6-yl) | 547 |

EXAMPLE 42

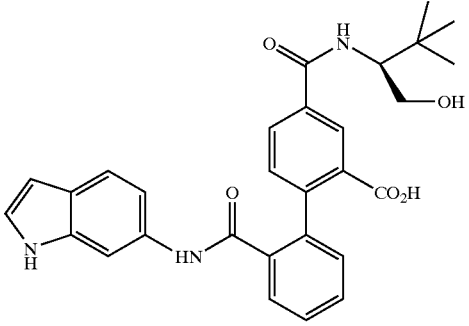

5-aminoindole (13 mg, 0.091 mmol), TEA (13 μL, 0.091 mmol), and a catalytic amount of DMAP and EDCI (18 mg, 0.091 mmol) were added to a solution of Acid-1 (Example 1) where $X_3$ is C and $R_{26}$ is H (50 mg, 0.085 mmol). After stirring overnight at RT, tetra-butyl ammonium fluoride (0.45 ml, 0.45 mmol) in THF was added to the reaction mixture. The reaction was allowed to stir for 1 h at RT, a KOH solution (1 ml, 1 N) was added, and the reaction was allowed to stir for another 1 h. The reaction was quenched with 1 N HCl (2 ml), extracted with EtOAc (2×5 ml). The organic phase was further washed with 1 N HCl (2×5 ml) and saturated NaCl solution and dried over MgSO$_4$. The solvent was removed to afford the above product (40.6 mg) as a brown solid.

EXAMPLES 43–49

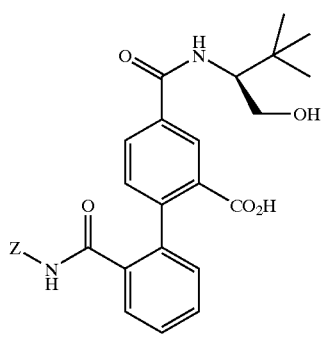

Compounds having the formula (Ih) wherein Z has the values listed in Table 6 were prepared in the manner described above for Example 42, using an appropriate amine-coupling component.

TABLE 6

| Ex. | Z | MS (M + H)+ |
|---|---|---|
| 43 | 5-methylindole | 500 |
| 44 | 2-methyl-5-methylbenzimidazole | 515 |
| 45 | 1,2-dimethyl-5-methylindole | 528 |
| 46 | 2-methyl-5-methylindole | 514 |
| 47 | 2-methyl-6-methylbenzofuran | 515 |
| 48 | 7-methylindole | 500 |
| 49 | 2-methyl-6-methylindole | 514 |

EXAMPLE 50

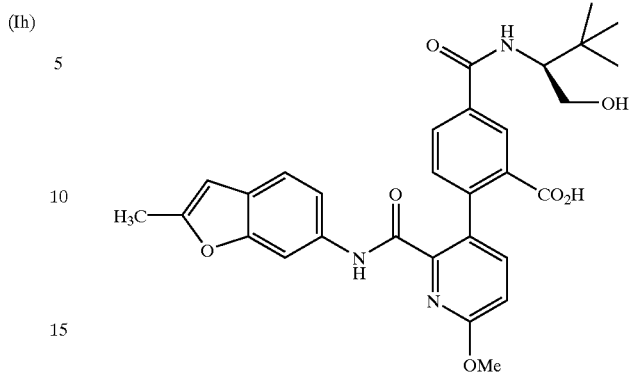

Example 50 was prepared in the same manner described above for Example 42. MS (M+H)+=546.

EXAMPLES 51 and 52

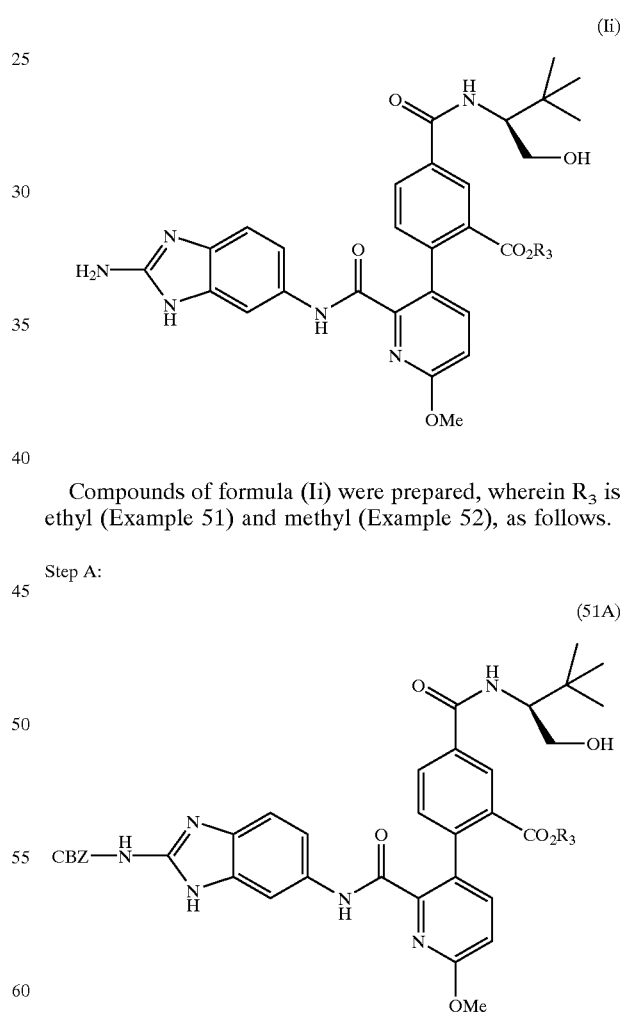

Compounds of formula (Ii) were prepared, wherein R$_3$ is ethyl (Example 51) and methyl (Example 52), as follows.

Step A:

To make Compound 51A wherein R$_3$ is ethyl, a solution of sodium ethoxide in EtOH was added to a THF solution of Compound 1B. The mixture was stirred overnight. The reaction mixture was worked up and purified to afford the desired Compound 51A. To make Compound 51A wherein $R_3$ is methyl, the same procedure was used using a solution of sodium methoxide in MeOH.

Step B

A solution of Compound 51A having the desired group $R_3$ was stirred under 1 atmosphere of hydrogen in the presence of 10% Pd/C. After 1 hr, the catalyst was filtered off and the solvent removed to afford the desired compound. MS $(M+H)^+=575$ (Ex. 51); 561 (Ex. 52).

EXAMPLE 53

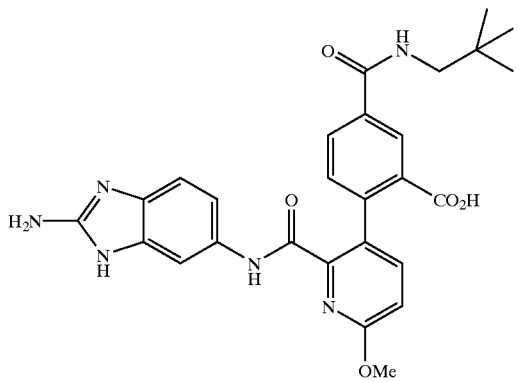

Step A:

(53A)

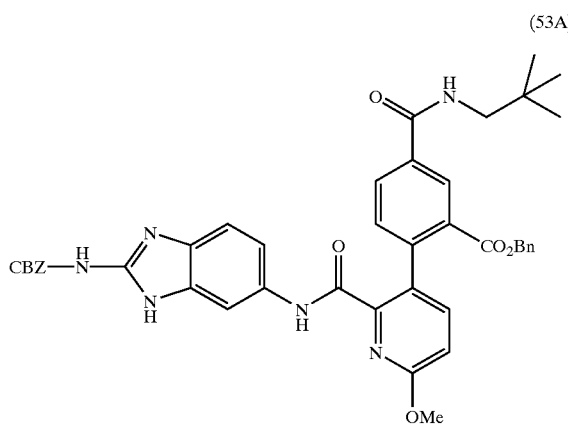

To a mixture of 73 mg of

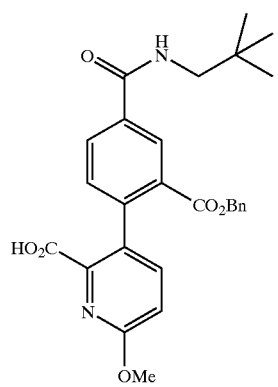

0.12 mmol) (Acid-3), 35 mg (0.12 mmol) of 2-(CBZ-amino)-5-aminobenzimidazole, 2 mg (0.014 mmol) of 1-hydroxy-7-azabenzotriazole, and 30 mg (0.144 mmol) of N,N'-dicyclohexylcarbodiimide, were added 0.7 mL of DMF and 1 mg of DMAP. The mixture was stirred for 3 h at RT, stored overnight in the refrigerator, filtered, and concentrated to a residue. The residue was triturated with EtOAc and after filtration, the EtOAc was washed sequentially with water, 5% potassium hydrogen sulfate, water, and brine, dried (sodium sulfate), and concentrated to an oily residue (97 mg). Chromatography of the residue over silica gel using 1–5% MeOH in DCM gave 68 mg of compound 53A. Acid 3 was prepared according to procedures described in WO 99/41231.

Step B 65 mg (0.088 mmol) of compound 53A in a mixture of 1 mL of dioxane, 3 mL of MeOH, 100 µL of 1.00 N HCl, and 22 mg of 10% Pd/C was hydrogenated at 1 atmosphere for 4 h. After filtration, the filtrate was concentrated, and the residue was treated with dioxane and water to give 39 mg of Example 53 as a white solid. MS $(M+H)^+=517$.

EXAMPLE 54

Step A:

(54A)

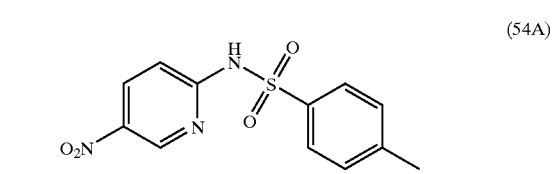

To a solution of 5 g (35 mmol) of 5-nitro-2-aminopyridine

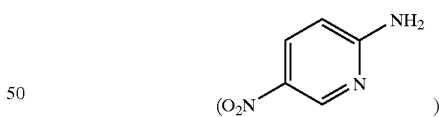

in 20 mL of pyridine was added 7.5 g (39 mmol) of toluenesulfonyl chloride

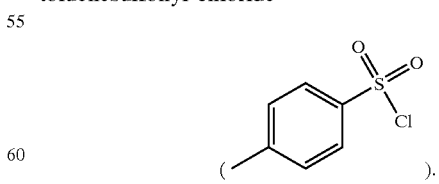

The solution was stirred for 18 h at 80° C. and cooled to rt and concentrated. The precipitate was taken up with water, filtered, and washed with water. The solid was then crystallized from EtOAc to give 4.3 g (40%) of compound 54A as white needle crystals.

Step B:

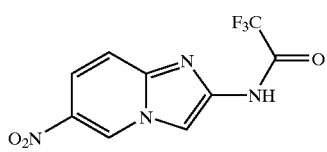
(54B)

To a solution of 1.5 g (5 mmol) of compound 54A in 20 mL of DMF was added 0.79 g (6.1 mmol) of DIPEA and 1.13 g(6.1 mmol) of iodoacetamide at rt. The solution was stirred for 24 h and then poured into 100 mL of water and stirred for 1 h. The solid was collected and dried under vacuum. The solid was taken up with 20 mL DCM, and then 1.2 g (6.1 mmol) of trifluoroacetic anhydride was added at rt. The resulting solution was stirred for 5 h at rt and concentrated. The residue was taken up with EtOAc and washed with sat'd NaHCO$_3$. The organic layer was dried over MgSO$_4$ and concentrated to give 0.32 g of compound 54B as a white solid. MS, m/z (M+1)$^+$=289.

Step C:

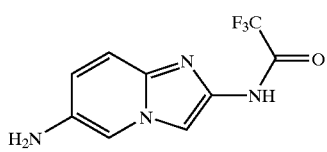
(54C)

Compound 54B was dissolved in EtOAc and Pd/C catalyst was added. The mixture was placed on the PARR shaker at 40 psi for 2 h. Filtering off the catalyst yielded compound 54C in 80% yield.

Step D

EXAMPLE 54

Compound 54C was coupled to Acid,

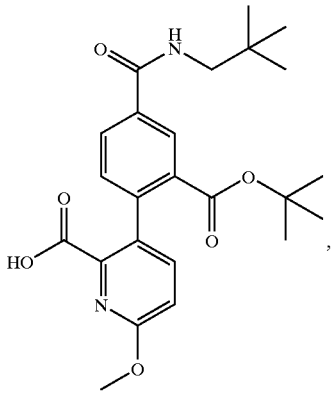

using EDAC, HOAT, and 4-DMAP in DCM. The resulting product was purified by prep HPLC. The tert-butyl protecting group was removed by treating the compound with TFA in DCM. The trifluoro acetamide protecting group was removed by dissolving the compound in DMSO and adding 10 eq. of solid NaOH. The mixture was stirred for 12 h at rt and purified by prep HPLC to give Example 54.

EXAMPLE 55

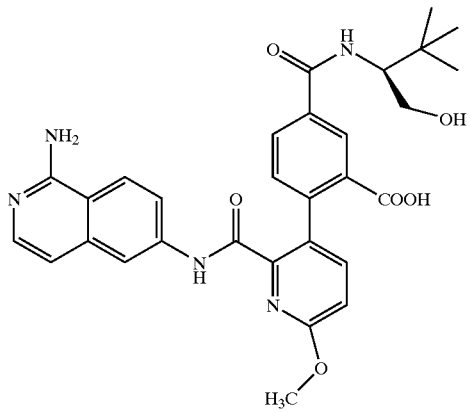

Step A:

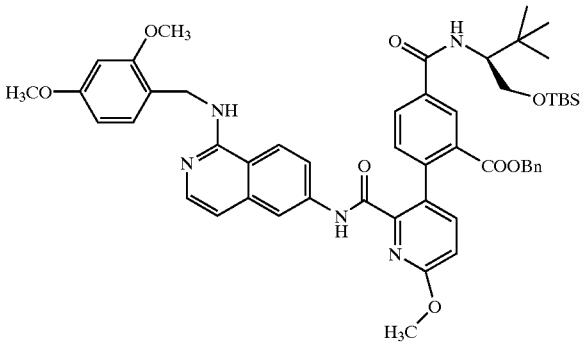

In a solution of DMF (3 mL) were dissolved amine-coupling component 33 from Scheme I (47.0 mg, 0.15 mmol), Acid-1 from Example 1 (93.0 mg, 0.15 mmol) (where X is N and R$_{26}$ is OCH$_3$), 45 mg (0.22 mmol) DCC, 4 mg HOAT, and 3 mg DMAP. The solution was stirred under Ar at rt for 24 h. After that time both the amine and the acid were consumed (HPLC). The reaction mixture was filtered, the filtrate concentrated, and the residue taken up in 5 ml EtOAc to afford a solution of crude compound 55A. The crude compound was washed with brine (3×3 ml), dried over Na$_2$SO$_4$ and concentrated. The oily residue was purified by column chromatography on 150 g SiO$_2$ using EtOAc/DCM (2:8) and EtOAc/DCM/IP (2:8:0.2) yielded 90 mg (67%) of compound 55A as a white foam.

Step B:

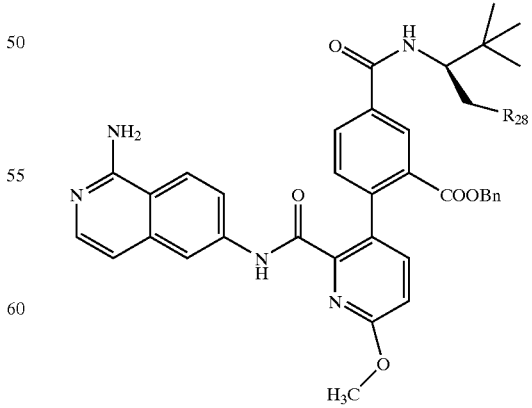

R$_{28}$ = OH(55B.1)
+ OC(═O)CF$_3$(55B.2)

85 mg (0.93 mmol) of compound 55A was stirred at rt in 4 ml TFA/anisole (1:1) for 24 h. HPLC and LC-mass indicated consumption of 55A and formation of two new compounds, i.e., 55B.1 where $R_{28}$=OH (M+H=648) and 55B.2 where $R_{28}$=OC(=O)CF$_3$ (M+H=744). Concentration and treatment of the residue with ether yielded 85 mg of a white solid of the TFA salts of the mixture with no other side products indicated a 1:3 mixture for 55B.1 and 55B.2.

Step C

EXAMPLE 55

80 mg of the mixture from Step B was dissolved in 3 ml dioxane and stirred with 1 ml of 1.0 N NaOH for 24 h. At that time LC-mass showed a completed reaction. Concentration and prep-HPLC purification of the residue gave 39 mg of Example 55 in the TFA salt form as a white lyophilate (50.4% over two steps). HPLC-purity 100%, LR-MS (M+H)$^+$=558

EXAMPLE 56

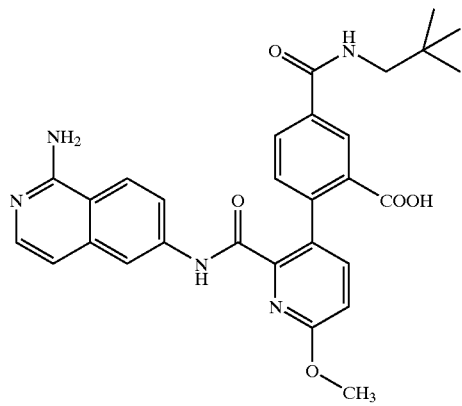

Step A:

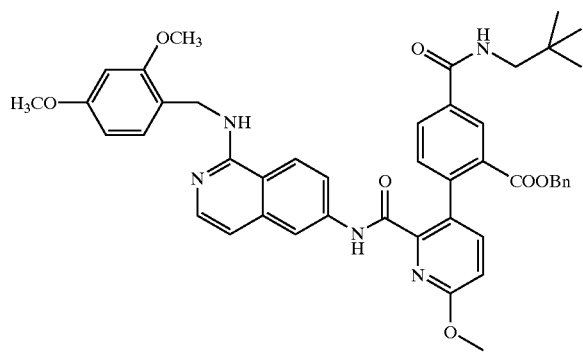

25 mg (0.051 mmol) of Acid-3 from Example 53, 15.4 mg (0.05 mmol) of amine-coupling component 33 from Scheme I, 15 mg (0.07 mmol) DCC, 1 mg HOAT, and 1 mg DMAP were dissolved in 2 ml dry DMF and stirred under Ar at rt for 18 h. HPLC indicated a complete reaction. The suspension was filtered and the filtrate washed with 1 ml EtOAc. Concentration of the filtrate and column chromatography of the residue on SiO$_2$ using EtOAc/DCM (2:8) yielded 30 mg of compound 56A (76.7%). MS (M+H)$^+$=768.

Step B:

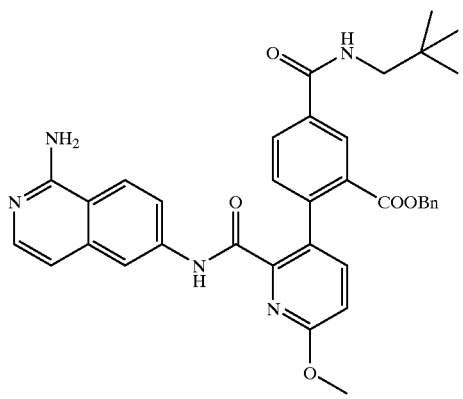

29 mg (0.038 mmol) of compound 56A was stirred in 2 ml TFA/anisole (1:1) at rt. After N$_2$ protection for 24 h, LC-mass indicated a completed reaction. Concentration and treatment of the residue with ether yielded 25 mg of a beige powder of the crude TFA salt of compound 56B. This material was used without further purification in the next step.

Step C

EXAMPLE 56

24 mg (0.027 mmol) of the TFA salt of compound 56B was stirred in 2 ml dioxane with 1 ml 1.0 N NaOH for 24 h. The reaction was monitored by HPLC/LC-mass. After removal of the solvent in vacuo, the residue was dissolved in solvent B (90%MeOH/10%water, plus 0.1%TFA) and purified by prep-HPLC to yield 13 mg of Example 56 in the TFA salt form as a white lyophilate (64% yield). MS(M+H)$^+$=528, HPLC-purity 95%.

EXAMPLE 57

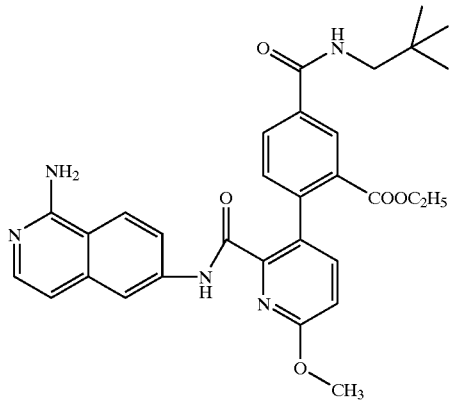

Step A:

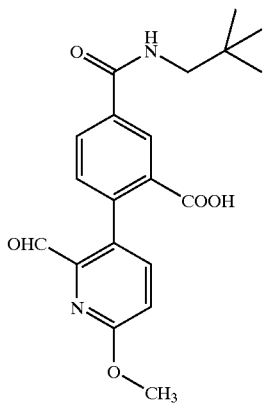
(57A)

To 10 ml of DCM was added 426.5 mg (1.0 mmol) of

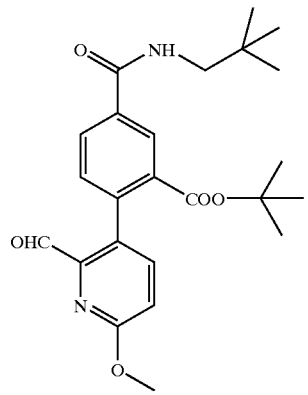

and 5 ml of TFA, and the solution was stirred first for 1 h at 0° C. and then for 2 h at rt to complete the deprotection. The mixture was concentrated to a colorless oil. The concentration was repeated three times with 3 ml toluene added each time to remove excess TFA to yield 382 mg of compound 57A as a colorless oil. HPLC purity=100%. LC-Mas 377.

Step B:

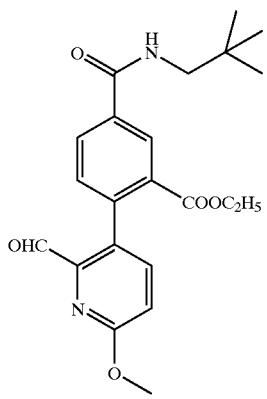
(57B)

380 mg (0.10 mmol) of compound 57A was dissolved in 15 ml acetonitrile, and to the solution were added $Cs_2CO_3$ (326 mg, 1.0 mmol), and $C_2H_5I$ (170 mg, 1.10 mmol). The mixture was stirred for 18 h at rt with HPLC-monitoring to complete the reaction. The suspension was filtered and the filter residue washed with 10 ml EtOAc. The combined filtrate was concentrated and the residue dissolved in 30 ml EtOAc. The residue was washed with half brine and brine, dried over $Na_2SO_4$, and the organic layer was concentrated to yield 398 mg (100%) of compound 57B as a white foam.

Step C:

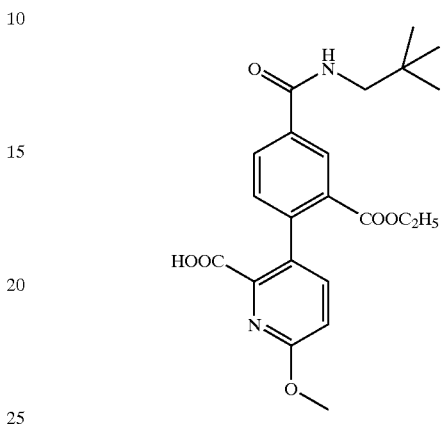
(57C)

To 380 mg (0.92 mmol) of compound 57B were added 607 mg (6.7 mmol) of $NaClO_2$, 235 mg (1.83 mmol) of $NaH_2PO_4$, and 2 ml 2-methylbutene, and the mixture was stirred for 1 h at 0° C. in 15 ml of t-BuOH/$CH_3CN$/$H_2O$ (6:1:2). The reaction mixture was poured into 30 ml of ice water. The combined organic layers were extracted with EtOAc (3×15 ml), washed with brine, dried over $Na_2SO_4$, and concentrated to yield 382 mg (100%) of compound 57C as a white foam. HPLC-purity 99%, IR.

Step D:

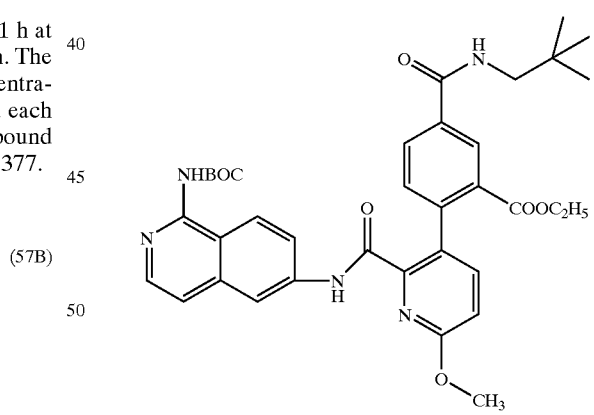
(57D)

207 mg (0.50 mmol) of compound 57C, 130 mg (0.50 mmol) of

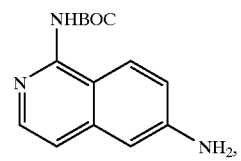

118 mg (0.55 mmol) of DCC, 20 mg of HOBT, and 10 mg of DMAP were dissolved in 20 ml acetonitrile and stirred at rt. After 24 h, the reaction was completed (per HPLC). Filtration and concentration yielded 307 mg (93.6%) of crude compound 57D as a white solid. HPLC-purity=83%. This material was directly used in the next step without further purification. MS (M+H)$^+$=656.

Step E

EXAMPLE 57

Compound 57D was dissolved in 6 ml TFA/DCM and stirred for 4 h at 5° C. to complete the deprotection. Concentration and purification of the oily residue of crude product by prep-HPLC yielded 128 mg (47% over two steps) of Example 57 in the TFA salt form HPLC-purity= 100%, MS (M+H)=556.

EXAMPLES 58–69

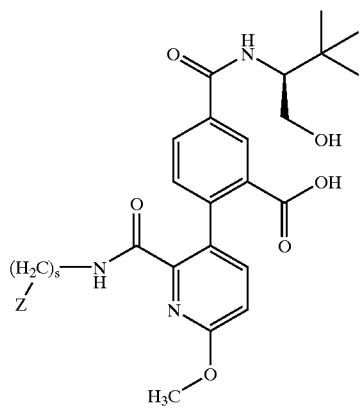

(Ij)

Compounds having formula (Ij), above, wherein s and Z have the values listed below in Table 7 below, were prepared using the following procedure.

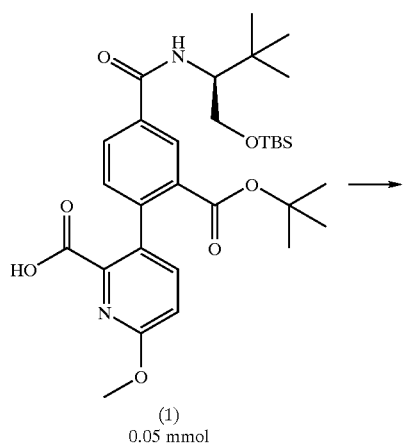

(1)
0.05 mmol

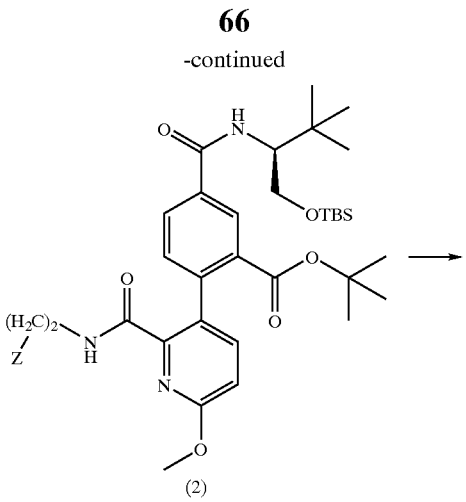

(2)

Compounds of Formula (Ic), above.

Compound 1 was dissolved in acetonitrile with 2 equivalents of an amine having the desired groups —(CH$_2$)$_s$—Z. EDCI and HOBT were added and the mixture was stirred overnight. The reaction mixture was added to SCX resin, and it was then washed with 1.5 ml of CH$_3$CN and eluted with 1.5 ml of CH$_3$CN/MeOH (1:1). The solvent was removed to afford the compound 2. To compound 2 was added CH$_2$Cl$_2$/TFA (2:1), and the mixture was allowed to stand for 2.5 h. After evaporation of the solvent, MeOH and NH$_4$OH were added and the compounds of Formula (Ij) were isolated following purification by RP HPLC, using MeOH/water as eluent.

TABLE 7

| Ex. | s | Z | MS (M + H)$^+$ |
|---|---|---|---|
| 57 | 0 | 3-(methylthio)phenyl | 538 |
| 58 | 0 | 3-(acetyl)phenyl | 534 |
| 59 | 0 | quinolin-6-yl | 543 |
| 60 | 0 | benzothiazol-6-yl | 549 |

TABLE 7-continued

| Ex. | s | Z | MS (M + H)+ |
|---|---|---|---|
| 61 | 0 | 2,2-difluorobenzo[1,3]dioxol-5-yl | 572 |
| 62 | 1 | cyclohexyl | 512 |
| 63 | 0 | naphth-2-yl | 542 |
| 64 | 0 | 3-carbamoylphenyl | 535 |
| 65 | 1 | 3-chloro-4-methylphenyl | 554/556 |
| 66 | 0 | 4-amino-2-methylquinazolin-7-yl | 573 |
| 67 | 0 | 1-methylaminoisoquinolin-6-yl | 572 |
| 68 | 0 | 1-aminoisoquinolin-7-yl | 558 |
| 69 | 0 | 1-aminoisoquinolin-5-yl | 558 |

EXAMPLE 70–160

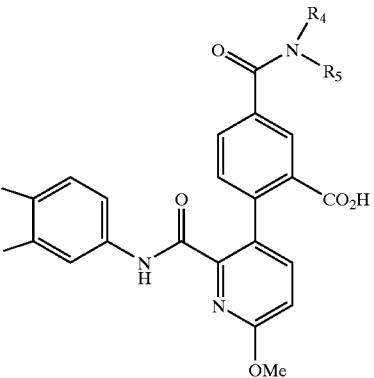
(Ik)

Compounds having the formula (Ik), wherein the groups $R_4$ and $R_5$ have the values listed in Table 8, were prepared using the method of Steps A through I below.

Step A:

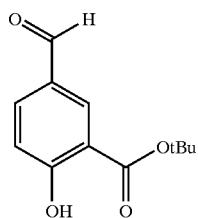
(70A)

tBuOH (90 mL) was added to a flask with 5-formylsalicyclic acid

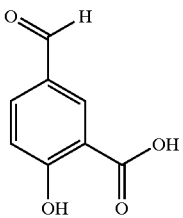

(4.98 g, 30.00 mmol) and DMAP (150 mg, 1.23 mmol). The salicyclic acid did not completely dissolve. A solution of DCC (6.50 g, 31.50 mmol) in THF (60 mL) was added dropwise over 30 min. After 12 h, Et$_2$O (50 mL) was added followed by anhydrous oxalic acid (4.41 g, 48.98 mmol). After 15 min of stirring, the solids were filtered off. The filtrate was washed with 2.5% NaHCO$_3$ (3×) and sat. NaCl (2×). The solution was dried (MgSO$_4$), filtered, and conc. to give 6.20 g (93% crude) of compound 70A.

Step B:

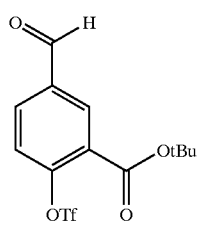
(70B)

Pyridine (11.52 mL, 135.10 mmol) was added to a solution of compound 70A (6.00 g, 27.02 mmol) in DCM (40 mL) at −10° C. A solution of trifluoromethanesulfonic anhydride (9.09 mL, 54.04 mmol) in DCM (10 mL) was added dropwise over 15 min. The reaction mixture was stirred for 1.5 h at −10° C. and then stored in the freezer. The next day, the solution was poured into cold H$_2$O (120 mL), then partitioned between EtOAc (250 mL) and H$_2$O (100 mL). The aqueous phase was isolated and extracted with EtOAc (100 mL). All organic phases were combined and washed with sat. NaCl(2×). The solution was dried (MgSO$_4$), filtered and conc. The crude product was purified by flash chromatography using DCM:Hexane (1:2) to obtain 7.96 g (83%) of compound 70B.

Step C:

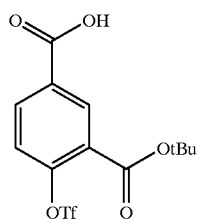
(70C)

2-methyl-2-butene (9.6 mL) was added to a solution of compound 70B (5.66 g, 15.98 mmol) in tBuOH:CH$_3$CN:H$_2$O (6:1:2) (85 mL) at 0° C. NaClO$_2$ (6.21 g, 68.69 mmol) was added in portions over 1 min. After 5 min of stirring, NaH$_2$PO$_4$ H$_2$O (2.65 g, 19.18 mmol) was added in portions over 1 min. The reaction mixture was then stirred at rt for 45 min and cold H$_2$O (125 mL) was added. The solution was extracted with EtOAc (2×250 mL). The organic extracts were combined and washed with H$_2$O (2×) and sat. NaCl(2×). The solution was dried (MgSO$_4$), filtered, and conc. to give 4.80 g (81%) of Compound 70C.

Step D:

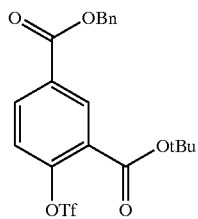
(70D)

Compound 70C (4.80 g, 12.96 mmol) was dissolved in DMF (10 mL). NaHCO$_3$ (1.31 g, 15.55 mmol) was added followed by benzyl bromide (6.17 mL, 51.85 mmol). After 12 h, the reaction mixture was partitioned between EtOAc (250 mL) and H$_2$O (150 mL). The organic phase was isolated and washed with sat. NaCl (1×). The solution was dried (MgSO$_4$), filtered, and conc. The crude product was purified by flash chromatography using a gradient of 3% to 20% EtOAc in hexane to provide 4.64 g (78%) of compound 70D.

Step E:

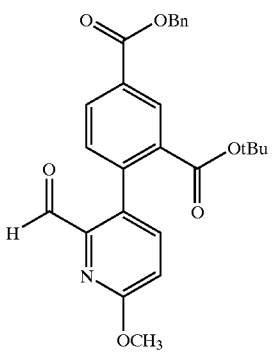
(70E)

Deoxygenated DMF (45 mL) was added to a round bottom flask containing compound 70D (4.44 g, 9.64 mmol) and stannene $$\text{(structure: pyridine-2-carboxaldehyde with Sn(Bu)}_3\text{ and OCH}_3\text{)}$$

(5.34 g, 12.54 mmol) (see WO 99/41231 and the general procedure for stannylation of pyridine carboxyaldehydes described in *J. Heterocyclic Chem.*, Vol 31, (1994) at p. 1161.) Powdered CuO (0.77 g, 9.64 mmol) was added followed by dichlorobis-(triphenylphosphine)palladium(II) (0.46 g, 0.65 mmol). The mixture was heated to 110° C. After 1 h, the reaction mixture was cooled to rt. The solution was diluted with EtOAc (45 mL) and filtered through Celite. The filtrate was partitioned between EtOAc (150 mL) and H$_2$O (150 mL). The organic phase was isolated, washed with sat. NaCl (100 mL), dried (MgSO$_4$), and conc. The crude material was purified by column chromatography using hexane:DCM (1:2) to obtain 2.71 g (63%) of Compound (70E).

Step F:

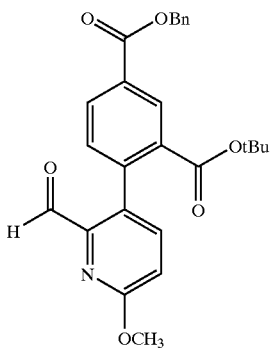
(70F)

The process of Step C, above, was followed, adding 3.65 mL of 2-methyl-2-butene to a solution of compound 70E (2.71 g, 6.06 mmol) in 33 mL of tBuOH:CH$_3$CN:H$_2$O (6:1:2), and using 2.36 g (26.04 mmol) of NaClO$_2$, 1.00 g (7.27 mmol) of NaH₂PO₄H₂O, and stirring the reaction for 30 min before adding cold H₂O (90 mL). The aq. solution was extracted with EtOAc (150 mL), and the organic extract washed with H₂O (2×) and sat. NaCl (2×), dried (MgSO₄), filtered, and conc. to give 2.85 g (100%) of compound 70F.

Step G:

(70G)

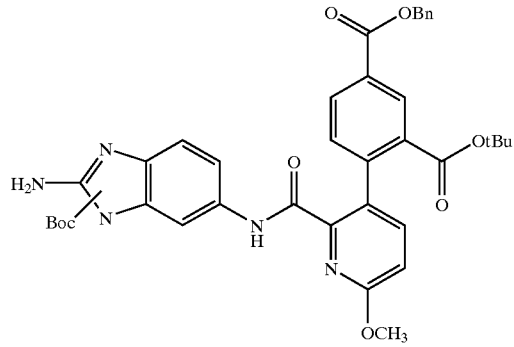

HOAt (83 mg, 0.61 mmol) was added to a solution of compound 70F (2.83 g, 6.11 mmol) and

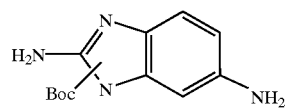

(1.52 g, 6.11 mmol) in DMF (30 mL). EDAC (1.52 g, 7.94 mmol) was added followed by DMAP (75 mg, 0.61 mmol). After 3 h, the reaction mixture was partitioned between EtOAc (400 mL) and H₂O (300 mL). The aqueous phase was isolated and extracted with EtOAc (100 mL). All organic extracts were combined, washed with sat. NaCl (2×), dried (MgSO₄), and conc. The crude product was purified by column chromatography using EtOAc to obtain 3.58 g (85%) of compound 70G.

Step H:

(70H)

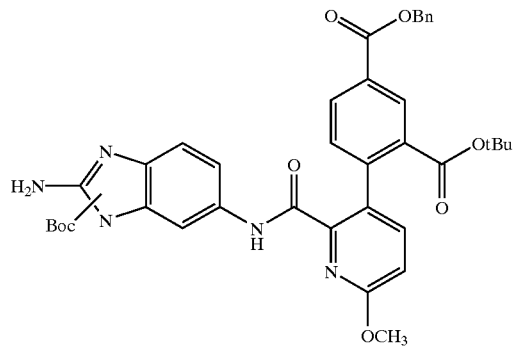

20% Pd(OH)₂ (1.75 g) was added to a solution of compound 70G (3.52 g, 5.07 mmol) in THF (60 mL). The solution was placed on a Parr apparatus at 50 p.s.i. After 48 h, the solution was diluted with THF:MeOH (1:1) and filtered. The catalyst was rinsed several times. The filtrate was conc. to give 1.90 g (62%) of compound 70H.

Step I

PROCEDURE FOR EXAMPLES 70–160 HAVING FORMULA Ik, ABOVE (TABLE 8)

A TECAN liquid handler was used to add 35 μL of DMF to each of a number of reaction tubes (12 mm×65 mm) in a mini-reactor. Then, to each reaction tube was added 144 μL (0.036 mmol) of a 2.5 M solution of an amine in DMF, the amine having the desired groups R₄ and R₅. Insoluble amines were added by hand. 5.1 μL (0.037 mmol) of TEA was added by hand to any tubes which contained an amine salt. The TECAN was then used to add 150 μL (18 mg, 0.030 mmol) of a stock solution of scaffold Compound 70H in DMF. This addition was followed by 150 μL of a stock solution containing 5.2 μL (0.033 mmol) of DIC and 4.5 mg (0.033 mmol) of HOAt in DMF. The tubes were sealed and shaken for 24 h.

The reaction mixtures were purified by solid phase extraction using a SCX cation exchange column (CUBCXHL5R3, 500 MG/3 ML/50 PKG) as follows:

1) Columns were conditioned with MeOH (2×1.5 mL);
2) Reaction mixtures were loaded on to SCX columns;
3) SCX columns were washed with MeOH (2×1.5 mL) and 0.1 M NH₃/MeOH (1.0 mL);
4) Columns were eluted with 2.0 M NH₃/MeOH (1.5 mL) into microtubes (9×80 mm); and
5) The microtubes were concentrated by speed vac.

0.5 mL of a TFA/DCM (1:2) solution was added to each microtube. The tubes were capped and shaken for 3 h and then concentrated by speed vac. All crude products were purified by PREP HPLC using a gradient of 35 to 100% solvent B (i.e., 90%MeOH, 10% H₂O, with 0.1% TFA), over 5 min at 20 mL/min (column: Shimadzu VP-ODS 20×50 mm). Fractions containing products were concentrated by speed vac. Compounds obtained in TFA salt form are reported in Table 8.

TABLE 8

| Ex. | R₄ | R₅ | MS (M + H)⁺ |
|---|---|---|---|
| 70 | H | H | 447 |
| 71 | H | ⟨C(CH₃)₃ group⟩ | 531 |

TABLE 8-continued
| Ex. | R4 | R5 | MS (M + H)+ |
|---|---|---|---|
| 72 | H | 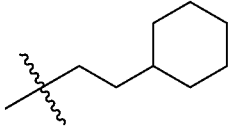 | 557 |
| 73 | H | 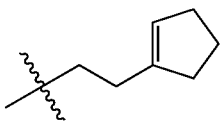 | 541 |
| 74 | H | 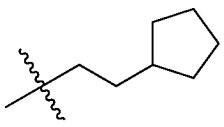 | 543 |
| 75 | H | 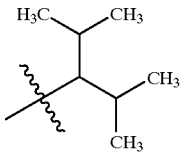 | 545 |
| 76 | H | 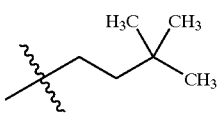 | 531 |
| 77 | H | 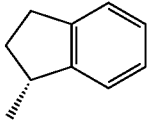 | 563 |
| 78 | H | 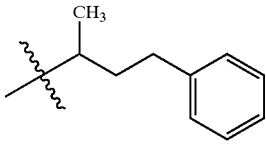 | 579 |
| 79 | H | 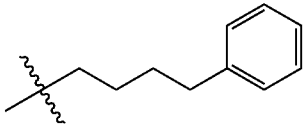 | 579 |
| 80 | H | 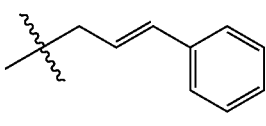 | 563 |
| 81 | H | 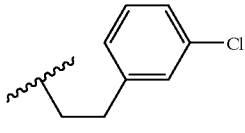 | 585 |
| 82 | H | 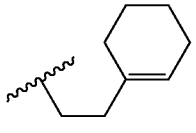 | 555 |

TABLE 8-continued
| Ex. | R$_4$ | R$_5$ | MS (M + H)$^+$ |
|---|---|---|---|
| 83 | H | 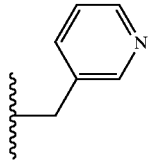 | 538 |
| 84 | H | 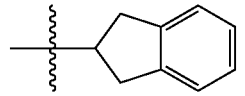 | 563 |
| 85 | H | 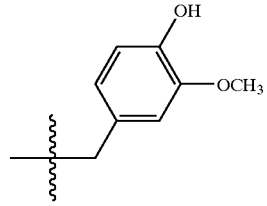 | 583 |
| 86 | H | 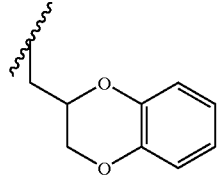 | 595 |
| 87 | H | 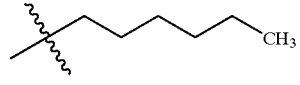 | 531 |
| 88 | H | 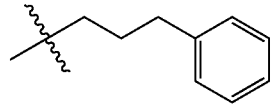 | 565 |
| 89 | H | 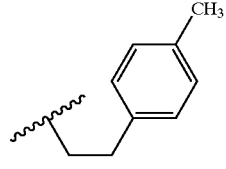 | 565 |
| 90 | H | 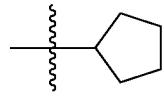 | 515 |
| 91 | H | 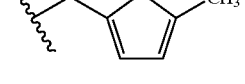 | 541 |
| 92 | H | 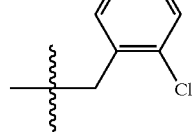 | 571 |

TABLE 8-continued
| Ex. | R₄ | R₅ | MS (M + H)⁺ |
|---|---|---|---|
| 93 | H | 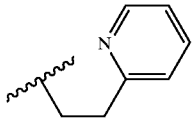 | 552 |
| 94 | H | 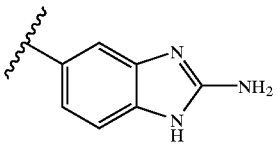 | 545 |
| 95 | H | 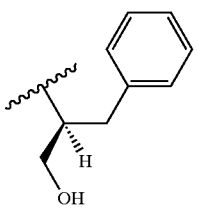 | 581 |
| 96 | H | 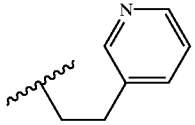 | 552 |
| 97 | H | 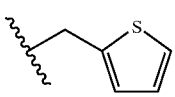 | 543 |
| 98 | H | 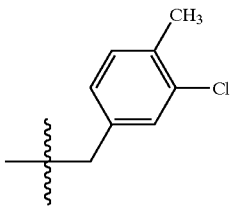 | 585 |
| 99 | H | 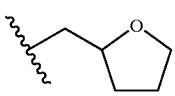 | 531 |
| 100 | H | 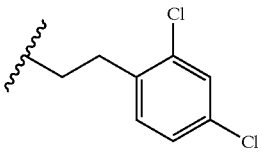 | 619 |
| 101 | H | 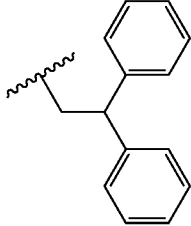 | 627 |

TABLE 8-continued
| Ex. | R$_4$ | R$_5$ | MS (M + H)$^+$ |
|---|---|---|---|
| 102 | H | 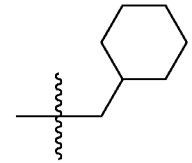 | 543 |
| 103 | H | 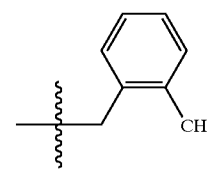 | 551 |
| 104 | H | 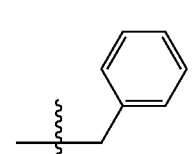 | 537 |
| 105 | H | 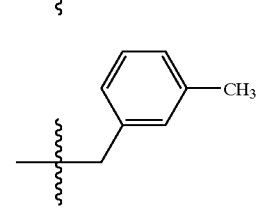 | 551 |
| 106 | H | 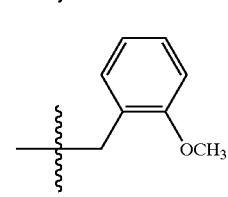 | 581 |
| 107 | H | 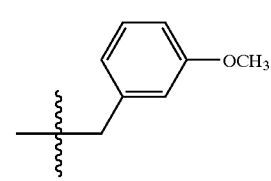 | 581 |
| 108 | H | 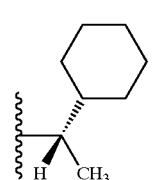 | 557 |
| 109 | H | 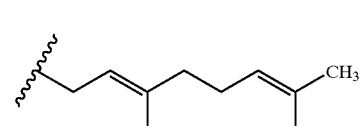 | 583 |
| 110 | H | 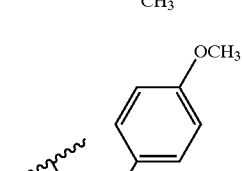 | 581 |

TABLE 8-continued
| Ex. | R$_4$ | R$_5$ | MS (M + H)$^+$ |
|---|---|---|---|
| 111 | H | 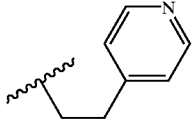 | 552 |
| 112 | H | 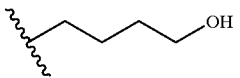 | 519 |
| 113 | H | 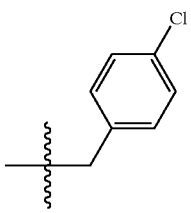 | 571 |
| 114 | H | 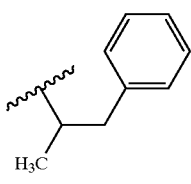 | 565 |
| 115 | H | 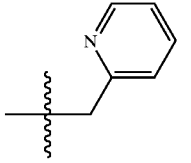 | 538 |
| 116 | H | 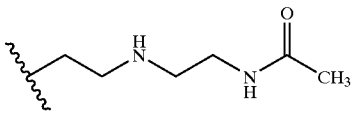 | 532 |
| 117 | H | 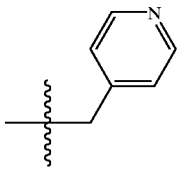 | 538 |
| 118 | H | 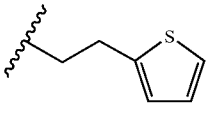 | 557 |
| 119 | H | 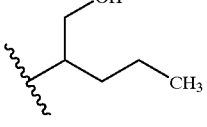 | 533 |
| 120 | H | 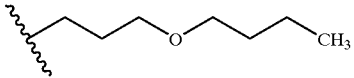 | 561 |

TABLE 8-continued

| Ex. | R$_4$ | R$_5$ | MS (M + H)$^+$ |
|---|---|---|---|
| 121 | H | 4-methylcyclohexyl | 543 |
| 122 | H | 3-(3,4-dimethoxyphenyl)propyl | 611 |
| 123 | H | 2-ethylhexyl | 559 |
| 124 | H | 4-methylpentyl | 517 |
| 125 | H | 3-phenoxypropyl | 567 |
| 126 | H | 4-heptyl | 545 |
| 127 | H | pentyl | 503 |
| 128 | H | 3-(4-sulfamoylphenyl)propyl | 630 |
| 129 | H | 2-methylcyclohexyl | 543 |
| 130 | H | 3-methylcyclohexyl | 543 |
| 131 | H | 4-propoxybutyl | 547 |

TABLE 8-continued
| Ex. | R4 | R5 | MS (M + H)+ |
|---|---|---|---|
| 132 | H | 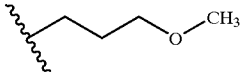 | 519 |
| 133 | H | 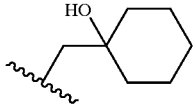 | 559 |
| 134 | H | 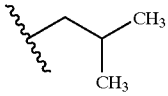 | 503 |
| 135 | H | 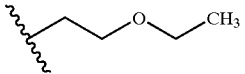 | 519 |
| 136 | H | 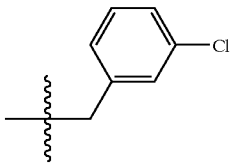 | 571 |
| 137 | H | 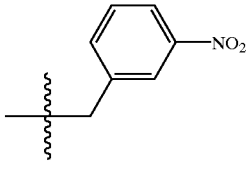 | 582 |
| 138 | H | 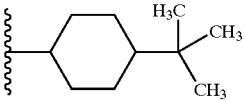 | 585 |
| 139 | H | 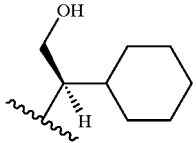 | 587 |
| 140 | H | 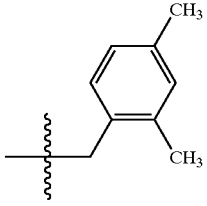 | 565 |
| 141 | H | 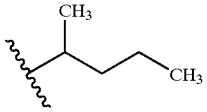 | 517 |

TABLE 8-continued
| Ex. | R₄ | R₅ | MS (M + H)⁺ |
|---|---|---|---|
| 142 | H | 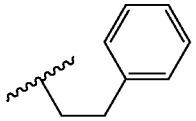 | 551 |
| 143 | H | 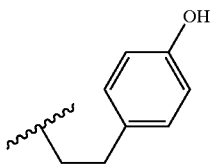 | 567 |
| 144 | H | 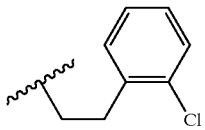 | 567 |
| 145 | H | 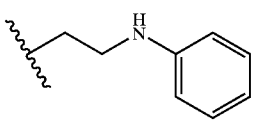 | 564 |
| 146 | H | 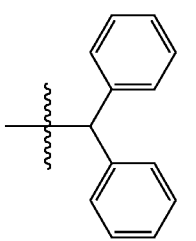 | 613 |
| 147 | H | 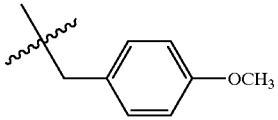 | 567 |
| 148 | H | 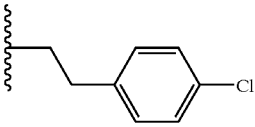 | 585 |
| 149 | H | 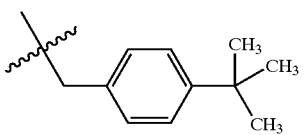 | 593 |
| 150 | H | 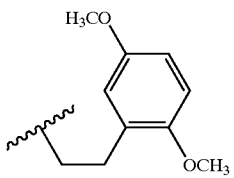 | 611 |
| 151 | —CH₃ | 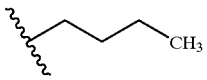 | 517 |

TABLE 8-continued

| Ex. | R₄ | R₅ | MS (M + H)⁺ |
|---|---|---|---|
| 152 | —(CH₂)₂OH | (n-pentyl) | 561 |
| 153 | —CH₃ | (benzyl) | 551 |
| 154 | —(CH₂)₂CH₃ | (isobutyl) | 545 |
| 155 | —(CH₂)₂OH | (benzyl) | 581 |
| 156 | —(CH₂)₂OH | (cyclohexyl) | 573 |
| 157 | —CH₃ | (2-(pyridin-2-yl)ethyl) | 566 |
| 158 | —(CH₂)₂CH₃ | (2-methoxyethyl) | 547 |
| 159 | —(CH₂)₂OH | (n-butyl) | 547 |
| 160 | —CH₃ | (isobutyl) | 517 |

EXAMPLES 161–170

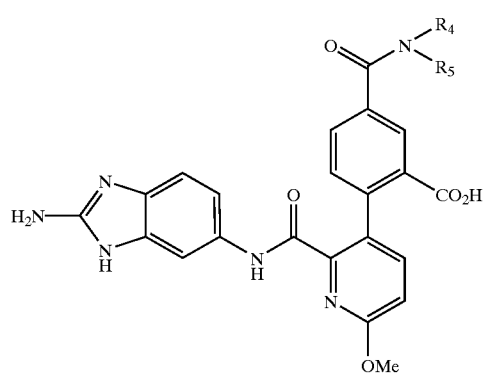

(II)

Compounds having the formula (II), wherein the groups R₄ and R₅ together with nitrogen atom to which they are attached form the optionally-substituted heterocyclic and heteroaryl rings listed in Table 9, were prepared using the method of Examples 70–160 described above.

TABLE 9

| Ex. | —NR₄R₅ | MS (M+ H)⁺ |
|---|---|---|
| 161 | (3-hydroxypyrrolidin-1-yl) | 517 |

TABLE 9-continued

| Ex. | —NR₄R₅ | MS (M+ H)⁺ |
|---|---|---|
| 162 | morpholine | 517 |
| 163 | 2-(hydroxymethyl)pyrrolidine | 531 |
| 164 | 3,5-dimethylpiperidine | 543 |
| 165 | 4-benzylpiperidine | 605 |
| 166 | piperidine | 515 |
| 167 | decahydroquinoline | 569 |
| 168 | 1,2,3,4-tetrahydroisoquinoline | 563 |
| 169 | 4-hydroxypiperidine | 531 |
| 170 | 4-(2-phenylethyl)piperidine | 633 |

EXAMPLE 171

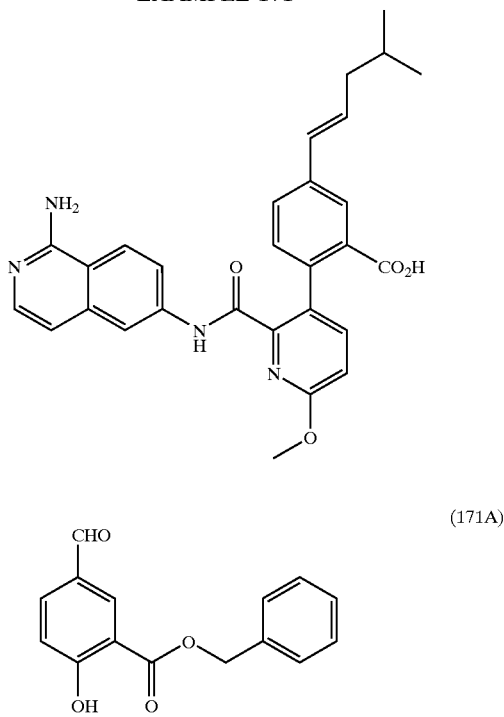

Step A:

(171A)

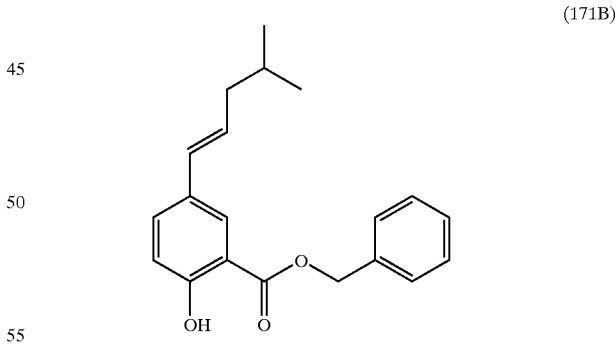

A mixture of 3.6 g (21 mmol) of 5-formylsalicylic acid, 11 g (65 mmol) of benzylbromide, and 3.1 g (43 mmol) of NaHCO₃ in 40 mL of acetone was stirred for 24 h at reflux, then cooled to rt and concentrated. The residue was taken up with EtOAc and washed with sat'd NaHCO₃. The organic layer was dried over Na₂SO₄ and concentrated to give 3.6 g (65%) of compound 171A as a pale yellow oil. $^1$H-NMR (500 MHz), $\delta$11.3 (s,1H,OH), 9.85 (s, 1H, CHO), 8.37 (d, 1H, ArH), 7.43 (d, 1H, ArH), 7.46–7.45 (m, 5H, ArH's), 7.09 (d, 1H, ArH), 5.41 (s, 2H, CH₂Ph).

Step B:

(171B)

To a suspension of 4 g (9.7 mmol) of isoamyl triphenylphosphonium bromide in 40 mL of THF at −78° C. was added 4.7 mL (11.7 mmol) of 2.5 M butyllithium in hexane dropwise. The mixture was stirred for 20 min at −78° C., 1 h at 0° C., then recooled to −78° C. A solution of compound 171A in 15 mL of THF was added dropwise. The resulting solution was stirred for 1 h at −78° C., then warmed to rt overnight and concentrated. The residue was taken up with EtOAc and washed with brine and 1 N HCl. The organic layer was dried over MgSO₄ and concentrated. The residue was chromatographed over silica gel (EtOAc:hexane, 1:9) to give 0.8 g (66%) of compound 171B as a pale yellow oil. ¹H-NMR (500 MHz), δ10.6 (1H, s, OH), 7.78 (s, 1H, ArH), 7.49 (dd, 1H, ArH), 7.44–7.39 (m, 5H, ArH's), 6.90 (d, 1H, ArH), 6.25 (d, 1H, CH=CH), 6.05 (dt, 1H, CH=CH), 5.37 (s, 2H, CH₂Ph), 2.08, (dt, 2H, C=CCH₂), 1.67 (dq, 1H, CHMe₂), 0.90 (d, 6H, (CH₃)₂).

Step C:

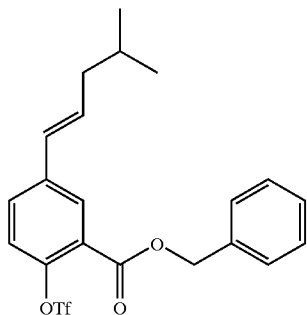

(171C)

To a solution of 0.3 g (0.9 mmol) of compound 171B in 20 mL of DCM was added 0.11 g (1.1 mmol) of TEA and 0.31 g (1.1 mmol) of trifluorosulfonic anhydride at 0° C. The solution was stirred for 4 h at 0° C., warmed to rt overnight, diluted with DCM, and washed with brine and sat'd NaHCO₃. The organic layer was dried over MgSO₄ and concentrated. The residue was passed through a short bed of silica gel. The filtrate was concentrated to give 0.35 g (85%) of compound 171C as a pale yellow oil.

Step D:

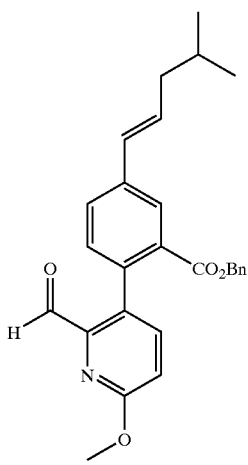

(171D)

A mixture of 0.35 g (0.8 mmol) of compound 171C, 0.48 g (1.1 mmol) of 6-methoxy-3-tributylstannanyl-pyridine-2-carbaldehyde, 80 mg (0.1 mmol) of dichlorobis(triphenylphosphine)palladium(II), and 90 mg (1.1 mmol) of cupric oxide in 20 mL of DMF was stirred for 6 h at 80° C. The mixture was cooled to rt, 30 mL of sat'd KF solution was added, and the solution was stirred for 1 h at rt. The mixture was filtered, the filtrate extracted with EtOAc, and the organic layer dried over MgSO₄ and concentrated. The residue was chromatographed over silica gel (EtOAc:hexane, 3:7) to give 0.16 g (47%) of compound 171D. ¹H-NMR (400 MHz), δ9.76 (s, 1H, CHO), 8.03 (s, 1H, ArH), 7.51 (dd, 1H, ArH), 7.37 (d, 1H, ArH), 7.28–7.10 (m, 5H, ArH's), 7.07 (d, 1H, ArH), 6.81 (d, 1H, ArH), 6.41 (d, 1H, CH=), 6.32 (dd, 1H, =CH), 5.04 (d, 2H, OCH₂), 4.00 (s, 3H, OCH₃), 2.11 (m, 2H, =CCH₂), 1.73 (m, 1H, CHMe₂), 0.93 (d, 6H, (CH₃)₂).

Step E:

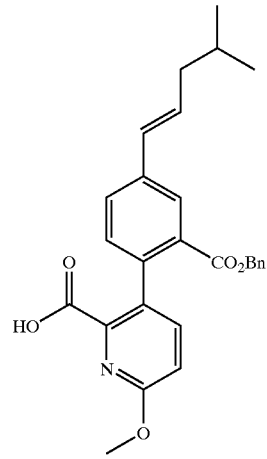

(171E)

To a solution of 80 mg (0.2 mmol) of compound 171D in a 10 mL solution of t-butanol:acetonitrile:water (6:1:2), was added 55 mg (0.60 mmol) of sodium chlorite, 33 mg (0.24 mmol) of NaH₂PO₄.H₂O, and 0.1 mL of 2-methyl-but-2-ene at 0° C. The solution was stirred for 30 min at 0° C., 2 h at rt, and concentrated. The residue was taken up with EtOAc and washed with brine. The organic layer was dried over MgSO₄ and concentrated to give the above titled compound as a yellow oil. MS, m/z (M+1)⁺=446.

Step F

EXAMPLE 171

To a solution of the acid from Step E in 5 mL of DCM and 5 mL of DMF was added 25 mg (80 mmol) of N1-(2.4-dimethoxy-benzyl)-isoquinoline-1,6-diamine, 17 mg (88 mmol) of EDAC, 1 mg (9 mmol) of HOAT, and 1 mg (9 mmol) of DMAP. The solution was stirred for 12 h at rt and concentrated and the residue taken up with 5 mL of anisole and 5 mL of TFA. The solution was then stirred for 18 h at rt and concentrated and the residue taken up with 10 mL of MeOH. Next, 0.2 g (3.5 mmol) of KOH was added to the solution, and it was stirred for 4 h at rt, then neutralized with 1N HCl and concentrated. The residue was purified with HPLC using YMC S5 ODS 20×100 column to give 22 mg of Example 171 as a white lyophalate. MS, m/z (M+1)⁺= 497. ¹H-NMR (500 MHz), δ8.32(s, 2H, ArH's), 8.01 (s,1H, ArH), 7.90 (d, 1H, ArH), 7.60 (d, 1H, ArH), 7.57 (d, 1H, ArH), 7.45 (d, 1H, ArH), 7.17 (d, 1H, ArH), 7.09 (d, 1H, ArH), 7.06 (d, 1H, ArH), 6.47 (d, 1H, CH=C), 6.38 (dt, 1H, C=CH), 4.09 (s, 3H, CH₃), 2.13 (m, 2H, =CCH₂), 1.68 (m, 1H, CHMe₂), 0.90 (d, 6H, (CH₃)₂).

EXAMPLE 172

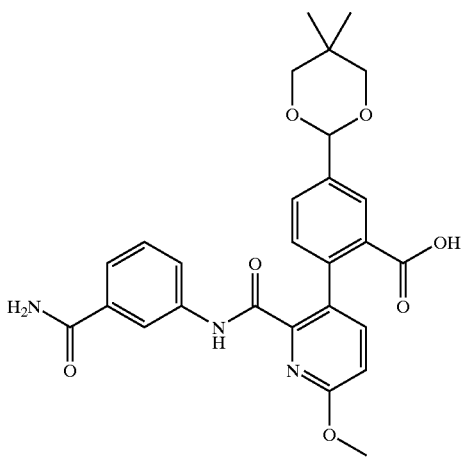

Step A:

(172A)

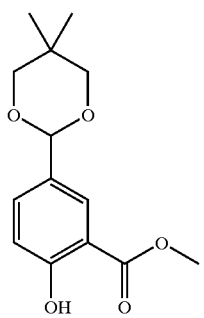

To a solution of 6.5 g (36 mmol) of 5-formyl-2-hydroxybenzoic acid methyl ester in 80 mL of benzene was added 0.68 g of toluenesulfonic acid and 4.5 g (43 mmol) of 2,2-dimethyl-1,3-propanediol at rt. The solution was stirred for 6 h at reflux with continuous removal of water, then cooled to rt and concentrated. The residue was chromatographed with silica gel (EtOAc:hexane, 1:9) to give 5.3 g (55%) of compound 172A as a pale yellow oil.

Step B:

(172B)

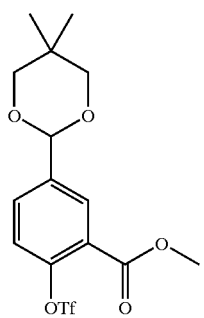

To a solution of 5.3 g (20 mmol) of compound 172A was added 6.3 g (22 mmol) of trifluoromethylsulfonic anhydride and 2.3 g (22 mmol) of TEA. The solution was stirred for 18 h at rt and washed with brine and sat'd NaHCO₃ solution. The organic layer was dried over MgSO₄ and concentrated. The residue was chromatographed over silica gel (EtOAc:hexane, 1:9) to give 6.5 g (77%) of compound 172B as a dark oil. ¹H-NMR (400 MHz), δ8.21 (d, 1H, ArH), 7.78 (dd, 1H, ArH), 7.30 (d, 1H, ArH), 5.43 (s, 1H, OCHO), 3.97 (s, 3H, OCH₃), 3.79 (d, 2H, OCH₂), 3.66 (d, 2H, OCH₂), 1.27 (s, 3H, CH₃), 0.82 (s, 3H, CH₃).

Step C:

(172C)

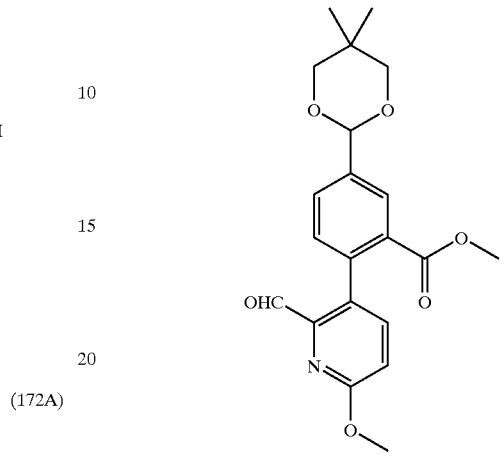

A mixture of 6.5 g (16.3 mmol) of compound 172B, 7.6 g (17.9 mmol) of 6-methoxy-3-tributylstannanyl-pyridine-2-carbaldehyde, 1.3 g (1.79 mmol) of dichlorobis(triphenylphosphine)palladium(II), and 1.4 g (17.9 mmol) of cupric oxide in 40 mL of DMF was stirred for 6 h at 80° C. The mixture was cooled to rt, then 50 mL of sat'd KF solution was added and the solution stirred for 1 h. The mixture was filtered, the filtrate extracted with EtOAc, and the organic layer was dried over MgSO₄ and concentrated. The residue was chromatographed over silica gel (EtOAc:hexane, 3:7) to give 2.8 g (44%) of compound 172C. ¹H-NMR (500 MHz), δ9.81 (s, 1H, CHO), 8.19 (d, 1H, ArH), 7.71 (dd, 1H, ArH), 7.41 (d, 1H, ArH), 7.22 (d, 1H, ArH), 6.94 (d, 1H, ArH), 5.47 (s, 1H, OCHO), 4.05 (s, 3H, OCH₃), 3.79 (d, 2H, OCH₂), 3.67 (d, 2H, OCH₂), 3.66 (s, 3H, OCH₃), 1.27 (s, 3H, CH₃), 0.81 (s, 3H, CH₃).

Step D:

(172D)

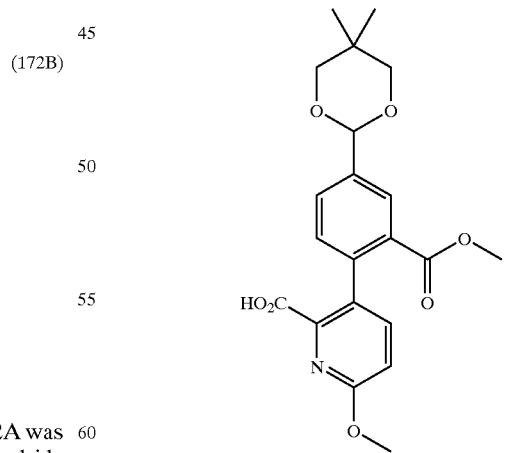

To a solution of 0.37 g (0.96 mmol) of compound 172C in a 20 mL solution of t-butanol:acetonitrile:water (6:1:2) was added 0.26 g (2.8 mmol) of sodium chlorite, 0.13 g (0.96 mmol) of NaH₂PO₄·H₂O, and 0.1 mL of 2-methyl-but-2-ene at 0° C. The solution was stirred for 30 min at 0°

C., 2 h at rt, and concentrated. The residue was taken up with EtOAc and washed with brine. The organic layer was dried over MgSO₄ and concentrated to give 0.30 g (78%) of compound 172D as a yellow oil. MS, m/z (M+1)⁺=402.

Step E

EXAMPLE 172

To a solution of compound 172D in 10 mL of DCM and 10 mL of DMF was added 0.15 g (1.2 mmol) of 3-amino-benzamide, 0.22 g (1.2 mmol) of EDAC, 15 mg (0.12 mmol) of HOAT, and 14 mg (0.12 mmol) of DMAP at rt. The solution was stirred for 12 h at rt and concentrated. The residue was then taken up with 20 mL of MeOH and 0.2 g (3.5 mmol) of KOH was added. The solution was stirred for 4 h at rt, neutralized with 1N HCl and concentrated. The residue was purified with HPLC using YMC S5 ODS 20×100 column to give 53 mg of Example 172 as a white lyophilate. MS, m/z (M+1)⁺=506. ¹H-NMR (500 MHz), δ9.86 (s, 1H, NH), 8.13 (s, 1H, ArH), 8.01 (S, 1H, ArH), 7.72 (dd, 1H, ArH), 6.67 (d, 1H, ArH), 7.53 (d, 1H, ArH), 7.45 (d, 1H, ArH), 7.35 (dd, 1H, ArH), 7.28 (d, 1H, ArH), 6.96 (d, 1H, ArH), 5.36 (s, 1H, OCHO), 4.04 (s, 3H, OCH₃), 3.79 (d, 2H, OCH₂), 3.68 (d, 2H, OCH₂), 1.28 (s, 3H, CH₃), 0.80 (s, 3H, CH₃).

EXAMPLE 173

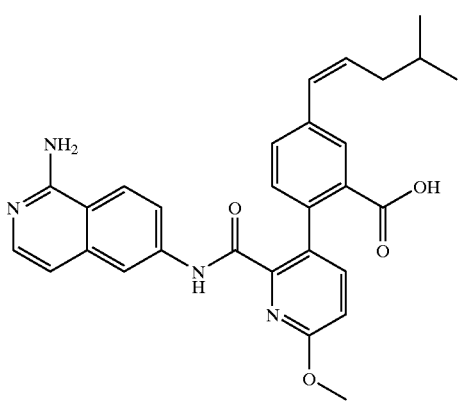

Step A:

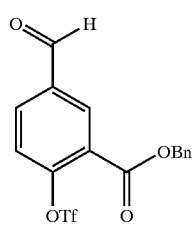

(173A)

2 g (7.8 mmol) of compound 171A from Example 171 was dissolved in 20 mL DCM with 1.7 mL (11.7 mmol) TEA. A solution of 1.97 mL (11.7 mmol) triflic anhydride in 15 mL DCM was slowly added to the phenol solution at 0° C. The solution was stirred at rt overnight and washed with a sat'd solution of NaHCO₃. The organic layer was dried and concentrated and the product purified by column chromatography (EtOAc/hexane, 3:7) to give 2.7 g (90%) of compound 173A. ¹H NMR (500 MHz), δ10.14 (s, 1H, CHO), 8.65 (s, 1H), 8.23 (d, 1H), 7.58–7.43 (m, 6H), 5.53 (s, 2H, CH₂).

Step B:

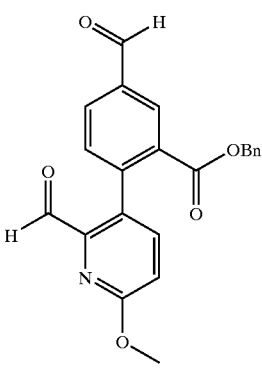

(173B)

2.7 g (7.0 mmol) of compound 173A was mixed with 2.9 g (7.0 mmol) of 6-methoxy-2-tributylstannyl-pyridine-3-carbaldehyde 492 mg (0.7 mmol) of PdCl₂(PPh₃)₂, and 553 mg (7.0 mmol) of cupric oxide in 20 mL N,N-DMF. The reaction was refluxed at 115° C. for 5 h. The mixture was cooled to rt and 20 mL of a sat'd solution of KF was added. The reaction was stirred for one hour at rt and then concentrated, and the residue was taken up in EtOAc and extracted with water. The organic layer was dried and concentrated. The product was chromatographed over silica gel (EtOAc/hexane, 3:7) to yield 347 mg (15%) of compound 173B.

Step C:

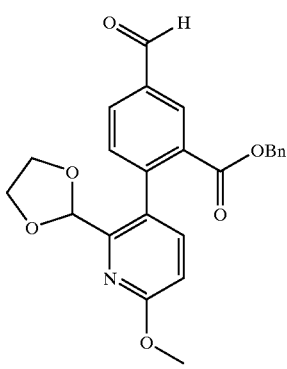

(173C)

347 mg (0.92 mmol) of compound 173B together with 0.04 mL (0.65 mmol) ethylene glycol, and 25 mg(0.13 mmol) p-Tos-OH was dissolved in 20 ml benzene. The mixture was stirred at reflux (85° C.) for 10 min. and was cooled to rt. The above product was chromatographed over silica gel (EtOAc/hexane, 3/7) to yield 175 mg (45%) of compound 173C.

Step D:

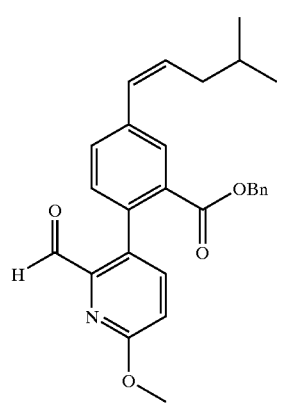

(173D)

To a suspension of 224 mg (0.54 mmol) isoamyl triphenylphosphonium bromide in 20 mL THF was added 0.3 mL (0.5 mmol) 1.6 M of butyl lithium in hexanes at −78° C. The suspension was stirred for one hour at 0° C. until it became a solution. A solution of 175 mg (0.42 mmol) of compound 173C in 10 mL THF was then added to the ylid solution at 0° C. and stirred for 1 h. The reaction was concentrated and the residue taken up in EtOAc and washed with a sat'd NaCl solution. The organic layer was dried and concentrated and the product purified by column chromatography (1/4 EtOAc/Hexane) to give 120 mg (60%) of the desired cis product. The ethylene glycol protecting group was removed by dissolving the compound in 20 mL THF/H$_2$O (10:1) and adding several drops of 1N HCl. The mixture refluxed at 70° C. for 1 h and was concentrated. The residue was taken up in EtOAc and washed with a sat'd solution of NaHCO$_3$. The organic layer was dried and concentrated to yield compound 173D.

Step E

EXAMPLE 173

The aldehyde from Step D was oxidized to a carboxylic acid by dissolving 115 mg (0.27 mmol) of the aldehyde, 97 mg (1.07 mmol) of sodium chlorite, and 0.13 mL of (1.21 mmol) 2-methyl-2-butene in 15 mL t-BuOH/CH$_3$CN/H$_2$O (6:1:2) at 0° C. After a solution formed, 56 mg (0.40 mmol) of NaH$_2$PO$_4$·H$_2$O was added. The reaction mixture was stirred for 2 h at rt and diluted with water. The organic layer was extracted with EtOAc, dried and concentrated to give a quantitative yield of the desired acid. The acid was then coupled to the 1-amino isoquinoline amine coupling component and deprotected as described in Example 171, step F, to give Example 173. $^1$H NMR (500 MHz), confirmed the cis product: δ8.25 (s, 1H, ArH), 8.24 (d, 1H, ArH), 7.90 (s, 1H, ArH), 7.85 (d, 1H, ArH), 7.53 (d, 1H, ArH), 7.38 (d, 1H, ArH), 7.37 (d, 1H, ArH), 7.14 (d, 1H, ArH), 6.99 (d, 1H, ArH), 6.97 (d, 1H, ArH), 6.45 (d, 1H, CH), 5.74 (m, 1H, CH), 4.05 (s, 3H, OCH$_3$), 2.20 (m, 2H, CH$_2$), 1.66 (m, 1H, CH), 0.88 (d, 6H, 2CH$_3$).

EXAMPLE 174

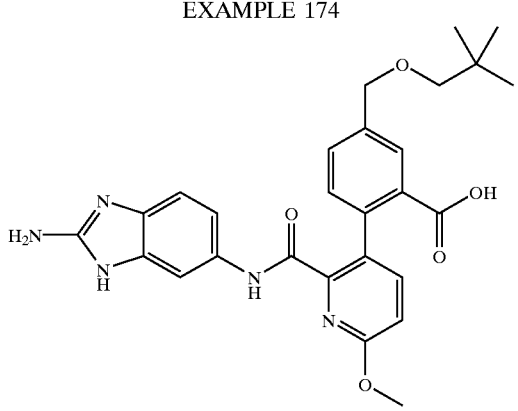

Step A:

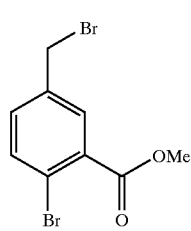

(174A)

A mixture of 2 g (8.7 mmol) of methyl 2-bromo-5-methylbenzoate, 1.86 g (10.4 mmol) of NBS, and 0.25 g (1.0 mmol) of benzoyl peroxide in 20 mL of CCl$_4$ was stirred for 2 h at reflux, cooled to rt and diluted with DCM. The solution was washed with sat'd NaHCO$_3$. The organic layer was dried over MgSO$_4$ and concentrated. The residue was chromatographed over silica gel (EtOAc:hexane, 1:9) to give 1.75 g (65%) of the compound 174A as a white solid. $^1$H NMR (500 MHz), δ7.80 (d, 1H, ArH), 7.62 (d, 1H, ArH), 7.34 (dd, 1H, ArH), 4.42 (s, 2H, CH$_2$Br), 3.93 (s, 3H, CH$_3$).

Step B:

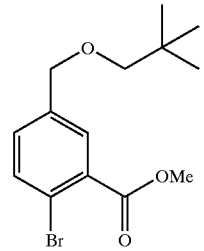

(174B)

To a solution of 215 mg (2.44 mmol) of neopentyl alcohol in 10 mL N,N-DMF was added 97 mg (4.05 mmol) of NaH. The mixture was stirred at rt for ½ h until a solution formed. A solution of 500 mg (1.62 mmol) of compound 174A in 10 mL is N,N-DMF was added and the mixture stirred at rt for 12 h and concentrated. The residue was taken up with EtOAc and washed with a sat'd solution of NaCl. The organic layer was dried over MgSO$_4$ and concentrated to give 170 mg (33%) of the coupled product. $^1$H NMR (500 mHz) δ7.87 (s, 1H, ArH), 7.63 (d, 1H, ArH), 7.33 (d, 1H, ArH), 4.42 (s, 2H, CH$_2$), 3.04 (s, 2H, CH$_2$), 1.17 (s, 9H, 3CH$_3$). To convert the benzoic acid to the above-titled protected methyl ester, the benzoic acid was dissolved in MeOH. Hydrochloric acid gas was bubbled into the solution. The flask was capped, the solution stirred for 4 h at rt, and the product concentrated under vacuum overnight. MS, m/z (M+1)$^+$=316.

Step C:

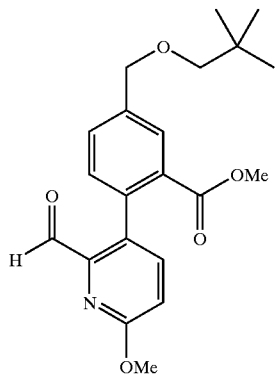

(174C)

A mixture of 170 mg (0.54 mmol) of compound 174B, 230 mg (0.54 mmol) of stannene (see Ex. 70, step 70E), 43 mg (0.54 mmol) cupric oxide, and 38 mg (0.054 mmol) of PdCl$_2$(PPh$_3$)$_2$ was dissolved in 10 mL of N,N-DMF, deoxygenated, and stirred at 115° C. for 4 h. The reaction mixture was cooled to rt and 10 mL of a sat'd solution of KF was added. The solution was stirred for 1 h, and then the reaction was concentrated and taken up in EtOAc and extracted. The organic layer was dried over MgSO$_4$ and concentrated to give 360 mg (82%) of crude compound 174C.

Step D

EXAMPLE 174

Compound 174C was converted to the corresponding 2-carboxylic acid using standard conditions. The acid was then coupled to the aminobenzimidazole amine-coupling component as in Example 70, step 70b, and deprotected using the DCM ITFA, (1:1) and saponification to give Example 174. ¹H NMR (500 MHz), δ7.98 (s, 1H, ArH), 7.86 (s, 1H, ArH), 7.56 (d, 1H, ArH), 7.53 (d, 1H, ArH), 7.25 (d, 1H, ArH), 7.21 (d, 1H, ArH), 7.02 (d, 1H, ArH), 4.58 (s, 2H, CH₂), 4.09 (s, 3H, OCH₃), 3.19 (s, 2H, CH₂), 0.94 (s, 9H, 3CH₃).

EXAMPLE 175

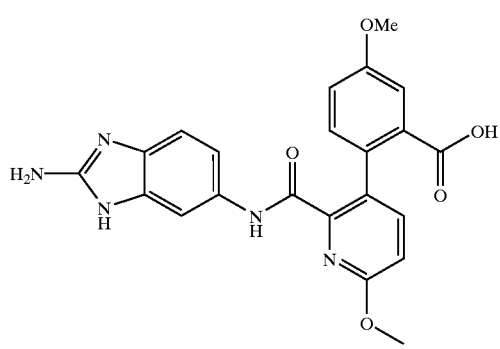

Step A:

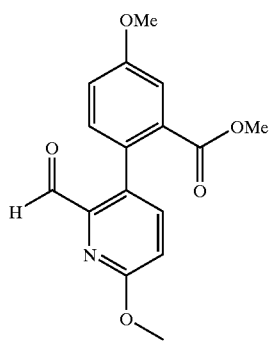

(175A)

250 mg (1.02 mmol) of methyl 2-bromo-5-methoxybenzoate, 433 mg (1.02 mmol) of stannene (see Ex. 173, step C), 70 mg (0.10 mmol) of PdCl₂(PPh₃)₂, and 80.6 mg (1.02 mmol) of cupric oxide were dissolved in 15 mL N,N-DMF. The mixture was deoxygenated and stirred at 115° C. for 5 h. The reaction was cooled to rt and 15 mL of a sat'd solution of KF was added. The reaction was stirred at rt for 1 h, concentrated, and the residue was taken up in EtOAc and extracted. The organic layer was dried over MgSO₄ and concentrated to yield the above aldehyde.

Step B

EXAMPLE 175

100 mg (0.33 mmol) of the aldehyde from Step A was oxidized to a carboxylic acid using conditions as described in Example 173, Step F. The acid was coupled to the amino benzimidazole amine-coupling component and deprotected following step D of Example 174 to give Example 175. ¹H NMR (500 MHz), δ7.78 (s, 1H, ArH), 7.47 (s, 1H, ArH), 7.45 (d, 1H, ArH), 7.18 (d, 1H, ArH), 7.17 (d, 1H, ArH), 7.06 (d, 1H, ArH), 7.05 (d, 1H, ArH), 6.92 (d, 1H, ArH), 3.99 (s, 3H, OCH₃), 3.77 (s, 2H, OCH₃).

EXAMPLE 176

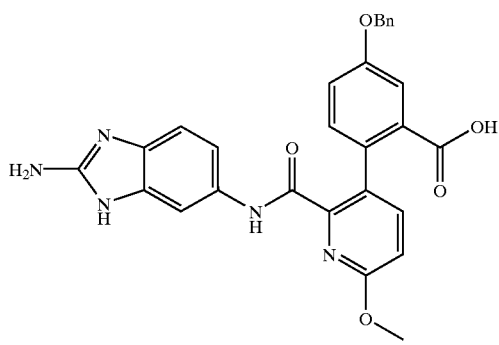

Step A:

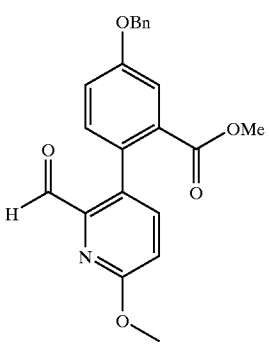

(176A)

A mixture of 0.7 g (2.2 mmol) of 5-benzyloxy-2-bromo-benzoic acid methyl ester [prepared according to Hoarau et al, *Synthesis,* Vol. 5 (2000) at pp. 655–66)], 0.93 g (2.2 mmol) of stannene (see step 173C), 0.15 g (0.2 mmol) of PdCl₂(PhPh₃)₂, and 0.17 g (2.2 mmol) of cupric oxide in 20 mL of N, N-DMF was stirred for 6 h at 80° C. The mixture was cooled to rt and 30 mL of sat'd KF solution was added. The mixture was stirred for 1 h at rt and then filtered. The filtrate was extracted with EtOAc, and the organic layer dried over MgSO₄ and concentrated. The residue was chromatographed over silica gel (EtOAc:hexane, 3:7) to give 0.51 g (61%) of compound 176A. ¹H NMR (400 MHz), δ9.83 (s, 1H, CHO), 7.67 (d, 1H, ArH), 7.46–7.32 (m, 7H, ArH's), 7.15 (dd, 1H, ArH), 6.94 (d, 1H, ArH), 5.13 (s, 2H, CH₂O), 4.07 (s, 3H, OCH₃), 3.64 (s, 3H, OCH₃).

Step B:

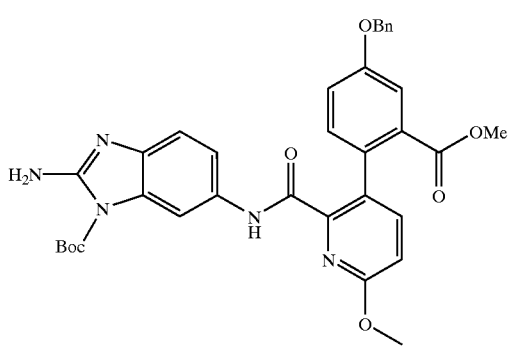

(176B)

400 mg (1.06 mmol) of compound 176A was oxidized to the corresponding 2-carboxylic acid and the acid was then coupled to the amino benzimidazole amine-coupling component following step D of Example 174 to provide compound 176B.

Step C

EXAMPLE 176

Compound 176B was deprotected with KOH in MeOH and water and subsequently TFA in DCM to provide Example 176. $^1$H NMR (500 MHz), δ7.78–6.91(13H, ArH's), 5.06 (s, 2H, CH$_2$), 3.99 (s, 3H, OCH$_3$).

EXAMPLE 177

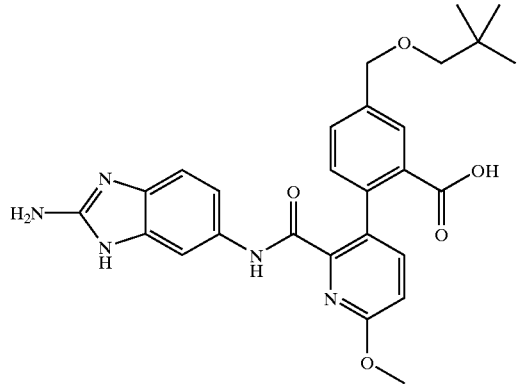

(177A)

Step A:

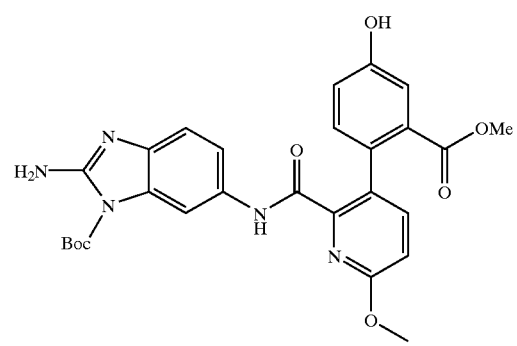

Compound 176B was hydrogenated at 40 psi in the presence of Pd/C catalyst overnight to remove the benzyl group to provide compound 177A.

Step B

EXAMPLE 177

10 mg (0.018 mmol) of compound 177A was dissolved in 10 mL of acetone with 4 mg (0.028 mmol) potassium carbonate and 6 mg (0.036 mmol) of 1-bromo-3,3-dimethyl butane. The mixture was stirred at reflux (65° C.) overnight and concentrated. KOH in MeOH and water were added to the reaction which was then stirred for several hours. Purification by prep HPLC yielded Example 177. MS, m/z (M+1)$^+$=504.

EXAMPLE 178

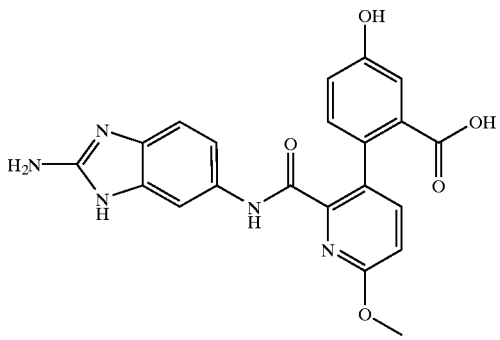

Compound 177A was treated with KOH in MeOH and water to give Example 178 above. MS, m/z (M+1)$^+$=420.

EXAMPLE 179

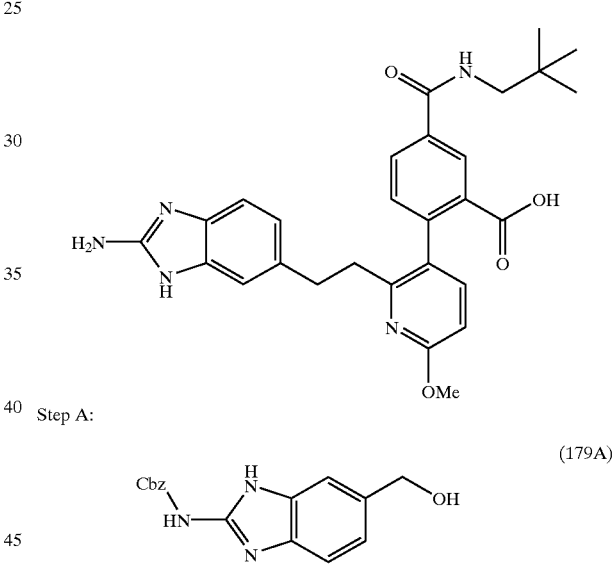

Step A:

(179A)

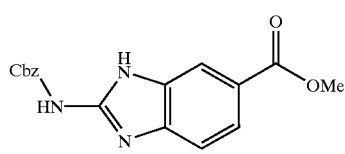

To a suspension of ester (2.0 g, 6.15 mmol) in DCM (50 ml) at −78° C. was added a solution of DIBAL in DCM (1.0M, 35 ml). The mixture was stirred at −78° C. for 1 h, warmed to rt and quenched with the addition of MeOH (5 ml) and 1 N HCl (5 ml). The mixture was diluted with EtOAc, washed with brine, dried (MgSO$_4$) and concentrated to give compound 179A (1.50 g) as a yellow solid. LC-MS: (M+H)$^+$=298.

Step B:

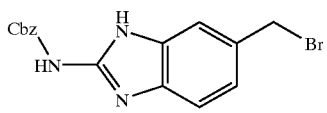
(179B)

To a suspension of alcohol 179A (900 mg, 3.0 mmol) in DCM (25 mL) was added Br$_2$PPh$_3$ and the resulting mixture was stirred at RT for 4.5 h. The solvent was removed to give the bromide 179B as a semi-solid.

Step C:

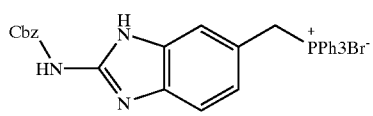
(179C)

To a solution of crude 179B in toluene (20 ml) was added triphenylphosphine (945 mg, 3.6 mmol). The mixture was heated at 60° C. for 1 h. Ethyl ether (20 ml) was added, and the solid was collected by filtration, washed with ethyl ether, EtOAc, THF, 10% DCM/ethyl ether and acetonitrile to give compound 179C (915 mg) as a light gray solid.

Step D:

(179D)

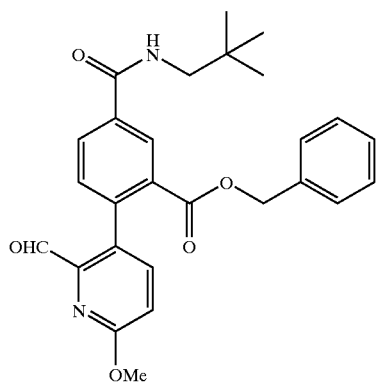

A mixture of triflate

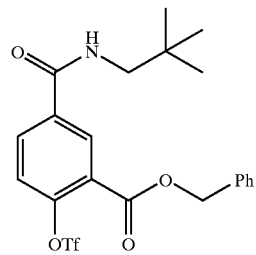

(1.0 g, 2.11 mmol) (compound 201A),

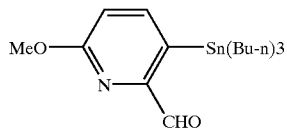

(1.46 g, 3.42 mmol), CuO (168 mg, 2.11 mmol) and PdCl$_2$(PPh$_3$)$_2$ (130 mg) in DMF (10 ml) was degased and heated at 105° C. for 1 h. HPLC showed completion of the reaction. The reaction was diluted with EtOAc (100 ml), washed with 1 N HCl, saturated NaHCO$_3$ solution, brine, dried (MgSO$_4$) and concentrated to give the crude product. Purification of the crude product by flash column chromatography (silica, 10–30% EtOAc/hexane) gave 179D (915 mg) as a yellow solid.

Step E:

(179E)

To a suspension of 179C (203 mg, 0.33 mmol) in THF (6.0 ml) at –78° C. was added NaHMDS (1.0 M in THF, 730 μl). The mixture was stirred at –78° C. for 30 min and then stirred at –30° C. for 10 min. A solution of 179D (140 mg, 0.3 mmol) in THF (2 ml) was added, and the mixture was slowly warmed to rt during 1 h and stirred at rt for 30 min. The mixture was then diluted with EtOAc, washed with water, brine, dried (MgSO$_4$) and concentrated to give the crude product as a yellow foam (220 mg). The crude product contained both trans and cis isomers. After storing at room temperature for 5 days, the crude product (120 mg) was recrystallized from MeOH to give 179E (18 mg) as a yellow solid.

Step F

EXAMPLE 179

A mixture of 179E (12 mg, 0.016 mmol), Pd/C (10%, 2 mg) and 1 N HCl solution (20 μl) in dioxane (1.5 mL) was stirred under hydrogen atmosphere (hydrogen balloon) at rt for 5 h. HPLC indicated completion of the reaction. The reaction mixture was filtered through a celite cake, evaporated and lyophalized to give Example 179 (5.6 mg) as a white fluffy powder. HPLC: 91% purity; MS: (M+H)$^+$=527.

EXAMPLE 180

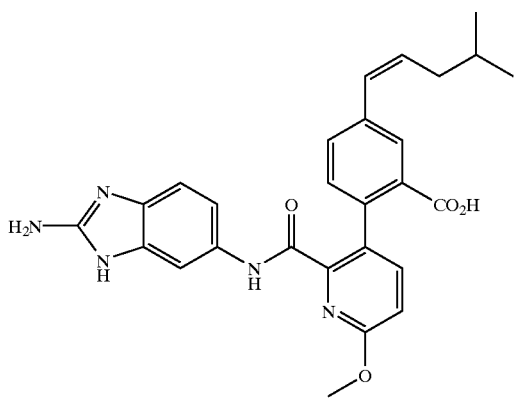

The above compound was prepared using the procedure to prepare Example 171, except 2,6-Diamino-benzoimidazole-1-carboxylic acid tert-butyl ester was used in Step F. MS, m/z, (M+1)⁺=486. ¹H-1HNMR(400 MHz), δ7.96 (d, 1H, ArH), 7.87 (d, 1H, ArH), 7.58 (d, 1H, ArH), 7.38 (dd, 1H, ArH), 7.27 (2s, 2H, ArH's), 7.21(d, 1H, ArH), 7.03 (d, 1H, ArH). 6.52 (d, 1H, CH=), 5.81 (dt, 1H, =CH), 4.11 (s, 3H, OCH₃), 2.27 (m, =CCH₂), 2.75 (m, 1H, =CCCH), 0.95 (d, 6H, 2(CH₃)₂).

EXAMPLE 181

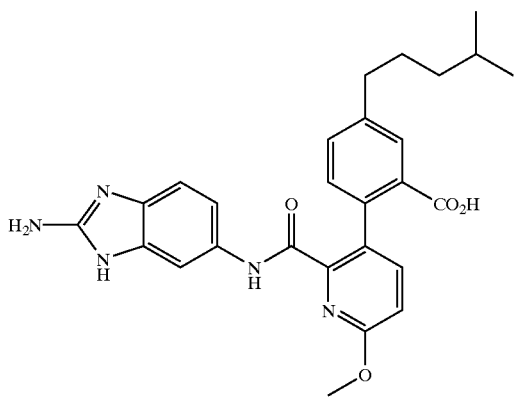

A mixture of 5 mg of Example 180 and 10 mg of Pd/C in 20 mL of MeOH was hydrogenated at 40 psi for 3 h and filtered. The filtrate was concentrated and the residue purified with HPLC using YMC S5 ODS 20×100 column to give 2 mg of Example 181. MS, m/z (M+1)⁺=486. ¹H-1HNMR (400 MHz), δ7.65 (s, 1H, ArH),7.54 (s, 1H, ArH), 7.46 (d, 1H, ArH), 7.14 (d, 1H, ArH), 7.07 (2s, 2H, ArH's), 6.97 (d, 1H, ArH), 6.84 (d, 1H, ArH), 3.94 (s, 3H, OCH₃), 2.52 (t, 2H, ArCH₂), 1.50 (m, 2H, ArCCH₂), 1.49 (m, 1H, ArCCCCH), 1.05 (m, 2H, ArCCCH₂), 0.71 (d, 6H, 2(CH₃)₂).

EXAMPLE 182

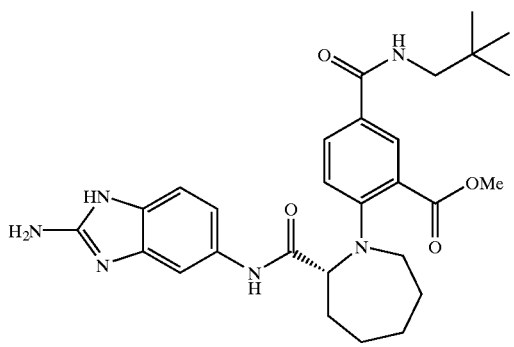

Step A:

(182A)

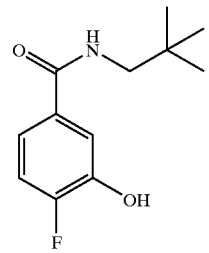

To a solution of 3-hydroxy-4-fluorobenzoic acid (2.1 g, 13.45 mmol) in DCM (50 mL) was added 2,2-dimethylpropylamine (1.76 g, 20.2 mmol), DIC (2.53 mL, 16 mmol), and HOAT (2.2 g, 16 mmol). The mixture was stirred at rt overnight. The reaction mixture was diluted with ethyl ether (50 mL) and filtered. The filtrate was washed with 1N HCl solution, sat'd NaHCO₃ and water, then dried (MgSO₄) and concentrated to give the crude product which was purified by flash chromatography (30–50% EtOAc/hexane) to give compound 182A (3.0 g, 99% yield).

Step B:

(182B)

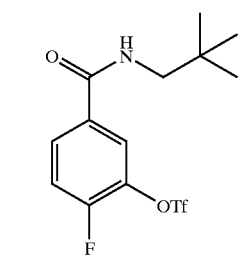

To a solution of compound 182A (3.0 g, 13.3 mmol) in DCM (30 mL) was added pyridine (5.4 mL, 67 mmol) and triflic anhydride (4.48 mL, 26.6 mmol) at 0° C. The mixture was stirred at rt for 1 h. The reaction was quenched with the addition of water (50 mL) at 0° C. and extracted with EtOAc. The extracts were combined and washed with 1N HCl solution, sat'd NaHCO₃ and brine, then dried (MgSO₄) and concentrated to give the crude product which was purified by flash chromatography (20–30% EtOAc/hexane) to give compound 182B (4.42 g, 93% yield) as a light yellow oil.

Step C:

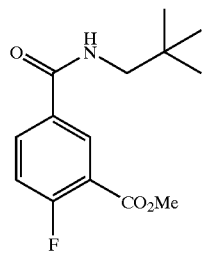
(182C)

A mixture of compound 182B (4.1 g, 11.5 mmol), MeOH (10 mL), TEA (3.2 mL), DPPF (380 mg) and Pd(OAc)$_2$ in DMF was heated at 60° C. for 4 h with the bubbling of carbon monoxide. The reaction was cooled to rt, quenched with water (50 mL) and extracted with ethyl ether (5×50 mL). The extracts were combined and washed with 1N HCl solution, sat'd NaHCO$_3$ and brine, then dried (MgSO$_4$) and concentrated to give the crude product. Purification by flash chromatography (20–30% EtOAc/hexane) gave compound 182C (2.1 g, 68% yield) as a white solid.

Step D:

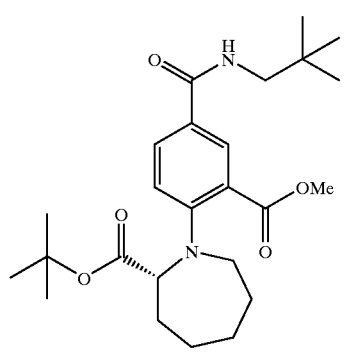
(182D)

A mixture of compound 182C (120 mg, 0.45 mmol),

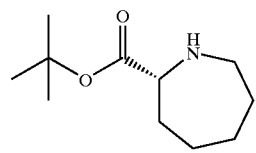

(130 mg, 0.68 mmol) and DIPEA (1.0 mL) in DMSO (2.0 mL) was heated at 120° C. for 3 days. The reaction was then cooled to rt and diluted with EtOAc, washed with water (50 mL) and brine, dried (MgSO$_4$) and concentrated to give the crude product. The crude product was purified by RP preparative HPLC. The purified product was collected, concentrated, neutralized with sat'd bicarbonate solution, and extracted with EtOAc. The extracts were combined and concentrated to give compound 182D (72 mg, 36% yield).

Step E:

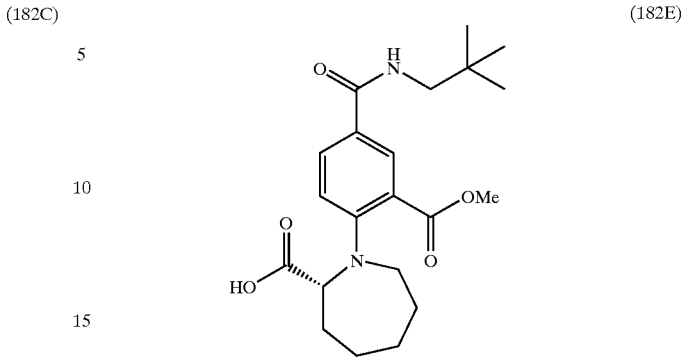
(182E)

To a solution of compound 182D (70 mg, 0.16 mmol) in CH$_2$Cl$_2$ (1.6 mL) was added TFA (0.8 mL). The mixture was stirred at rt for 5 h. The solvent and excess TFA were removed under vacuum to give the crude product. The crude product was dissolved in MeOH and passed through a PVP resin column to give compound 182E (60 mg).

Step F:

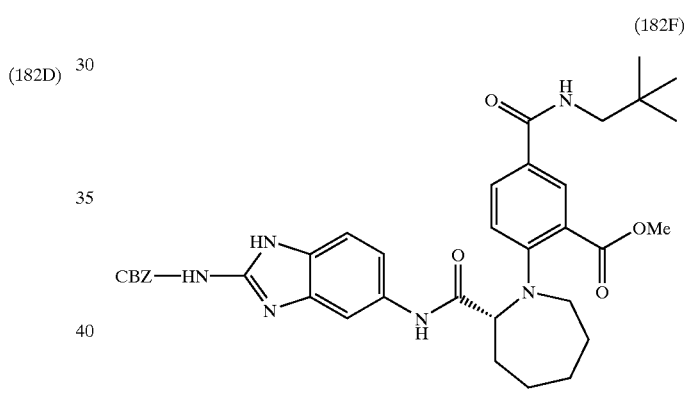
(182F)

A mixture of compound 182E (30 mg, 0.077 mmol), 2-(CBZ-amino)-5-aminobenzimidazole (24 mg, 0.085 mmol), DCC (18 mg, 0.085 mmol), HOAT (5 mg) and DMAP (several crystals) in DMF (2 mL) was stirred at rt overnight. The reaction mixture was filtered and concentrated. The residue was purified by flash chromatography (10–20% MeOH/CH$_2$Cl$_2$) to give compound 182F (45 mg).

Step G

EXAMPLE 182

A mixture of compound 182F (42 mg, 0.064 mmol), 1N HCl (64 µL, 0.064 mmol), Pd/C (10%, 10 mg) in MeOH (2 mL) was stirred under hydrogen atmosphere (hydrogen balloon) at rt for 2 h. LC-MS indicated the completion of the reaction. The reaction mixture was filtered through a 4µ microfilter and concentrated to give Example 182 (35 mg) as a yellow solid.

EXAMPLE 183

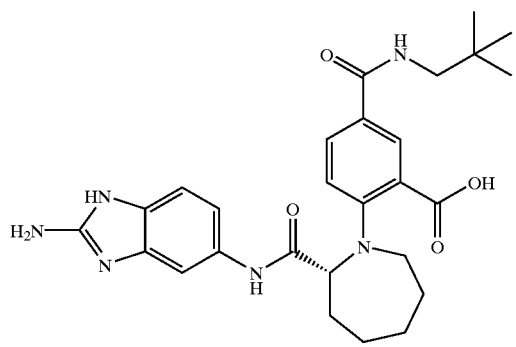

50% NaOH solution (0.5 mL) was added to a solution of Example 182 (35 mg) in MeOH/THF/H$_2$O (3:1:1, 2 mL). The mixture was stirred at rt for 2.5 h. LC-MS indicated the reaction was complete and then the reaction mixture was neutralized to pH=5 using 6 N HCl and concentrated to give the crude product. Purification of the crude product by RP preparative HPLC yielded Example 183 (24 mg, TFA salt) as a white powder. MS: (M+H)$^+$=507.

EXAMPLES 184–190

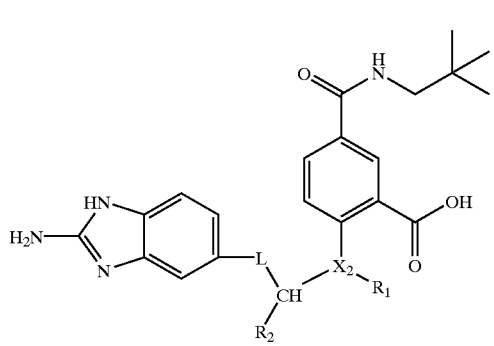

(Im)

The compounds of Examples 184–190, having the formula (Im) above wherein the groups —L—(CHR$_2$)—X$_2$(R$_1$)— together have the values shown in Table 10, were prepared following the same or similar procedure as in Examples 182 and 183, using an appropriate amine in Step D.

TABLE 10

| Ex. | —L—CH(R$_2$)—X$_2$(R$_1$)— | MS (M+H)+ |
|---|---|---|
| 184 | | 507 |
| 185 | | 479 |
| 186 | | 515 |
| 187 | | 529 |
| 188 | | 493 |
| 189 | | 493 |
| 190 | | 543 |

EXAMPLE 191

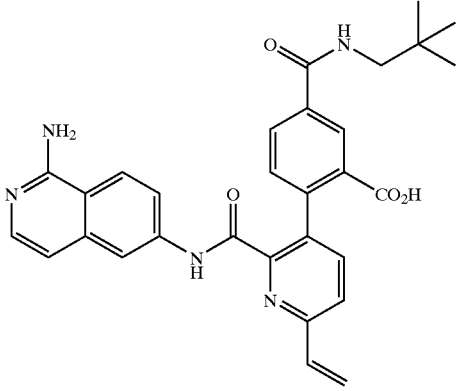

Step A:

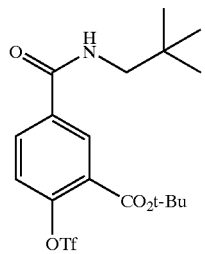
(191A)

Compound 70C from Example 70 (6.00 g, 16.2 mmol) was treated with neopentylamine (1.9 mL, 16.2 mmol) following the procedure described for the preparation of compound 3A in the synthesis of Example 3. Chromatography on silica gel (hexane-EtOAc, 75:25) provided 6.04 g of compound 191A as a white solid.

Step B:

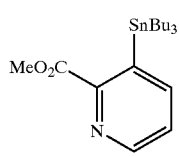
(191B)

Aldehyde

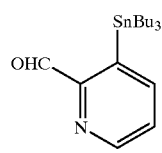

(6.36 g, 16.0 mmol) (see Ex. 207, step A) was converted to the carboxylic acid upon treatment with sodium chlorite as described for the preparation of compound 70C in Example 70 to afford 7.71 g of the acid as an oil. The acid (7.70 g, 16 mmol) was mixed with 30 mL of DMF, cesium carbonate (2.61 g, 8 mmol), and methyl iodide (1.2 mL, 19.2 mmol). The mixture was stirred for 17 h and then diluted with EtOAc and water. The EtOAc was washed with water (2×), dilute sodium thiosulfate (2×), and water (2×), dried (sodium sulfate), and concentrated to an oil. Chromatography of the oil over silica gel using hexane-EtOAc (first 80:20, then 75:25) afforded 4.90 g of the methyl ester (compound 191B) as an oil.

Step C:

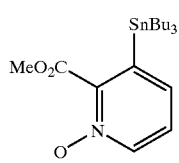
(191C)

A mixture of compound 191B (4.90 g, 11.5 mmol) and 2.90 g of 77% pure 3-chloroperoxybenzoic acid in 70 mL of DCM was stirred for 19 h and then concentrated to a residue, which was taken up in EtOAc. The EtOAc was washed with dilute NaHCO₃ (2×) and water (4×), dried (sodium sulfate), and concentrated to give 5.09 g of crude compound 191C as an oil.

Step D:

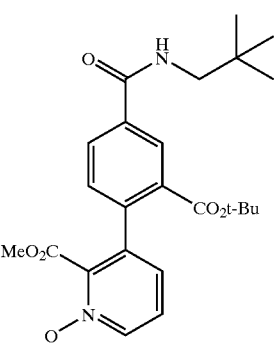
(191D)

Treatment of compound 191A (3.45 g, 7.85 mmol) and 191C (4.03 g, 9.11 mmol) with dichlorobis(triphenylphosphine)palladium(II) and powdered copper (II) oxide in DMF as described for the preparation of compound 70E in the synthesis of Example 70 gave 6.93 g of crude compound 191 D, which was chromatographed over silica gel using 1–4% MeOH in DCM to give 2.42 g of compound 191D as a white amorphous solid.

Step E:

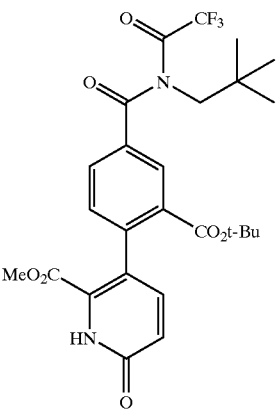
(191E)

Trifluoroacetic anhydride (1.4 mL, 10 mmol) was added to compound 191D (443 mg, 1 mmol) in 3 mL of DMF and the solution was stirred for 19 h at rt. The solvent was removed in vacuo and the residue taken up in EtOAc. The EtOAc was washed with water (2×), cautiously with dilute NaHCO₃ (2×), and water (2×), dried (sodium sulfate), and concentrated to give 525 mg of crude compound 191E as a yellow oil.

Step F:

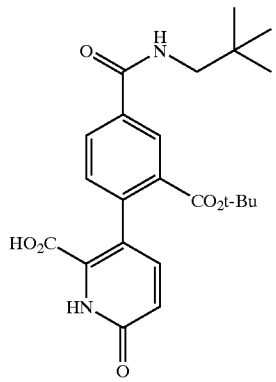
(191F)

A mixture of crude compound 191E above (523 mg) in THF (3 mL), water (2 mL), and 4.5 mL of 1 N NaOH was stirred at rt for 7 hours, acidified with 1 N HCl, and concentrated to a wet residue, which was taken up in EtOAc and water. After three extractions with EtOAc, the aq. layer and suspended solids were extracted with a small amount of chloroform (2x). The combined organic extracts were washed with water (3x), dried (sodium sulfate), and concentrated to give 351 mg of compound 191F as an amorphous white solid.

Step G:

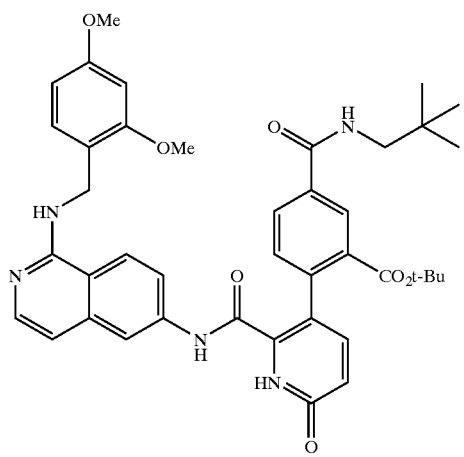
(191G)

Compound 191F (257 mg, 0.60 mmol) was treated with amine-coupling component from Scheme X (212 mg, 0.58 mmol) in DMF as described for compound 194D in Example 194 to provide 217 mg of compound 191G as an amorphous residue after chromatography on silica gel using 2–5% MeOH in DCM.

Step H:

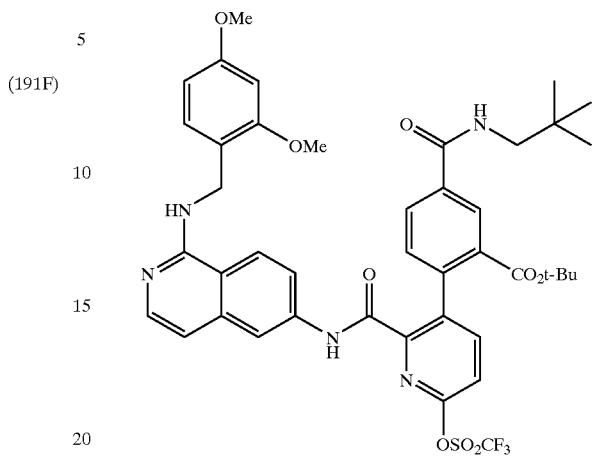
(191H)

A mixture of compound 191G (21.5 mg, 0.03 mmol), N-phenyltrifluoromethylsulfonimide

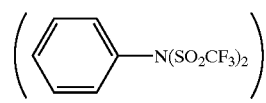

(10.7 mg, 0.03 mmol), 0.6 mL DCM, and TEA (5 µL, 0.036 mmol) was stirred overnight at rt. Additional DCM (0.5 mL) was added along with TEA (5 µL, 0.036 mmol), and the reaction was stirred for 20 h longer and diluted with DCM. The DCM was washed with water (2x), dried (sodium sulfate), and concentrated to a residue, which was chromatographed over silica gel using 1–2% MeOH in DCM to give 14 mg of compound 191H as a glassy residue.

Step I:

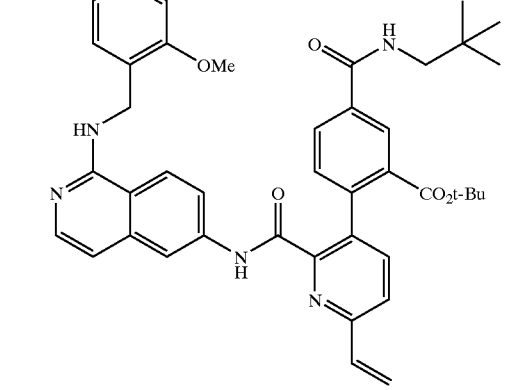
(191I)

A mixture of compound 191H (14 mg, 0.016 mmol), tributyl(vinyl)tin (6 µL, 0.02 mmol), copper (II) oxide (1.3 mg, 0.02 mmol), 0.5 mL of degassed DMF, and 0.8 mg of dichlorobis(triphenylphosphine)palladium (II) was stirred at 110° C. for one hour, cooled, and filtered using EtOAc. The filtrate was washed with water (4x), dried (sodium sulfate), and concentrated to a residue, which was chromatographed over silica gel using 1–2% MeOH in DCM to give 9 mg of compound 191I as a glassy residue.

Step J

EXAMPLE 191

TFA (0.3 mL) was added to a mixture of compound 191I (9 mg, 0.012 mmol) in anisole (7 μL, 0.06 mmol). The reaction was stirred for 3 h, diluted with several drops of water, and concentrated to a residue, which was applied in MeOH to a column of SCX resin. After washing with MeOH, the column was eluted with 2 M ammonia in MeOH. Concentration of the eluate gave a solid which was dissolved in DCM and several drops of TFA. Concentration of the mixture gave a residue, which was triturated with ether to give 6 mg of Example 191 in the TFA salt form as a solid. MS (M+H)$^+$=524.

EXAMPLE 192

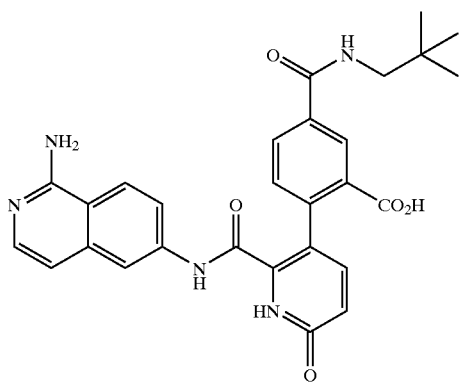

Treatment of compound 191G from Example 191 (10.2 mg, 0.014 mmol) with TFA and anisole as described in the last step of Example 191 afforded 6 mg of Example 192 in the TFA salt form as a solid. MS (M+S)$^+$=514. A tautomeric form of Example 192 wherein the lower keto group (=O) is replaced with hydroxy (—OH) may exist in the presence of some solvents or under different physiological conditions.

EXAMPLE 193

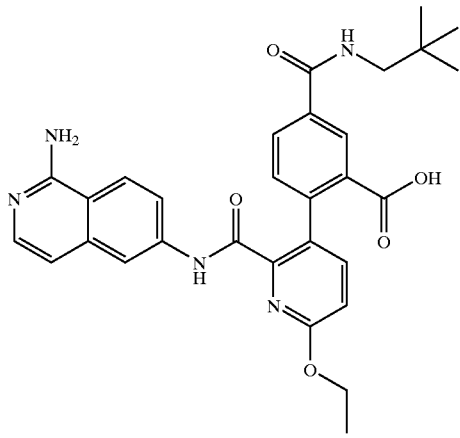

Step A:

(193A)

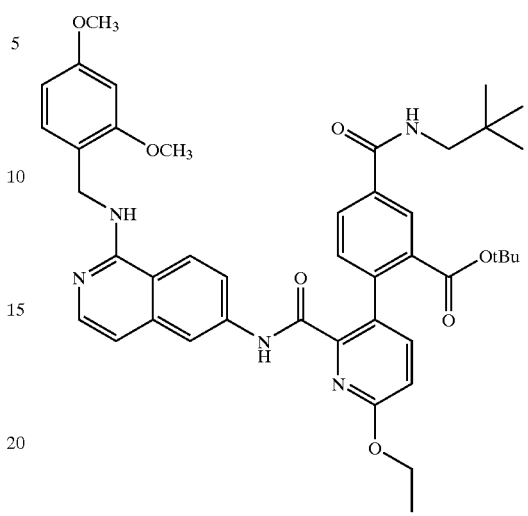

PPh$_3$ (22.0 mg, 0.084 mmol) was added to a solution of compound 191G from Example 191 (20.0 mg, 0.028 mmol) in THF (110 μL). EtOH (10.0 μL, 0.168 mmol) was added followed by DIAD (17.0 μL, 0.084 mmol). After 3 h, the reaction mixture was placed on top of a SCX cation exchange column (CUBCXHL3R3, 300 MG) which had been conditioned with MeOH (1.5 mL). The column was washed with MeOH (3×1.5 mL) and then eluted with 2.0M NH$_3$/MeOH (1.5 mL). The filtrate was conc. to give 21 mg (100%) of Example 193A.

Step B

EXAMPLE 193

TFA (150 μL) was added dropwise to a stirred solution of compound 193A (21.0 mg, 0.028 mmol) in DCM (200 μL) and anisole (25 μL). After 3 h, the reaction mixture was placed on top of a SCX cation exchange column (CUBCXHL3R3, 300 MG) which had been conditioned with MeOH (1.5 mL). The column was washed with MeOH (2×1.5 mL) and then eluted with 2.0M NH$_3$/MeOH (1.5 mL). The filtrate was conc. and placed under vacuum. The residue was dissolved in DCM:TFA (3:1). The solution was conc. and the residue dissolved in MeOH. The solution was conc. and placed under vacuum to give 13.7 mg (74%) of Example 193 as the TFA salt. MS (M+H)$^+$=542.

EXAMPLE 194

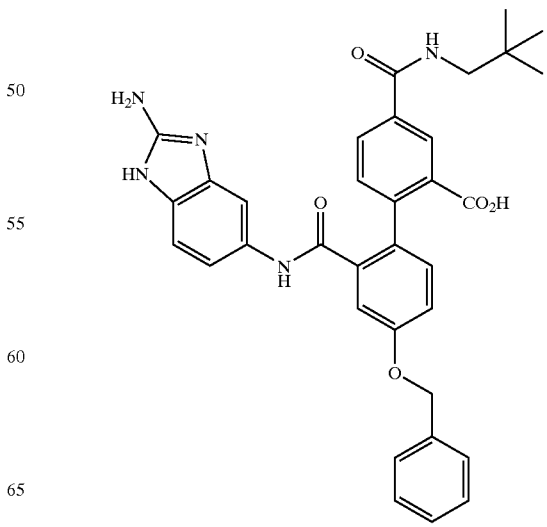

Step A:

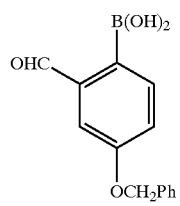
(194A)

Compound 194A was prepared from

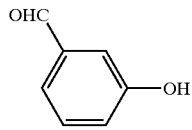

(3-hydroxybenzaldehyde) as described: G. M. Keseru, et al., Tetrahedron, Vol. 48 (1992), at pp. 913–922.

Step B:

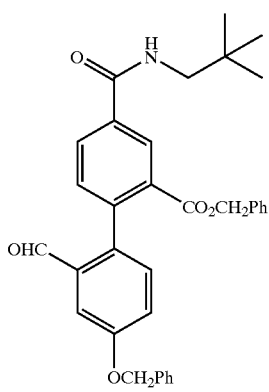
(194B)

Compound 194A (154 mg, 0.60 mmol), compound

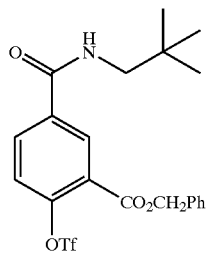

284 mg, 0.60 mmol) (see WO 99/41231), potassium phosphate (191 mg, 0.90 mmol), and tetrakis(triphenylphosphine)palladium (21 mg, 0.018 mmol) in 2.5 mL of degassed DMF were heated at 100° C. for 40 min., cooled, diluted with ice-cold water, and extracted with EtOAc. The EtOAc was washed with brine (2×), dried (MgSO$_4$), and concentrated to an oil, which was chromatographed over silica using 3–5% EtOAc in DCM to give 208 mg of compound 194B as an amorphous solid.

Step C:

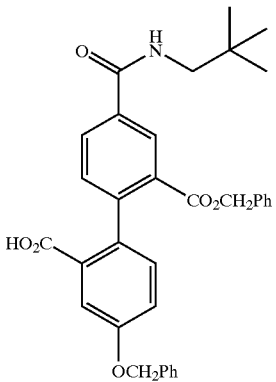
(194C)

Treatment of compound 194B (202 mg, 0.377 mmol) with sodium chlorite as described for the preparation of compound 70C in Example 70 afforded 216 mg of crude compound 194C as a white solid.

Step D:

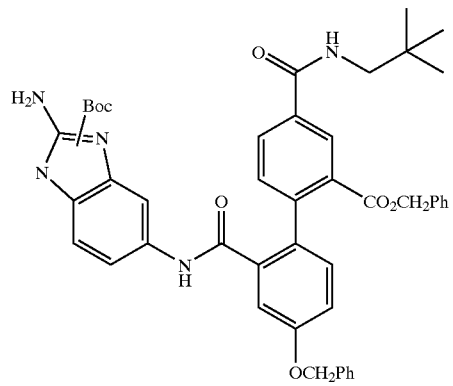
(194D)

A mixture of compound 194C (83 mg, 0.15 mmol), amine-coupling component from scheme K (39 mg, 0.15 mmol), HOAT (2 mg, 0.015 mmol), EDAC (38 mg, 0.20 mmol), and DMAP (1 mg, 0.008 mmol) in 0.8 mL of DMF was stirred for 17 h at rt and diluted with EtOAc and water. After extraction with EtOAc (2×), the EtOAc was washed with brine (3×), dried (sodium sulfate), and concentrated to an oil which was chromatographed on silica gel using 1% MeOH in DCM to provide 63 mg of compound 194D as an amorphous residue.

Step E

EXAMPLE 194

A mixture of compound 194D (23 mg, 0.029 mmol), THF (800 μL), water (60 μL), and 1 N NaOH (145 μL) was stirred at rt for 22 hours, acidified to pH 2 with 1 N HCl, and concentrated to a gum. MeOH, water, and TFA were added and the solution was concentrated to a gum, which was triturated with water to give 7.8 mg of Example 194, above, in the TFA salt form as a solid. MS $(M+H)^+$=592.

EXAMPLE 195

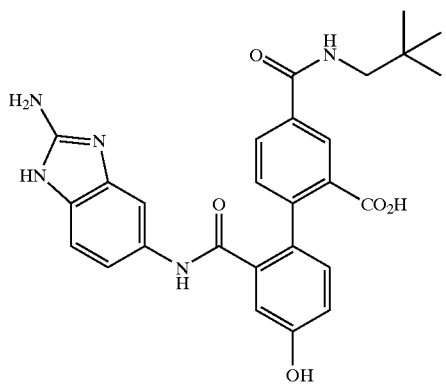

Compound 194D from Example 194 (37 mg, 0.047 mmol) was hydrogenated in 1.4 mL of MeOH and 0.4 mL of dioxane in the presence of 12 mg of 10% Pd/C for 21 h at one atmosphere. The catalyst-containing precipitated product was collected by filtration and stirred with 2.5 mL of MeOH and several drops of TFA and filtered. Concentration of the filtrate gave a glassy residue, which dissolved in DCM and several drops of TFA and stirred for one hour. Concentration of the solution afforded 12.4 mg of compound Example 195 in the TFA salt form as an amorphous solid. MS $(M+H)^+$=502.

EXAMPLE 196

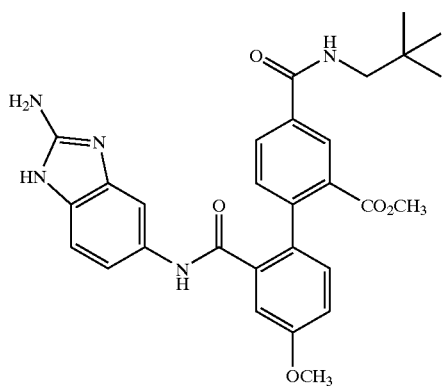

Treatment of Example 195 (10 mg, 0.016 mmol) in 1 mL of MeOH and 0.4 mL of ether with excess etheral diazomethane for 1 h provided 9.3 mg of Example 196 as a glassy residue.

EXAMPLE 197

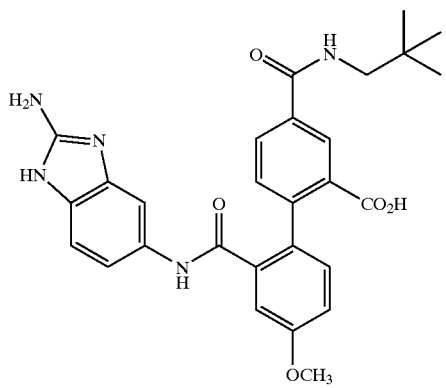

A mixture of compound 196 (9 mg, 0.014 mmol), 0.4 mL of THF, 30 µL of water, and 70 µL of 1.0 N NaOH was stirred for 4 h, acidified to pH 1.5 with 1.0 N HCl and concentrated to a gum, which was triturated with water to give 3.7 mg of Example 197 in the HCl salt form as a solid. MS $(M+H)^+$=516.

EXAMPLE 198

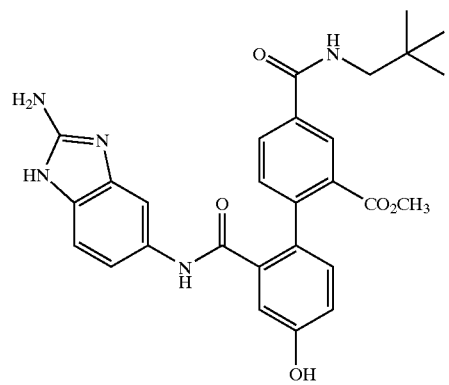

Step A:

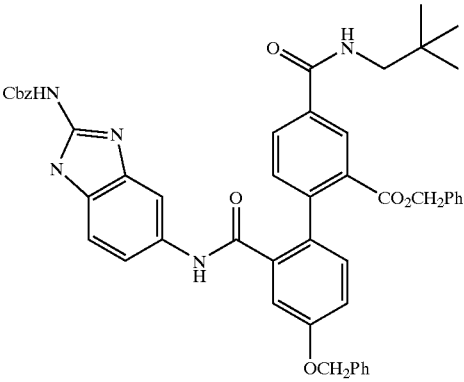
(198A)

Compound 194C from Example 194 (294 mg, 0.533 mmol) was treated with amine-coupling component X from Scheme xx (167 mg, 0.533 mmol) in DMF, using the method described for the preparation of compound 194D in Example 194 but substituting DCC for EDAC. After chromatography on silica gel using 1–2.5% MeOH in DCM, 311 mg of Compound 198A (311 mg) was obtained as a foamy residue.

Step B:

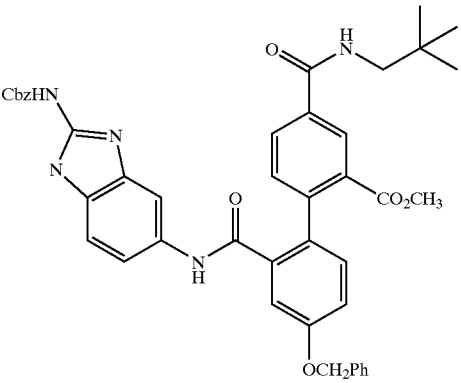
(198B)

A solution of compound 198A (49 mg, 0.06 mmol) in 0.6 mL of MeOH, 0.4 mL of THF, and 18 μL of 0.5 N sodium methoxide in MeOH was stirred for 18 h at rt. An additional 0.5 N sodium methoxide in MeOH (12 μL) was added and the reaction was refluxed for one hour. After neutralization with acetic acid, the reaction was concentrated and chromatographed over silica gel using 1–2.5% MeOH in DCM to give 26 mg of compound 198B as an amorphous residue. Step C

EXAMPLE 198

Compound 198B (24 mg, 0.0324 mmol) was hydrogenated in 1 mL of THF and 1 mL of MeOH in the presence of 8 mg of 10% Pd/C at one atmosphere for one hour to give, after concentration from THF, 21.5 mg of Example 198 as an amorphous solid.

EXAMPLE 199

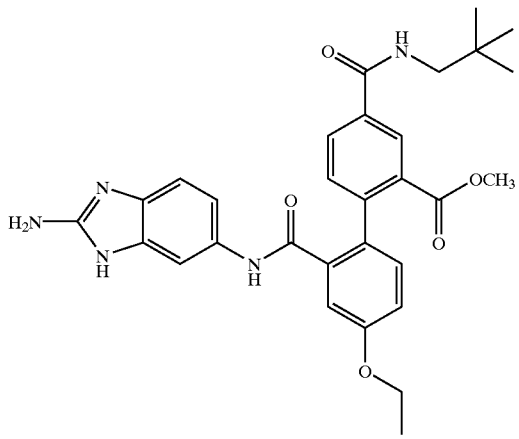

EtOH (4.0 μL, 0.065 mmol) was added to a solution of Example 198 (19.0 mg, 0.037 mmol) and PPh₃ (19.4 mg, 0.074 mmol) in DMF (300 μL). DIAD (14.6 μL, 0.074 mmol) was added. After 24 h, the reaction mixture was placed on top of a SCX cartridge (300 mg) which had been conditioned with MeOH (2×1.5 mL). The column was washed with MeOH (2×1.5 mL) and the product eluted with 2.0 $\underline{M}$ NH₃/MeOH (1.5 mL). The eluant was concentrated to give 12.7 mg (63%—crude yield) of Example 199.

EXAMPLE 200

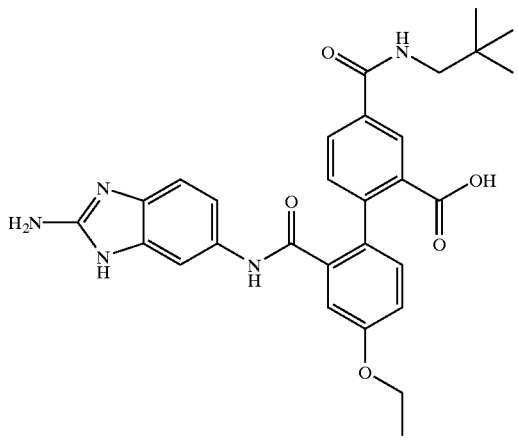

1$\underline{N}$ NaOH (0.20 mL) was added to a solution of Example 199 (22.0 mg, 0.040 mmol) in THF (0.45 mL) and H₂O (50 μL). After 12 h, the reaction mixture was directly purified by PREP HPLC using a gradient of 0 to 100% solvent B (9:1 MeOH/H₂O with 0.1%TFA) over 8 min at 20 mL/min (column: YMC S5 ODS (20×100 mm)). 2.8 mg (11%) of Example 200 was obtained in the form of the TFA salt. Ms (M+H)⁺=530.

EXAMPLE 201

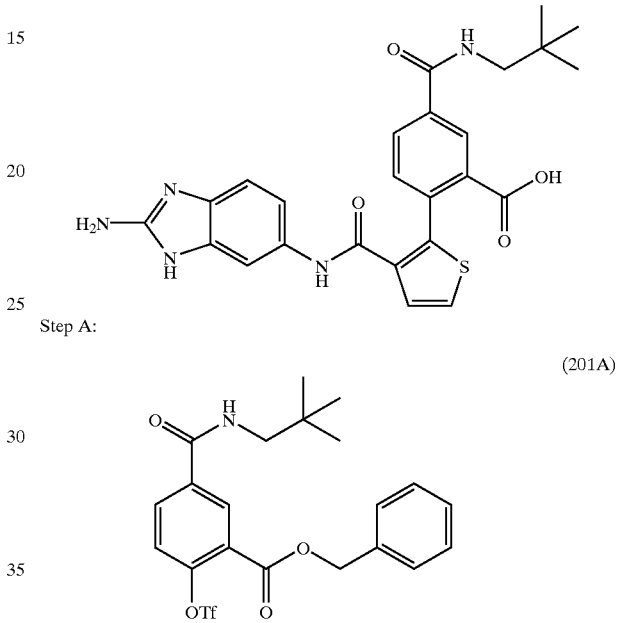

Step A:

(201A)

To a suspension of EDC (2.08 g, 10.9 mmol) in THF (100 ml) was added triflate compound

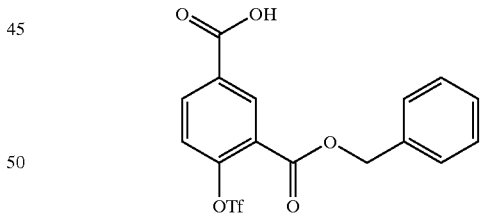

(4.01 g, 9.92 mmol) followed by HOAT (1.49 g, 10.9 mmol). CH₂Cl₂ (30 ml) was added and the reaction mixture was stirred at rt for 1 h. Neopentyl amine (3 ml) was added followed by iPr₂NEt (3 ml) and the reaction was stirred overnight. Product was extracted into EtOAc (200 ml) which was washed sequentially with 1N HCl:Brine (1:1, 200 ml×2) and sat'd NaHCO₃ (200 ml×2). The aqueous layers were back-extracted in the order generated with EtOAc (200 ml). The combined EtOAc extracts were dried over MgSO₄, filtered, and concentrated. Flash filtration through silica gel eluting with CH₂Cl₂ provided compound 201A (4.12 g). MS/(M+H)⁺=474.35.

Step B:

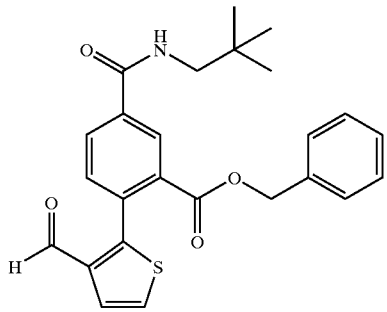
(201B)

To a solution of compound 201A (700 mg, 1.48 mmol) in nitrogen degassed dry DMF (10 ml) was added 3-formylthiophene-2-boronic acid (230 mg, 1.48 mmol), Pd(PPh$_3$)$_4$ (86 mg, 0.07 mmol), and K$_3$PO$_4$ (788 mg, 3.7 mmol). The reaction was degassed with nitrogen for 30 minutes, sealed and then heated to 95° C. for 6 h. The reaction was partitioned between EtOAc (75 ml) and water (75 ml). The organic layer was separated, dried over MgSO$_4$, filtered and concentrated to a brown residue. Purification by flash chromatography (Biotage silica cartridge 40S with a step gradient of 0–15–25% EtOAc in hexane) provided compound 201B (380 mg).

Step C:

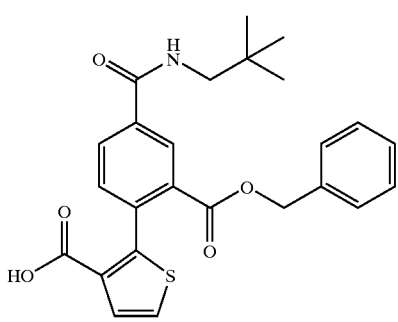
(201C)

To a solution of compound 201B (380 mg, 0.87 mmol) in tBuOH:CH$_3$CN:H$_2$O (6:1:2, 20 ml) was added 2-methyl-2-butene (2 ml), NaH$_2$PO$_4$.H$_2$O (144 mg, 1.04 mmol) and lastly NaClO$_2$ (394 mg, 4.36 mmol). The reaction was stirred at rt for 6 h. Reaction was partitioned between EtOAc and 1N HCl:brine (1:1). The organic layer was separated, dried over MgSO4, filtered and concentrated to provide compound 201C (390 mg). (M+H)$^+$=452.31.

Step D:

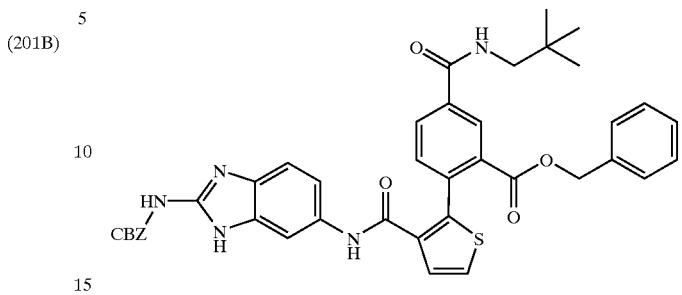
(201D)

To a solution of compound 201 D (30 mg, 0.067 mmol) in THF:CH$_2$Cl$_2$ (2:3, 2.5 ml) was added EDC (17 mg, 0.088 mmol), HOAt (12 mg, 0.088 mmol), and DMAP (11 mg, 0.088 mmol), followed by 2-(CBZ-amino)-5-aminobenzimidazole (20 mg, 0.7 mmol) and iPr$_2$NEt (200 µL). The reaction was stirred overnight at rt. The reaction was diluted with EtOAc (~10 ml) and washed with sat'd NaHCO$_3$, water and brine. The EtOAc extract was dried over MgSO$_4$, filtered and concentrated. Purification by preparative HPLC (YMC ODS S5 C18 20×100 mm, 20–100%B, 10 min grad, 2 min. hold, 20 ml/min: A=10%MeOH/Water+0.1%TFA, B=90%MeOH/Water+0.1%TFA) gave compound 201D. (M+H)+=716.39.

Step E

EXAMPLE 201

Compound 201D was taken up in THF (2.5 ml) and treated with cyclohexadiene (0.5 ml) and 10%Pd/C (40 mg). The reaction mixture was aggitated at rt for 6 hours. The reaction mixture was then filtered through a plug of celite and the plug was washed with THF. The eluent was reduced under vacuum to provide Example 201 (5.5 mg). (M+H)+=492.07.

EXAMPLES 202–206

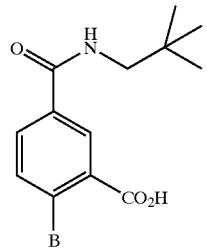
(In)

Compounds having the formula (In) wherein "B" has the values listed in Table 11 were prepared following the same procedure described in Example 201 and previous examples and schemes.

TABLE 11

| Ex. | B | MS |
|---|---|---|
| 202 | 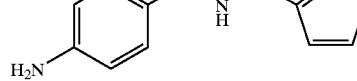 | 466.41 |
| 203 | 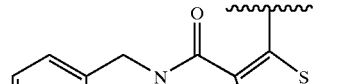 | 466.41 |
| 204 | 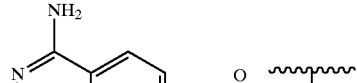 | 503.30 |
| 205 | 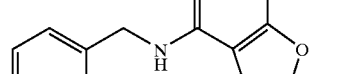 | 450.10 |
| 206 | 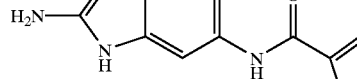 | 492.09 |

EXAMPLE 207

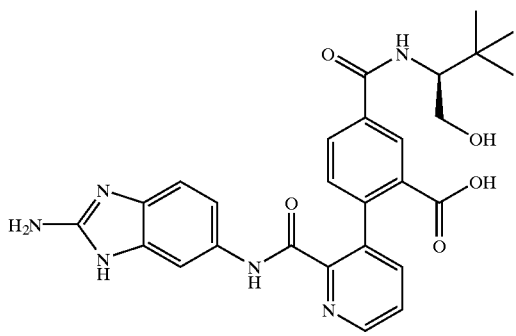

Step A:

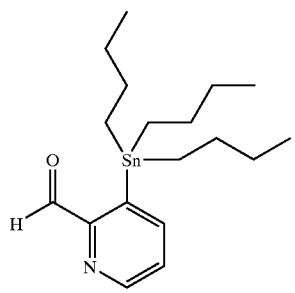

(207A)

Compound 207A was prepared using the general procedure for the stannylation of pyridine carboxaldehydes described in *J. Heterocyclic Chem*, Vol. 31, (1994), at p. 1161. To a solution of N,N,N'-trimethylethylenediamine (6.12 ml, 48 mmol) in THF (150 ml) at −78° C. was added 2.0M nBuLi (22 ml, 44 mmol). Approximately 15 min. later, 2-pyridinecarboxaldehyde (4.3 g, 40 mmol) was added and the mixture was stirred at −78° C. for 15 min. A second portion of 2.0 M nBuLi (40 ml, 80 mmol) was added and the reaction was stirred at −78° C. for 1.5 h and then −42° C. for 4 h. The reaction was cooled again to −78° C. and tributyltin chloride (27.3 g, 84 mmol) was added. The cooling bath was removed and the reaction was allowed to warm to rt. The reaction was quenched by pouring over ice cold brine (200 ml). The product was extracted from the brine with diethylether (300 ml×3). The organic phase was dried over MgSO$_4$, filtered and concentrated. Purification by flash chromatography (silica gel, 0–10% EtOAc/Hexane) gave stannane 207A (7.04 g); 1H-NMR: δ0.86 (t, 9H, j=7.3), 1.0–1.19 (m, 6H), 1.22–1.35 (m, 6H), 1.4–1.55 (m, 6H), 7.43 (dd, 1H, j=7.2, 4.7), 8.03 (d, 1H, j=6.8), 8.73 (d, 1H, j=4.6), 10.06 (s, 1H).

Step B:

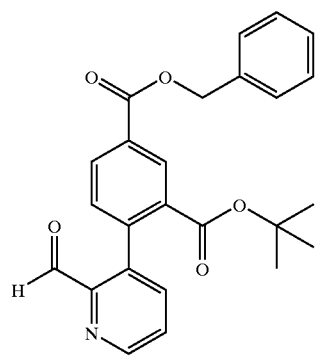

(207B)

To a solution of compound 207A (1.41 g, 3.59 mmol) and triflate compound 70D (1.5 g, 3.26 mmol) in nitrogen degassed dry DMF (12 ml) was added PdCl$_2$(PPh$_3$)$_2$ (150 mg, 0.21 mmol) and powdered CuO (190 mg). The reaction was degassed for 5 min, sealed and heated at 110° C. for 1.25 h. The reaction was diluted with diethyl ether which was then washed with sat'd NaHCO$_3$ and brine. The organic layer was dried over MgSO4, filtered, and concentrated. Purification by flash chromatography (silica gel, 0–30% EtOAc in hexanes) gave compound 207B (0.84 g); (M+H)+=418.2.

Step C:

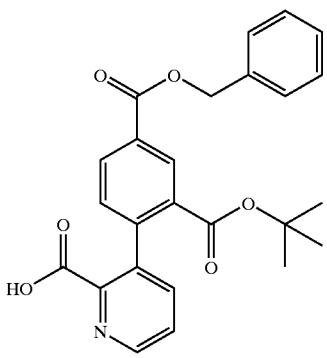
(207C)

Compound 207C was prepared from 207B (0.84 g mg, 2.01 mmol) following the same procedure as in Example 201, step C, scaling the reagents appropriately. (M+H)+= 434.44.

Step D:

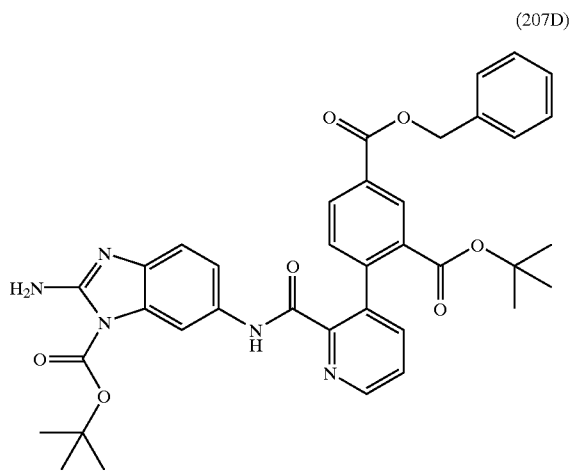
(207D)

To a solution of compound 207C (0.17 g, 0.392 mmol) in acetonitrile (10 ml) at rt was added EDC (0.112 g, 0.589 mmol), HOAT (0.081 g, 0.589 mmol) and 1-BOC-2,6-diaminobenzamidazole (0.106 g, 0.431 mmol). The reaction was stirred at rt for 18 h. The reaction was diluted with EtOAc which was then washed with 1N HCl and sat'd NaHCO$_3$. The organic layer was dried over MgSO4, filtered, and concentrated. Purification by flash chromatography (silica gel, 0–40% EtOAc in CH$_2$Cl$_2$) provided compound 207D (158 mg). (M+H)+=664.28.

Step E:

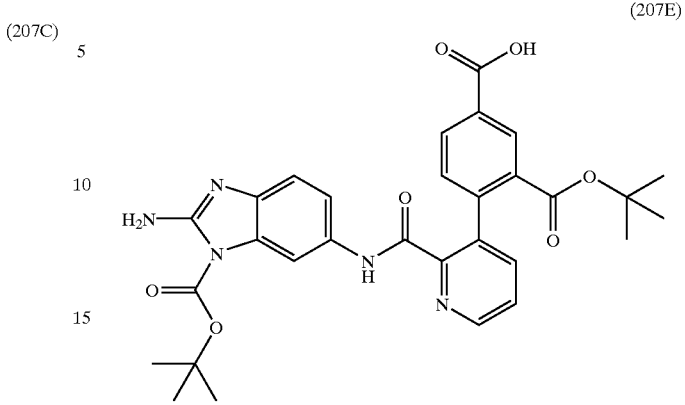
(207E)

Compound 207D (158 mg, 0.238 mmol) was disolved in THF (5 ml) and 10%Pd/C (158 mg) was added. Hydrogen was bubbled through the solution for 30 minutes and then the reaction was stirred under H$_2$ (1 atm) for 6 h. The reaction was filtered through celite and the celite pad was washed liberally with THF until no UV active compounds were detected in the eluent. Solvent was removed to give compound 207E (88 mg).

Step F:

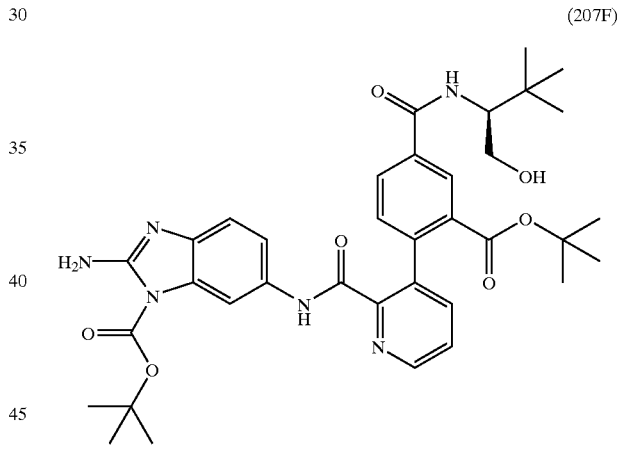
(207F)

To a solution of compound 207E (44 mg, 0.076 mmol) in DMF:acetonitrile (1:1, 1.5 ml) was added EDC (22 mg, 0.114 mmol) and HOAT (32 mg, 0.114 mmol). To this solution was added (s)-tert-leucinol (39 μl, 0.3 mmol). This reaction was stirred overnight at rt. The reaction was partitioned between EtOAc and 0.5N HCl. The organic layer was separated, washed with sat'd NaHCO$_3$, dried over MgSO$_4$, filtered, and concentrated. Purification by preparative TLC (silica gel, 5% MeOH/CH$_2$Cl$_2$) provided compound 207F (8 mg). (M+H)+=673.65.

Step G

EXAMPLE 207

Compound 207F was taken up in 20%TFA/CH$_2$Cl$_2$ and stirred at rt for 3 h. Solvent was removed and sample was taken up in MeOH (2 ml) and treated with NH$_4$OH (0.5 ml) for 1 hour. Solvent was removed and sample was taken up in water (~2 ml) as a suspension and loaded onto a C18 solid phase extraction cartridge (3 g). The cartridge was then washed with water (15 ml), the product eluted with MeOH:acetonitrile (1:1, 6 ml), and the MeOH:acetonitrile eluent reduced under vacuum to give Example 207 (3.1 mg). (M+H)+=517.49.

EXAMPLES 208–211 the compounds reported in Table 12 were prepared in a similar fashion to Example 207.

TABLE 12

| Ex. | Compound Structure | MS (M + H)+ |
| --- | --- | --- |
| 208 | 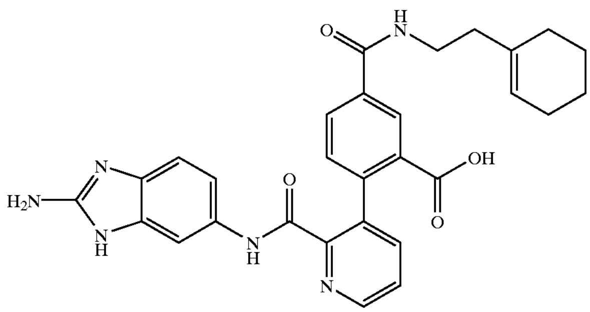 | 525.53 |
| 209 | 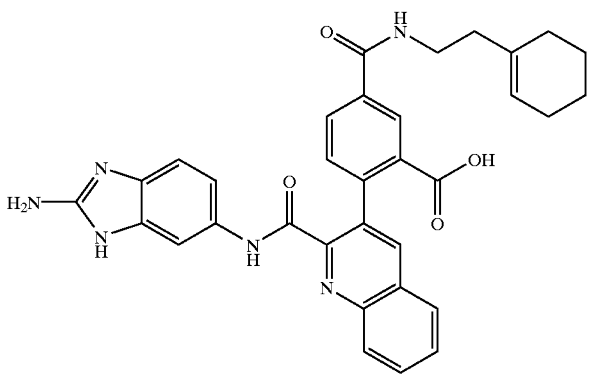 | 575.49 |
| 210 | 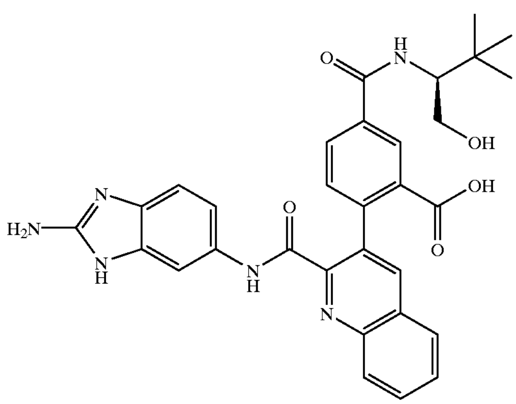 | 567.45 |
| 211 | 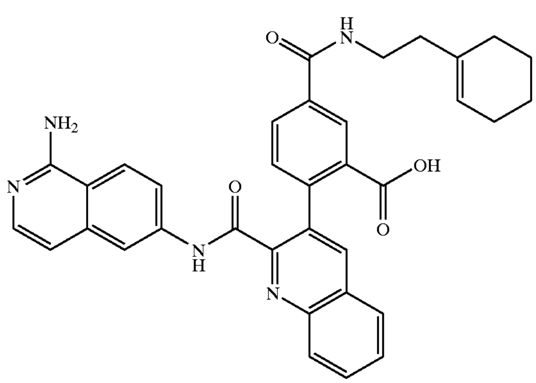 | 586.26 |

EXAMPLE 212

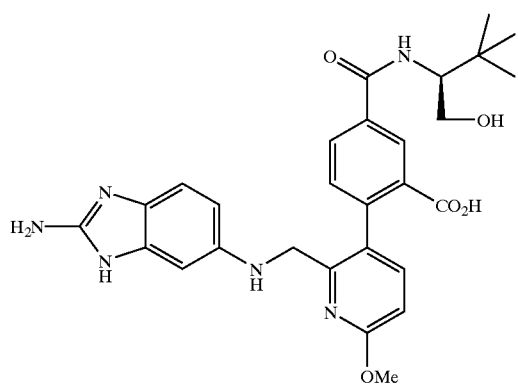

Step A:

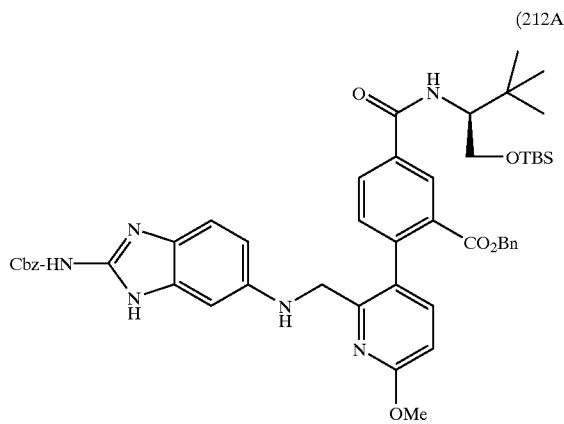
(212A)

To a mixture of

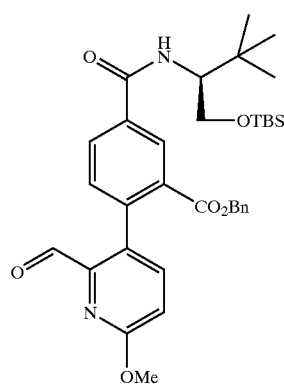

(24.6 mg, 0.087 mmol), 2-(CBZ-amino)-5-aminobenzimidazole (50 mg, 0.087 mmol) and NaBH(OAc)$_3$ (23.1 mg, 0.109 mmol) in CH$_2$Cl$_2$ (2 mL), was added AcOH (0.1 mL) at rt, and the mixture was stirred for 2 days. The reaction mixture was diluted with CH$_2$Cl$_2$ (15 mL) and washed with 10% Na$_2$CO$_3$. The organic layer was dried over MgSO$_4$ and concentrated in rotavap to give compound 212A.

Step B:

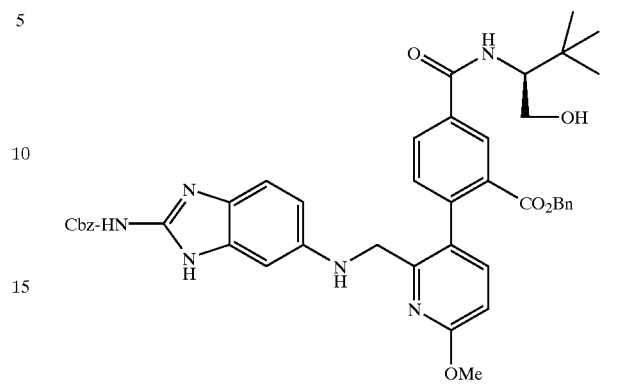
(212B)

To crude compound 212A was added 1% HCl/MeOH (5 mL). The mixture was sonicated for 2 min, allowed to sit at rt for 30 min., and concentrated to give compound 212B.
Step C

EXAMPLE 212

A mixture of compound 212B and 10% Pd/C (10 mg) in MeOH (5 mL) was stirred under hydrogen (balloon pressure) for 2 h. The reaction mixture was filtered, rinsed with MeOH, and concentrated to give crude product. Prep HPLC purification (Shimadsu S5 VP-ODS 20×100 mm) afforded Example 212 (6.5 mg, 15%) as a white lyophilate. MS: (M+H)$^+$=533.

EXAMPLES 213–228

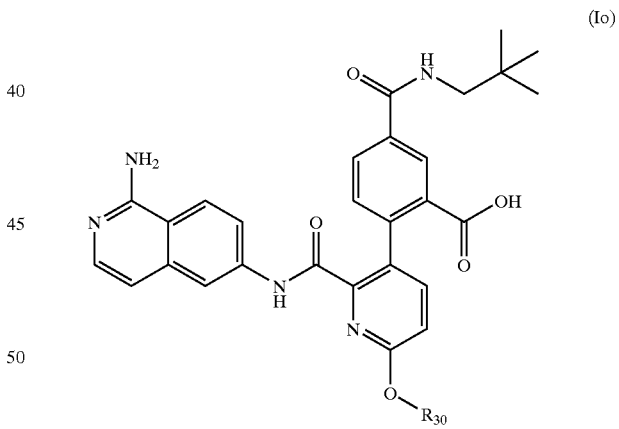
(Io)

Compounds having the formula (Io) listed in Table 13 were prepared using the procedure of Example 193 whereby various alcohols of the formula R$_1$—OH were substituted for EtOH.

TABLE 13

| Ex. | —R$_{30}$ | MS (M + H)$^+$ |
|---|---|---|
| 213 | 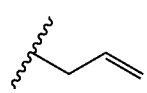 | 554 |

TABLE 13-continued

| Ex. | —R₃₀ | MS (M + H)⁺ |
|---|---|---|
| 214 | (n-butyl) | 556 |
| 215 | (isopropyl) | 554 |
| 216 | (cyclobutyl) | 568 |
| 217 | (isobutenyl) | 566 |
| 218 | (n-pentyl) | 568 |
| 219 | (isopentyl) | 568 |
| 220 | (sec-pentyl) | 568 |
| 221 | (sec-butyl) | 568 |
| 222 | (methoxyethyl) | 570 |
| 223 | (cyclobutylmethyl) | 580 |
| 224 | (hexenyl) | 580 |
| 225 | (cyclopropylethyl) | 580 |
| 226 | (n-hexyl) | 582 |
| 227 | (chlorobutyl) | 588 |
| 228 | (pentenyl) | 568 |

EXAMPLE 229

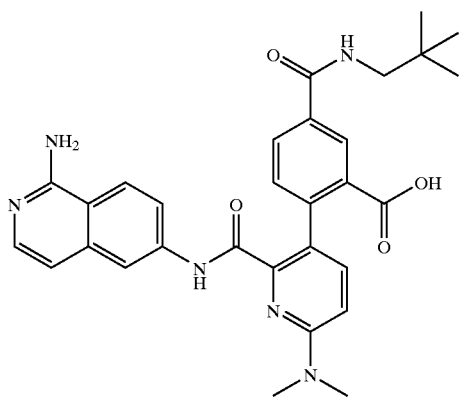

Step A:

(229A)

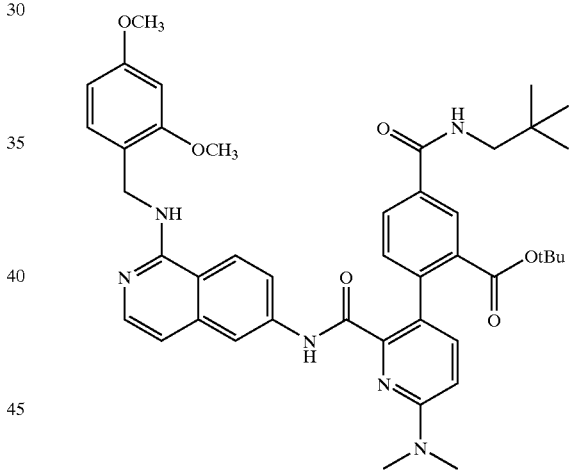

N,N-Dimethylamine (36 μL, 0.072 mmol) was added to a solution of compound 191H (15 mg, 0.018 mmol) in DMSO (225 μL). After 24 h of shaking the reaction mixture was placed on top Of a 300 mg SCX cation exchange column (CUBCX1HL3R3) which had been conditioned with MeOH (1.5 mL). The column was washed with MeOH (1.5 mL). The product was eluted with 2.0 M NH₃/MeOH (1.5 mL). The eluant was conc. to give 9.6 mg of (compound 229A).

Step B

EXAMPLE 229

TFA (100 μL) was added to a stirred solution of compound 229A (9.6 mg, 0.013 mmol) in DCM (200 μL) at rt. After 2 h of stirring, the reaction mixture was conc., dissolved in MeOH (0.5 mL) and placed on top of a 300 mg SCX cation exchange column (CUBCX1HL3R3) which had been conditioned with MeOH (1.5 mL). The column was washed with MeOH (1.5 mL). The product was eluted with 2.0 M NH₃/MeOH (1.5 mL). The eluant was conc. and placed under vacuum. The residue was dissolved in 5% TFA in MeOH. The solution was conc. and placed under vacuum. Et₂O was added to precipitate a solid. The solid was collected by filtration. 7.3 mg (54%—2 steps) of Example 229 was obtained in the TFA salt form. MS (M+H)⁺=541.

EXAMPLES 230–231

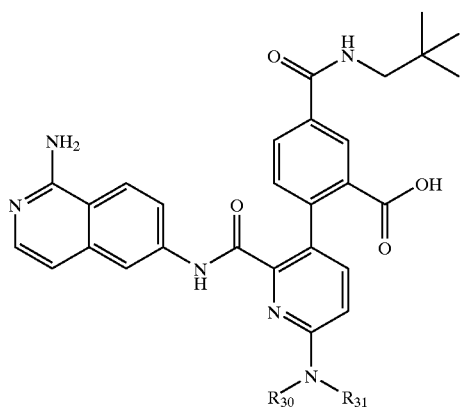
(Ip)

Compounds having the formula (Ip) above wherein the groups R₃₀ and R₃₁ are as set forth in Table 14 were prepared using the method of Example 229 with the following modification. Examples 230 and 231 were prepared by substituting N-benzylmethylamine and N-benzylethylamine, respectively, in place of N,N-dimethylamine in Step A and heating the reaction at 90° C. for 24 h. The products from Step A were treated with conc. H₂SO₄ for 4 h. The reactions were quenched with water, partially neutralized with 5N NaOH, diluted with MeOH, filtered and purified by PREP HPLC, to give the Examples in Table 14.

TABLE 14

| Ex. | R₃₁ | R₃₂ | MS (M+H)⁺ |
|---|---|---|---|
| 230 | H | —CH₃ | 527 |
| 231 | H | —CH₂CH₃ | 541 |

EXAMPLE 232

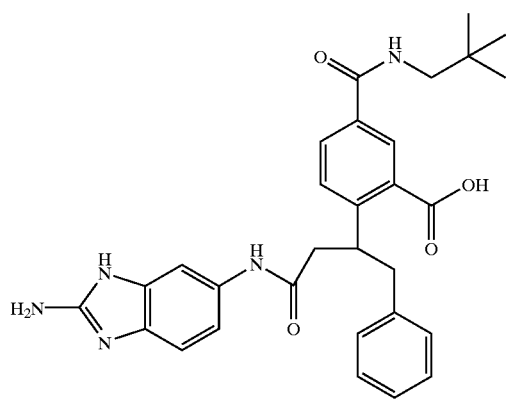

Step A:

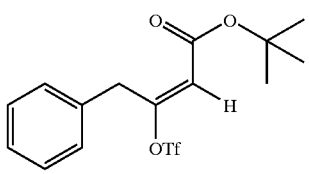
(232A)

To a suspension of NaH (258 mg, 10.2 mmol) in DMF (15 ml) was added a solution of

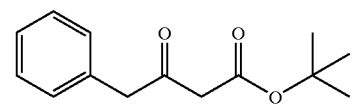

(2.0 g, 8.5 mmol) in DMF (5.0 ml) at room temperature. The resulting mixture was stirred at rt for 30 min. Tf₂NPh (3.50 g, 9.8 mmol) was added in one portion, and the mixture was stirred at rt overnight. The mixture was diluted with ether (10 ml), washed with saturated ammonium chloride solution (3×30 ml), water (2×30 ml), brine (30 ml), dried (MgSO₄) and evaporated to give the crude product. Purification of the crude product by column chromatography (silica, 5–15% CH₂Cl₂/hexane) gave compound 232A (1.30 g) as a colorless oil.

Step B:

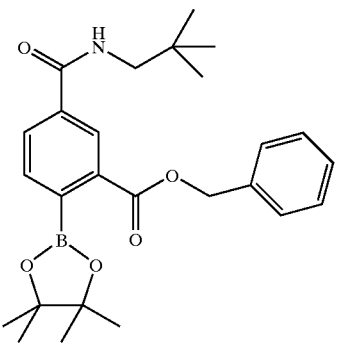
(232B)

A mixture of triflate

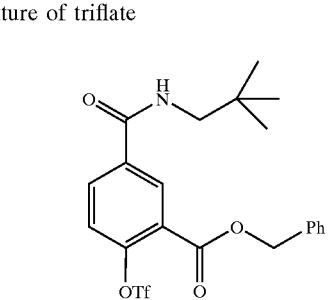

(1.34 g, 2.83 mmol), bis(pinacolate)diboron

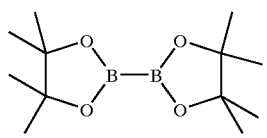

(862 mg, 3.40 mmol), potassium acetate (750 mg), PdCl₂ (dppf) and 4A molecule sieves (ground, 4.0 g) in dioxane (25 ml) was heated at 107° C. overnight. The mixture was cooled to rt and diluted with ether. The solid was removed by filtration and the filtrate was washed with water, brine, dried (MgSO₄) and concentrated to give the crude product as a dark brown oil. Purification by column chromatography (silica, 10–20% EtOAc/hexane) gave 232B (1.02 g) as a colorless oil. MS: (M+H)⁺=452.

Step C:

(232C)

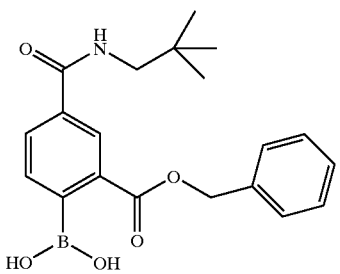

To a solution of compound 232B (530 mg, 1.17 mmol) in acetic acid (2.0 ml) was added water (3.0 ml). The mixture was stirred at rt overnight. The white precipitate was collected by filtration, washed with water and dried to give the compound 232C (295 mg) as a white solid.

Step D:

(232D)

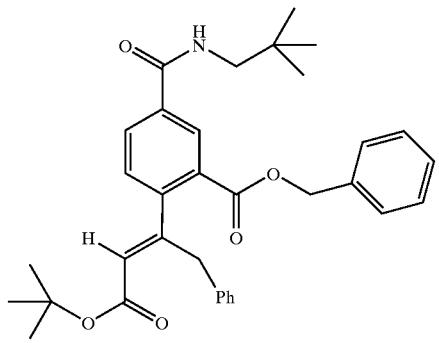

To a solution of compound 232A (37 mg, 0.10 mmol) in dioxane (3 mL) was added potassium phosphate (106 mg, 0.5 mmol), boronic acid 232C (41 mg, 0.11 mmol) and Pd(PPh₃)₄ (6 mg, 0.01 mmol). The mixture was stirred at rt overnight under argon. The mixture was diluted with DCM, filtered through a layer of celite and concentrated to give the crude product. Purification by flash column chromatography (silica, 10–30% CH₂Cl₂/hexane) gave compound 232D (40 mg) as a light yellow oil. MS: (M+H)⁺=542.

Step E:

(232E)

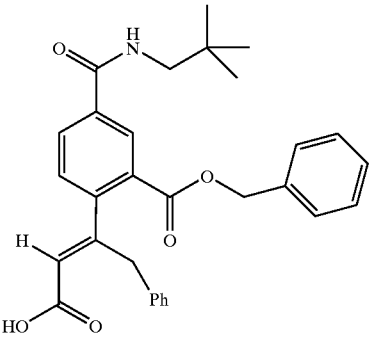

To a solution of ester 232D (40 mg, 0.74 mmol) in CH₂Cl₂ (1.6 mL) was added TFA (0.4 ml). The mixture was stirred at rt for 1 h. The solvent and excess TFA was removed under vacuum to give compound 232E (32 mg) as a yellow film.

Step F:

(232F)

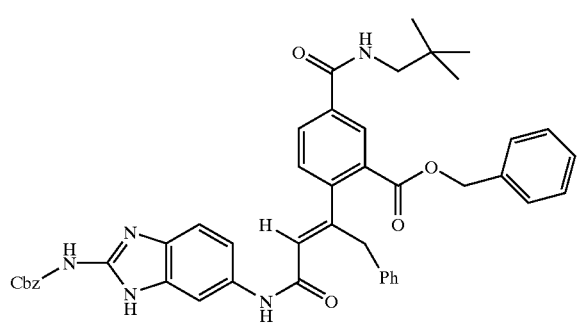

To a solution of compound 232E (30 mg, 0.062 mmol) in DMF (1.0 ml) was added the amine

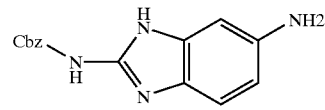

(20 mg, 0.074 mmol), DCC (15 mg, 0.074 mmol), HOAt (1 mg), and DMAP (1 mg). The mixture was stirred at rt overnight, filtered, evaporated to give the crude product. Purification by flash column chromatography (silica, 0–5% MeOH/DCM) gave 232F (26 mg) as a yellow film. MS: (M+H)⁺=750.

Step G

EXAMPLE 232

A mixture of compound 232F (16 mg, 0.021 mmol), Pd/C (10%, 10 mg) in MeOH (2 mL) was stirred under hydrogen atmosphere (hydrogen balloon) at rt for 2 days. HPLC indicated completion of the reaction. The reaction mixture was filtered through a celite cake and lyophilized to give Example 232 (5.6 mg) as a white fluffy powder. MS: (M+H)⁺=527.

We claim:

1. A compound of formula I:

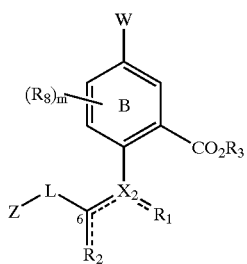

(I)

or a pharmaceutically-acceptable salt, hydrate or prodrug thereof, wherein:

W is —C(=O)NR$_4$R$_5$;

ring B is phenyl;

X$_2$ is CH, or C, provided that X$_2$ is C when R$_1$ and R$_2$ join to form a fully unsaturated ring;

L is —(CH$_2$)$_s$—Y—;

Y is selected from —C(=O), —C(=O)NR$_{13}$—, —NR$_{13}$C(=O)—, —NR$_{13}$CR$_{14}$R$_{15}$—, —CR$_{14}$R$_{15}$NR$_{13}$—, and —CR$_{13}$R$_{14}$—CR$_{15}$R$_{16}$—;

Z is a 5 to 7-membered monocyclic or 8 to 11-membered bicyclic aryl, heteroaryl, heterocyclo, or cycloalkyl, wherein each Z group is optionally substituted with up to two R$_{20}$ and/or up to one R$_{21}$, except Z is not phenyl substituted with phenyloxy when W is methoxy, s is 0 and Y is —CH$_2$—CH$_2$—;

R$_1$ and R$_2$ (ii) are taken together to form an aryl, heteroaryl, cycloalkyl, or heterocyclo, provided that when R$_1$ and R$_2$ together form a heteroaryl, aryl, heterocyclo, or cycloalkyl, said cyclic group is optionally substituted with up to three R$_{26}$;

R$_3$ is hydrogen, alkyl, or substituted alkyl;

R$_4$, R$_{4a}$, R$_5$ and R$_6$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, and cycloalkyl; or alternatively, (ii) R$_4$ and R$_5$ may be taken together to form a five-to-seven membered heteroaryl or heterocyclo, except when W is —S(O)$_p$R$_4$, then R$_4$ is not hydrogen;

R$_8$ and R$_{26}$ (i) are at each occurrence independently selected from hydrogen, OR$_{30}$, NR$_{31}$R$_{32}$, NR$_{31}$SO$_2$R$_{32a}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl, or (ii) two of R$_8$ and/or two of R$_{26}$ may be taken together to form a fused benzo ring, a fused heteroaryl, a fused cycloalkyl, or a fused heterocyclo other than a five or six membered heterocyclo having as its heteroatoms two oxygen atoms, provided further that when two R$_{26}$ form a fused benzo ring, then Z is not phenyl substituted in the para position with cyano or a five-membered heterocycle or heteroaryl;

R$_{13}$, R$_{14}$, R$_{15}$, R$_{16}$, R$_{18}$, R$_{18a}$, R$_{19}$, and R$_{19a}$ are selected from hydrogen, lower alkyl, hydroxy, and lower alkyl substituted with hydroxy or halogen;

R$_{20}$ and R$_{21}$ are independently selected at each occurrence from hydrogen, halogen, alkyl, substituted alkyl, haloalkyl, haloalkoxy, cyano, nitro, —C(=O) NR$_{22}$R$_{23}$, —OR$_{22}$, —CO$_2$R$_{22}$, —C(=O)R$_{22}$, —SR$_{22}$, —S(O)$_q$R$_{22a}$, —NR$_{22}$R$_{23}$, —NR$_{22}$SO$_2$R$_{23}$, —NR$_{22}$CO$_2$R$_{23}$, —NR$_{22}$C(=O)R$_{23}$, —NR$_{22}$C(=O) NR$_{23}$R$_{33}$, —SO$_2$NR$_{22}$R$_{23}$, —NR$_{22}$SO$_2$NR$_{23}$R$_{33}$, five or six membered heterocyclo or heteroaryl, phenyl, and four to seven membered cycloalkyl, wherein when R$_{20}$ and/or R$_{21}$ independent of each other comprise a cyclic group, each cyclic group in turn is optionally substituted with up to three of C$_{1-4}$alkyl, C$_{1-4}$alkoxy, halogen, hydroxy, haloalkyl, haloalkoxy, amino, alkylamino, and/or cyano;

R$_{22}$, R$_{23}$ and R$_{33}$ are independently selected from hydrogen, alkyl, and substituted alkyl;

R$_{22a}$ is alkyl or substituted alkyl;

R$_{30}$ at each occurrence is selected from hydrogen, alkyl, substituted alkyl, alkenyl, substituted alkenyl, cycloalkyl, and phenyl;

R$_{31}$ and R$_{32}$ at each occurrence are independently selected from hydrogen, alkyl, substituted alkyl, alkenyl, substituted alkenyl, and cycloalkyl;

R$_{32a}$ is alkyl, substituted alkyl, alkenyl, substituted alkenyl, or cycloalkyl;

m is 0, 1 or 2 when ring B is phenyl;

p and q are independently 1 or 2; and s is 0, or 1;

t is 0.

2. A compound according to claim 1, or a pharmaceutically-acceptable salt, hydrate or prodrug thereof, wherein:

ring B is phenyl;

W is —C(=O)NR$_4$R$_5$;

L is —(CH$_2$)$_s$—Y—;

Y is selected from —C(=O), —NHC(=O)—, —NH—CH$_2$— and —CH$_2$—CH$_2$—;

Z is selected from

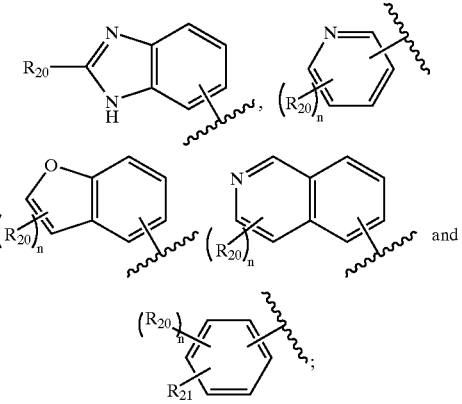

R$_3$ is hydrogen, alkyl, or substituted alkyl;

R$_4$ is hydrogen or lower alkyl;

R$_5$ is hydrogen, alkyl, substituted alkyl, alkenyl, substituted alkenyl, heterocyclo or heteroaryl;

R$_6$ is C$_{2-4}$alkyl, phenyl or benzyl;

R$_{26}$ is selected from hydrogen, OR$_{30}$, NR$_{31}$R$_{32}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, or phenyl, or (ii) two of R$_{26}$ may be taken together to form a fused benzo ring when Z is not phenyl substituted in the para position with a five-membered heterocycle or heteroaryl;

R20 and R21 are independently selected from hydrogen, halogen, alkyl, haloalkyl, haloalkoxy, nitro, —OR22, —NR22R23, five or six membered heterocyclo or heteroaryl, phenyl, and four to seven membered cycloalkyl, or alkyl substituted with amino or alkylamino, wherein when R20 and/or R21 comprise a cyclic group, each cyclic group in turn is optionally substituted with up to three of $C_{1-4}$alkyl, $C_{1-4}$alkoxy, halogen, hydroxy, haloalkyl, haloalkoxy, amino, alkylamino, and/or cyano;

n is 0, 1 or 2; and s is 0 or 1.

3. A compound according to claim 1, or a pharmaceutically-acceptable salt, hydrate or prodrug thereof, wherein Z is selected from:

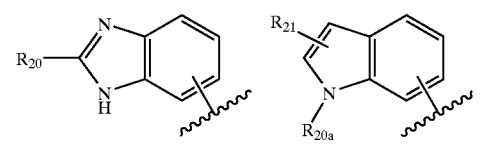

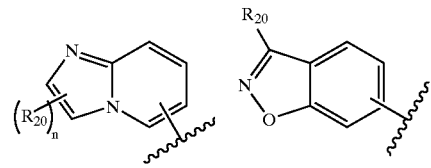

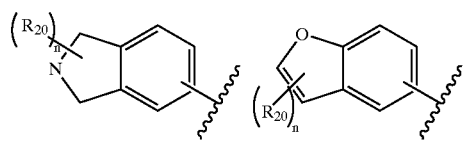

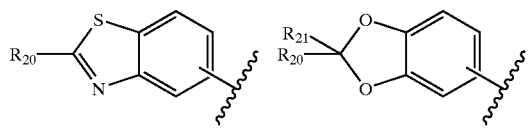

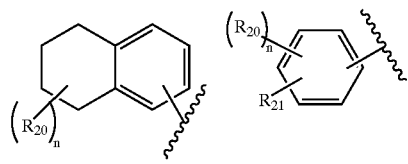

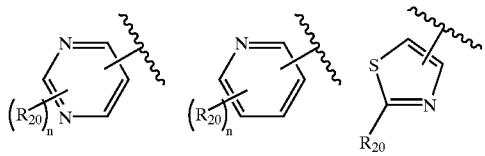

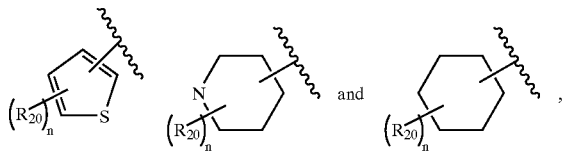

wherein n is 0, 1 or 2, and $R_{20a}$ is selected from the group of $R_{20}$ except $R_{20a}$ is not halogen or $CO_2H$.

4. A compound according to claim 1, or a pharmaceutically-acceptable salt, hydrate or prodrug thereof, in which t is 0 and either:

(a) s is 0 and Z is selected from:

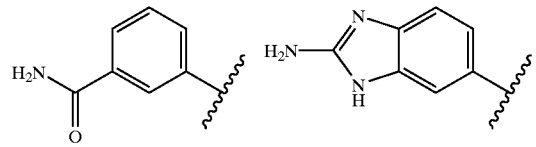

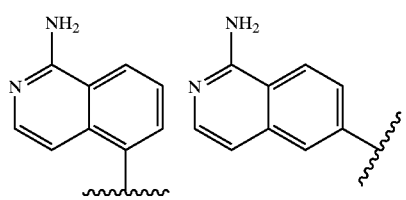

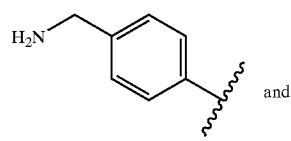 and

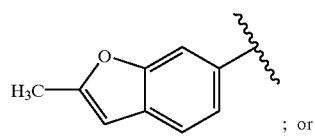

; or (b) s is 1 and Z is selected from:

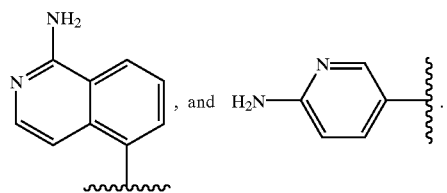

5. A compound according to claim 1, or a pharmaceutically-acceptable salt, hydrate or prodrug thereof, in which s and t are 0 and Z is

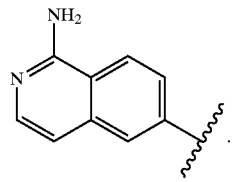

6. A compound according to claim 5, or a pharmaceutically-acceptable salt, hydrate or prodrug thereof, in which Y is —NHC(=O)—.

7. A compound according to claim 1, or a pharmaceutically-acceptable salt, hydrate or prodrug thereof, in which W is —C(=O)NH—CH($R_{25}$)—C(CH₃)₃ and $R_{25}$ is hydrogen, $C_{1-4}$alkyl, or $C_{1-4}$hydroxyalkyl.

8. A compound according to claim 1, or a pharmaceutically-acceptable salt, hydrate or prodrug thereof, having the formula:

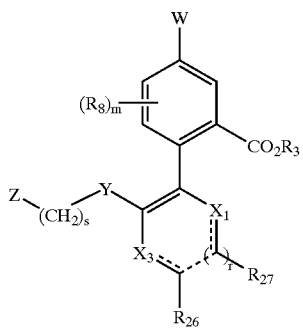

in which:
- $X_1$ is selected (i) from —$CR_9R_{10}$—, —C(=O)—, —$NR_{9a}$—, —O— and —S— when the bond between $X_1$ and the adjacent carbon atom to which $R_{27}$ is attached (or when r is 0, the carbon atom to which $R_{26}$ is attached) is a single bond, and (ii) from —$CR_9$— and —N— when said bond is a double bond;
- $X_3$ is selected (i) from $CH_2$ and NH when the bond between $X_3$ and the adjacent carbon atom to which $R_{26}$ is attached is a single bond, and (ii) from —CH— and —N— when said bond is a double bond;
- $R_9$ and $R_{10}$ are independently selected from hydrogen, hydroxy, alkoxy, amino, alkylamino, alkyl, alkenyl, substituted alkyl, substituted alkenyl, halogen, haloalkyl, haloalkoxy, cyano, nitro, alkylthio, —C(=O)H, acyl, —$CO_2H$, and alkoxycarbonyl;
- $R_{9a}$ is selected from hydrogen, hydroxy, alkoxy, alkyl, alkenyl, substituted alkyl, and substituted alkenyl;
- $R_{26}$ and $R_{27}$ are selected from hydrogen, $OR_{30}$, $NR_{31}R_{32}$, alkyl, alkenyl, substituted alkyl, substituted alkenyl, halogen, haloalkyl, haloalkoxy, cyano, nitro, alkylthio, —C(=O)H, acyl, —$CO_2H$, alkoxycarbonyl, and phenyl, or (ii) $R_{26}$ and $R_{27}$ may be taken together to form a fused benzo ring when Z is not phenyl substituted in the para position with cyano or a five-membered heterocycle or heteroaryl; and
- r is 0 or 1.

9. The compound of claim 1, or a pharmaceutically-acceptable salt, hydrate or prodrug thereof, in which
W is —C(=O)NHCH($R_{25}$)-t-butyl;
L is —NHC(=O)—;
$R_3$ is hydrogen, lower alkyl, or lower alkyl substituted with —OC(=O)(alkyl), —OC(=O)O-(alkyl), —OC(=O)(cycloalkyl), or —OC(=O)O(cycloalkyl); and
$R_{25}$ is hydrogen or hydroxymethyl.

10. A compound according to claim 1, having a formula selected from (i)

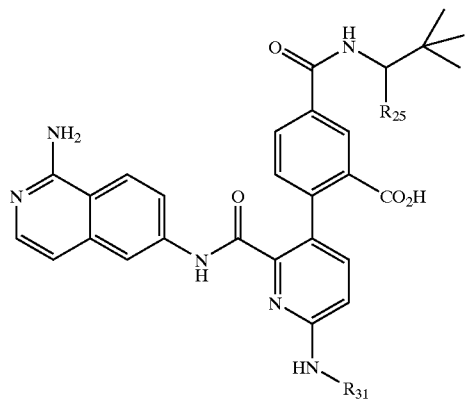

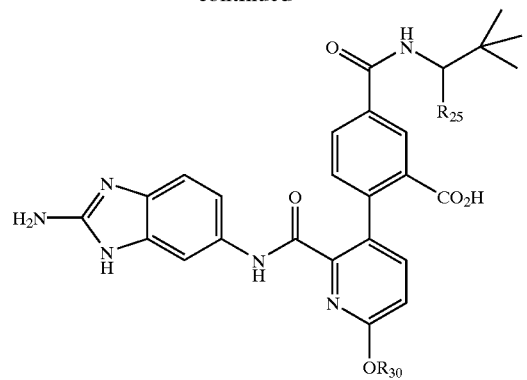

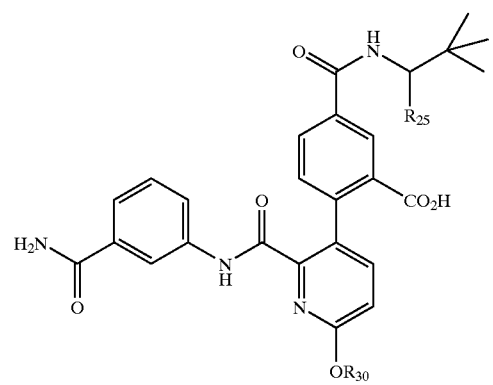

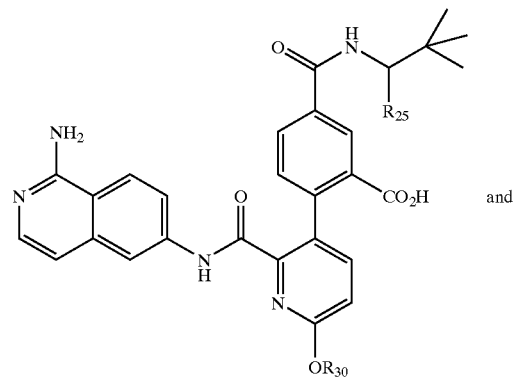

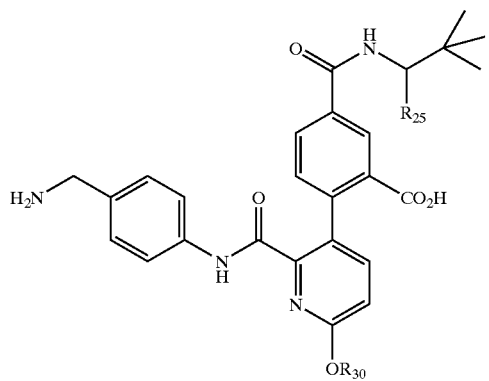

in which $R_{25}$ is hydrogen or hydroxymethyl, and $R_{30}$ and $R_{31}$ are lower alkyl, or (ii) a pharmaceutically-acceptable salt, hydrate or prodrug thereof.

11. A compound having a formula (IA):

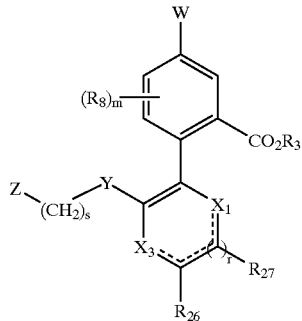

(IA)

or a pharmaceutically-acceptable salt, hydrate or prodrug thereof, wherein:

W is —C(=O)NR$_4$R$_5$;

$X_1$ is selected (i) from —CR$_9$R$_{10}$—, —C(=O)—, —NR$_{9a}$—, —O— and —S— when the bond between $X_1$ and the adjacent carbon atom to which R$_{27}$ is attached (or when r is 0, the carbon atom to which R$_{26}$ is attached) is a single bond, and (ii) from —CR$_9$— and —N— when said bond is a double bond;

$X_3$ is selected (i) from —CR$_{11}$R$_{12}$—, —C(=O)—, —NR$_{11a}$—, —O— and —S— when the bond between $X_3$ and the carbon atom to which R$_{26}$ is attached is a single bond, and (ii) from —CR$_{11}$— and —N— when said bond is a double bond;

Y is selected from —C(=O)NR$_{13}$—, —NR$_{13}$C(=O)—, —NR$_{13}$CR$_{14}$R$_{15}$—, —CR$_{14}$R$_{15}$—NR$_{13}$—, and —CR$_{13}$R$_{14}$—CR$_{15}$R$_{16}$—, or Y may be —C(=O)—, when Z is

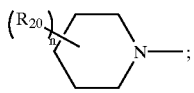

Z is selected from a 5 to 7-membered monocyclic or 8 to 11-membered bicyclic aryl, heteroaryl, heterocyclo, or cycloalkyl, wherein each Z group is optionally substituted with up to two R$_{20}$ and/or up to one R$_{21}$;

$R_1$ and $R_2$ (ii) are taken together to form a five-to-seven membered heterocyclo; wherein when $R_1$ and $R_2$ together form a cyclic group, said cyclic group is optionally substituted with up to two R$_{26}$;

$R_3$ is hydrogen, alkyl, or substituted alkyl;

$R_4$, $R_{4a}$ and $R_5$ are (i) independently selected from hydrogen, alkyl, substituted alkyl, alkenyl, substituted alkenyl, alkynyl, substituted alkynyl, heteroalkyl, substituted heteroalkyl, aryl, heteroaryl, heterocyclo, and cycloalkyl; or alternatively (ii) $R_4$ and $R_5$ may be taken together to form a five-to-seven membered heteroaryl or heterocyclo ring, except when W is —S(O)$_p$R$_4$, then $R_4$ is not hydrogen;

$R_6$ is C$_{2-6}$alkyl, phenyl, or benzyl;

$R_8$, $R_9$, $R_{10}$, $R_{11}$, $R_{12}$, $R_{26}$ and $R_{27}$ (i) are at each occurrence independently selected from hydrogen, OR$_{30}$, NR$_{31}$R$_{32}$, NR$_{31}$SO$_2$R$_{32a}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl, or (ii) when r is 1, R$_{26}$ and R$_{27}$ may be taken together to form a fused benzo ring, provided that when R$_{26}$ and R$_{27}$ form a fused benzo ring then Z is not phenyl substituted in the para position with cyano or a five-membered heterocycle or heteroaryl;

$R_{9a}$ and $R_{11a}$ are selected from hydrogen, OR$_{30}$, NR$_{31}$R$_{32}$, alkyl, alkenyl, substituted alkyl, substituted alkenyl, —C(=O)H, acyl, alkoxycarbonyl, sulfonamido, sulfonyl, and phenyl, $R_{13}$, $R_{14}$, $R_{15}$, and $R_{16}$ are selected from hydrogen, lower alkyl, hydroxy, or lower alkyl substituted with hydroxy or halogen;

$R_{20}$ and $R_{21}$ are independently selected from hydrogen, halogen, alkyl, substituted alkyl, haloalkyl, haloalkoxy, cyano, nitro, —C(=O)NR$_{22}$R$_{23}$, —OR$_{22}$, —CO$_2$R$_{22}$, —C(=O)R$_{22}$, —SR$_{22}$, —S(O)$_q$R$_{22a}$, —NR$_{22}$R$_{23}$, —NR$_{22}$SO$_2$R$_{23}$, —NR$_{22}$CO$_2$R$_{23}$, —NR$_{22}$C(=O)R$_{23}$, —SO$_2$NR$_{22}$R$_{23}$, —NR$_{22}$C(=O)NR$_{23}$R$_{33}$, —NR$_{22}$SO$_2$NR$_{23}$R$_{33}$, five or six membered heterocyclo or heteroaryl, phenyl, and four to seven membered cycloalkyl, wherein when R$_{20}$ and/or R$_{21}$ comprise a cyclic group, each cyclic group is in turn optionally substituted with up to three lower alkyl, halogen, hydroxy, haloalkyl, haloalkoxy, amino, aminoalkyl, or cyano;

$R_{22}$, $R_{23}$, and $R_{33}$ are independently selected from hydrogen, halogen, alkyl, and substituted alkyl;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl, and cycloalkyl;

$R_{22a}$ and $R_{32a}$ at each occurrence are independently selected from alkyl, substituted alkyl, and cycloalkyl;

m is 0, 1 or 2;

p and q are independently 1 or 2;

r is 0 or 1; and s is 0 or 1.

12. A compound according to claim 11 having the formula (IA), in which $X_3$ is N, CH, or CH$_2$, or a pharmaceutically-acceptable salt, hydrate or prodrug thereof.

13. A compound according to claim 11 having the formula:

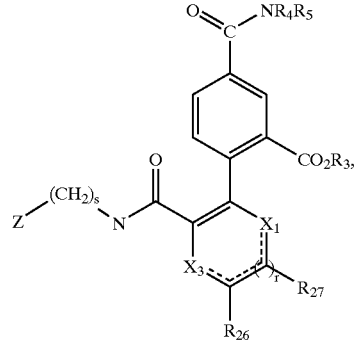

or a pharmaceutically-acceptable salt, hydrate or prodrug thereof.

14. A compound according to claim 13 or a pharmaceutically-acceptable salt, hydrate or prodrug thereof in which (a) s is 0 and Z is selected from:

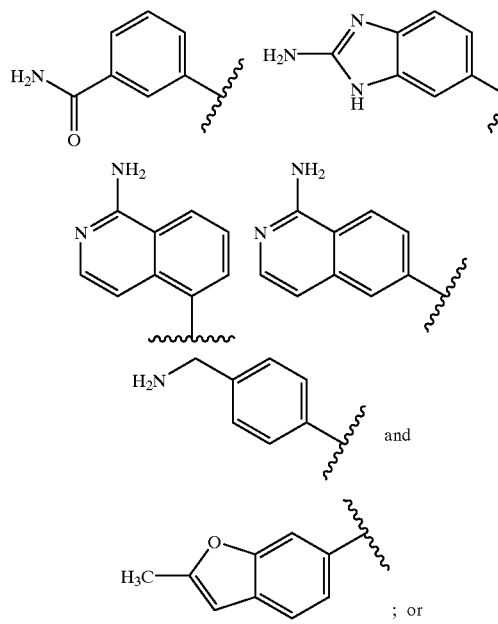

; or (b) s is 1 and Z is selected from:

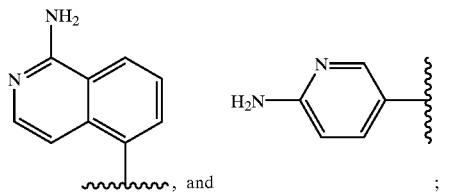

$R_{26}$ is $C_{2-6}$ straight or branched alkenyl, —$OR_{30}$ or —$NR_{31}R_{32}$;

$R_{30}$ is $C_{1-5}$ straight or branched chain alkyl, $C_{2-6}$ straight or branched alkenyl, $C_{3-5}$ cycloalkyl, or $C_{1-4}$ straight or branched chain alkyl substituted with one to two of halogen, lower alkoxy, and $C_{3-5}$ cycloalkyl; and $R_{31}$ and $R_{32}$ are selected from hydrogen and lower alkyl.

15. A compound according to claim 11, in which the groups Z—$(CH_2)_s$—Y— taken together are selected from:

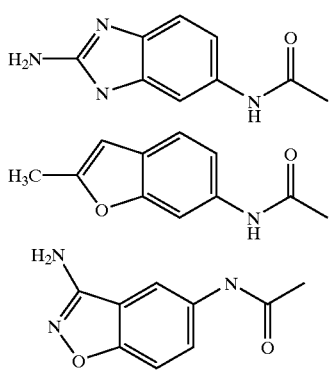

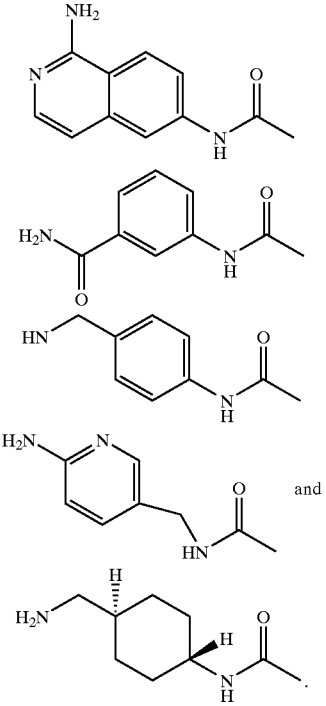

16. A compound having the formula (IA):

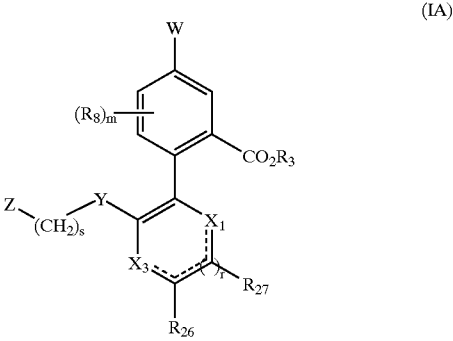

(IA)

or a pharmaceutically-acceptable salt, hydrate or prodrug thereof, wherein:

W is —C(=O)$NR_4R_5$;

$X_1$ is selected (i) from —$CH_2$—, —NH—, —O— and —S— when the bond between $X_1$ and the carbon atom to which $R_{27}$ is attached (or when r is 0, the bond between $X_1$ and the carbon atom to which $R_{26}$ is attached) is a single bond; and (ii) from —CH— and —N— when said bond is a double bond;

$X_3$ is selected (i) from —$CH_2$—, —NH—, —O— and —S— when the bond between $X_3$ and the carbon atom to which $R_{26}$ is attached is a single bond, and (ii) from —CH— and —N— when said bond is a double bond;

Y is selected from —NHC(=O)—, —NH—$CH_2$—, and —$CH_2$—$CH_2$—, or Y may be —C(=O)— when Z is

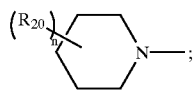

Z is selected from:

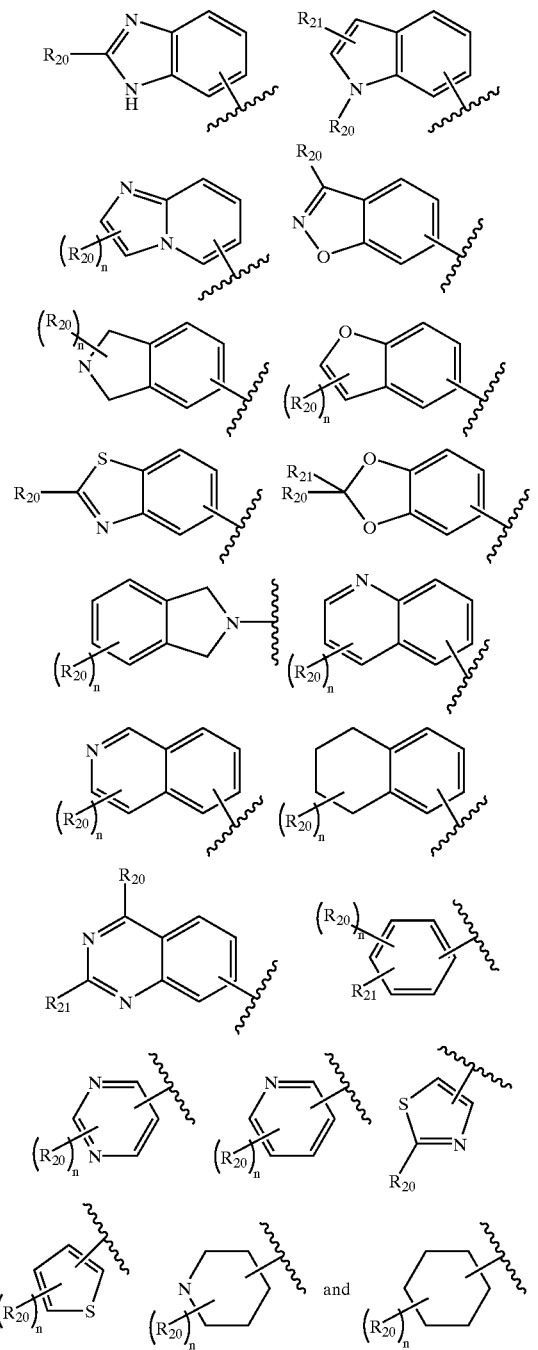

$R_1$ and $R_2$ (ii) are taken together to form a five-to-seven membered heterocyclo;

$R_3$ is hydrogen or $C_{1-4}$alkyl;

$R_4$ is selected from hydrogen, $C_{1-4}$alkyl, and $C_{1-4}$alkyl substituted with hydroxy;

$R_5$ is selected from:
  i) $C_{1-10}$alkyl or $C_{1-10}$alkenyl;
  ii) $C_{1-6}$alkyl or $C_{1-10}$alkenyl substituted with one to three of:
     a) OH, keto (=O), —$OC_{1-4}$alkyl;
     b) partially or fully saturated cycloalkyl in turn optionally substituted with $C_{1-4}$alkyl or hydroxy;
     c) phenyl in turn optionally substituted with halogen, hydroxy, methoxy, $C_{1-4}$alkyl, —$SO_2NH_2$, or —$NO_2$;
     d) heteroaryl in turn optionally substituted with methyl;
     e) heterocyclo; and/or
     f) NHPhenyl;
  iii) heteroaryl or heterocyclo optionally substituted with $NH_2$;

alternatively, $R_4$ and $R_5$ together form a heterocyclo or heteroaryl optionally substituted with hydroxy, $C_{1-4}$alkyl, and $C_{1-4}$alkyl substituted with one or more of hydroxy and/or phenyl;

$R_6$ is selected from $C_{2-4}$alkyl, phenyl and benzyl;

$R_{26}$ and $R_{27}$ at each occurrence are independently selected of each other from the group consisting of hydrogen, $C_{1-4}$alkyl, $C_{2-4}$alkenyl, $OR_{30}$, $NR_{31}R_{32}$, phenyloxy, and benzyloxy, or when r is 1, $R_{26}$ and $R_{27}$ may be taken together to form a fused benzo ring, provided that when $R_{26}$ and $R_{27}$ form a fused benzo ring then Z is not phenyl substituted in the para position with a five-membered heterocycle or heteroaryl;

$R_{20}$ and $R_{21}$ are independently selected from hydrogen, halogen, —C(=O)$NH_2$, —C(=O)$C_{1-4}$alkyl, —$NH_2$, —$NHC_{1-4}$alkyl, —S—$C_{1-4}$alkyl, —O—$C_{1-4}$alkyl, $C_{1-4}$alkyl, $C_{1-4}$alkyl substituted with $NH_2$, and five or six membered heterocyclo or heteroaryl;

$R_{30}$ at each occurrence is selected from hydrogen, alkyl, substituted alkyl, alkenyl, substituted alkenyl, cycloalkyl, and phenyl;

$R_{31}$ and $R_{32}$ at each occurrence are independently selected from hydrogen, alkyl, substituted alkyl, alkenyl, substituted alkenyl, and cycloalkyl;

n is 0, 1 or 2;

r is 0 or 1; and s is 0 or 1.

17. A compound according to claim 16, or a pharmaceutically acceptable salt, hydrate or prodrug thereof, in which Z is:

a) a 6,5 bicyclic heteroaryl selected from:

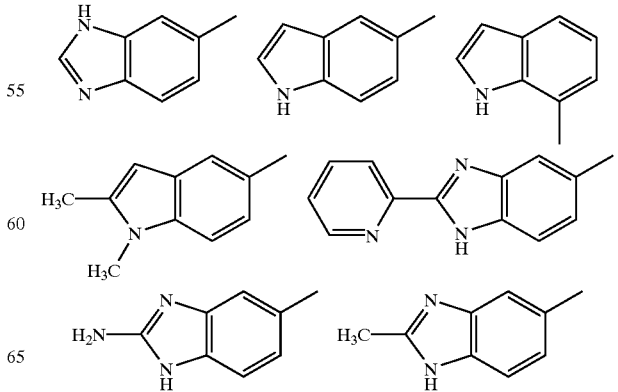

-continued
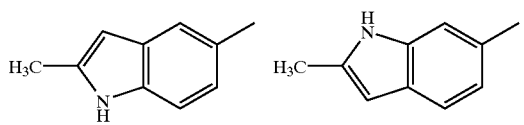
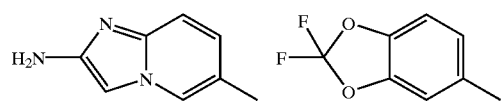
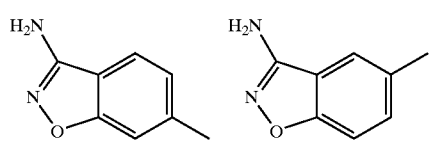
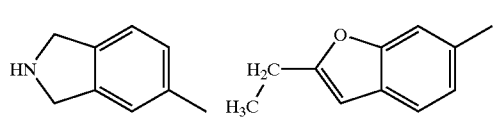
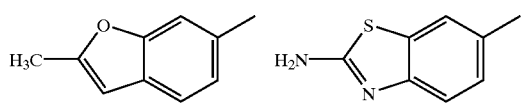
and
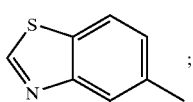
;
b) the 5,6 bicyclic heteroaryl group
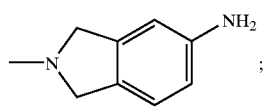
;
c) a 6,6 bicyclic heteroaryl or aryl group selected from:
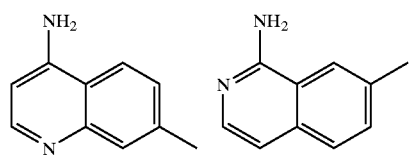
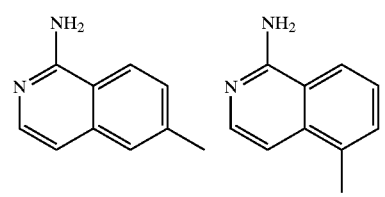
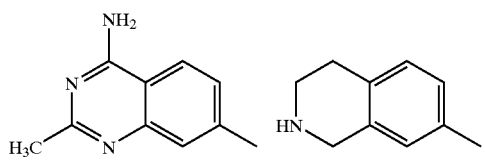
-continued
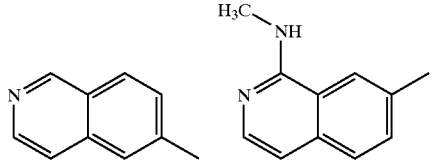
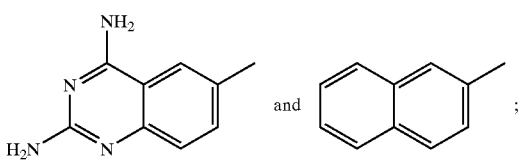 and ;
d) a phenyl group selected from:
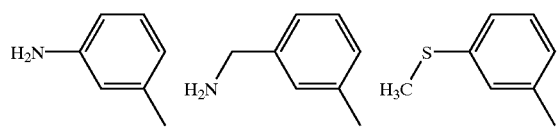
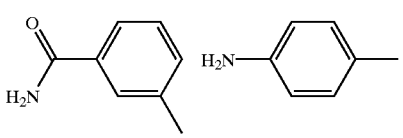
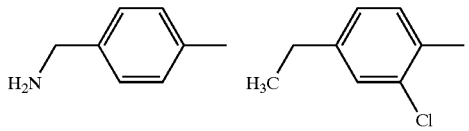
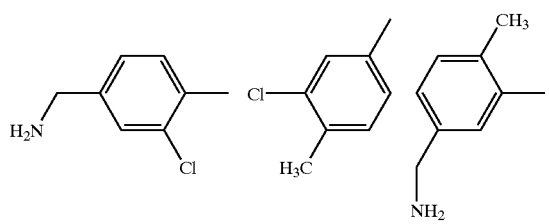
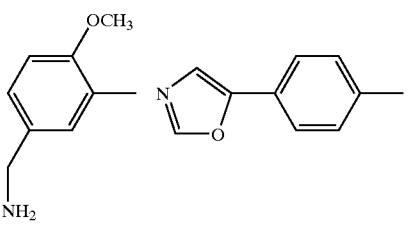
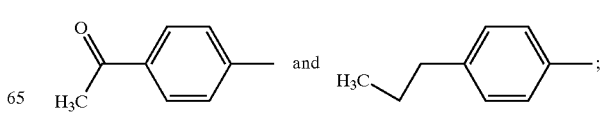 and ;

e) a monocyclic heteroaryl group selected from:

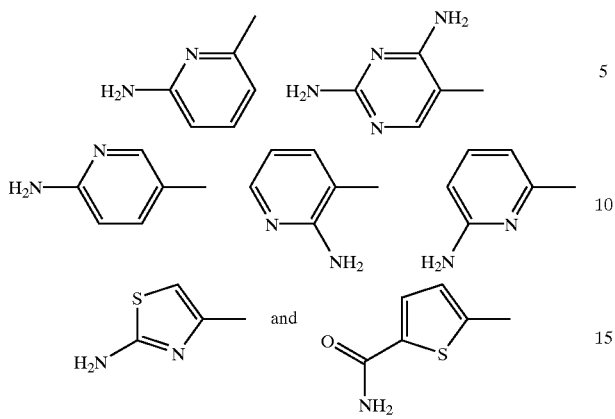

f) a heterocyclo group selected from:

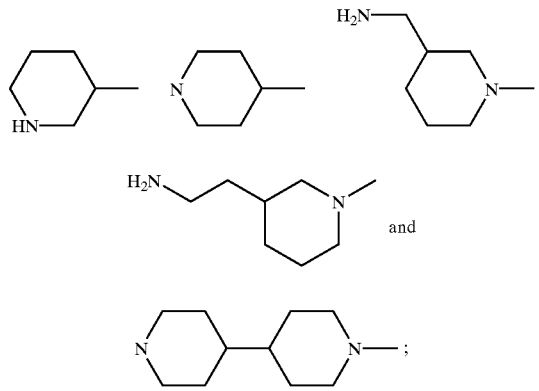

or g) a cycloalkyl group selected from:

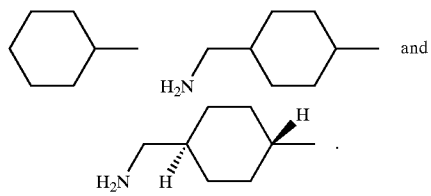

18. A compound according to claim 16 or a pharmaceutically acceptable salt, hydrate or prodrug thereof, having the formula:

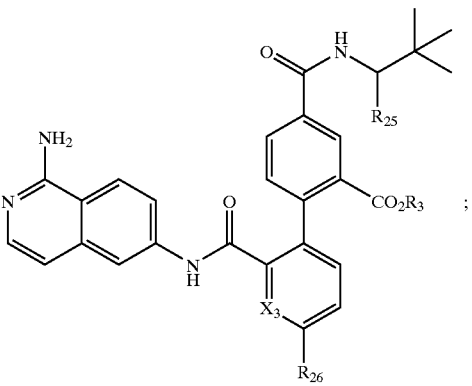

in which $R_{25}$ is hydrogen or hydroxymethyl, and $R_{26}$ is $NR_{31}R_{32}$.

19. A pharmaceutical composition comprising (a) at least one compound according to claim 1, or a pharmaceutically acceptable salt, hydrate or prodrug thereof, and (b) a pharmaceutically acceptable carrier or diluent.

20. A pharmaceutical composition comprising (a) at least one compound according to claim 11, or a pharmaceutically acceptable salt, hydrate or prodrug thereof, and (b) a pharmaceutically acceptable carrier or diluent.

21. A pharmaceutical composition for treating an inflammatory or immune disorder comprising (a) at least one compound according to claim 1, or a pharmaceutically acceptable salt, hydrate or prodrug thereof, (b) at least one second compound for treating an an inflammatory or immune disorder and (b) a pharmaceutically acceptable carrier or diluent.

22. A pharmaceutical composition for treating a coagulation-associated disorder comprising (i) at least one compound of claim 1 or a pharmaceutically acceptable salt, hydrate or prodrug thereof; (ii) one or more second compounds effective for treating a coagulation-associated disorder; and (iii) a pharmaceutically-acceptable carrier.

23. A method of treating a coagulation-associated disorder, an inflammatory or immune disease, or metastases comprising administering to a mammal in need thereof a therapeutically-effective amount of at least one compound according to claim 1.

24. A method for maintaining a blood supply in the fluid phase comprising administering to said blood supply at least one compound according to claim 1.

* * * * *